(12) United States Patent
Domecus et al.

(10) Patent No.: US 12,390,098 B2
(45) Date of Patent: Aug. 19, 2025

(54) SYSTEMS, DEVICES, AND METHODS FOR VISUALIZATION DURING MEDICAL PROCEDURES

(71) Applicant: TUSKER MEDICAL, INC., Menlo Park, CA (US)

(72) Inventors: Brian Domecus, Menlo Park, CA (US); Mahyar Z. Kermani, San Ramon, CA (US); Rohit Girotra, San Francisco, CA (US); Eric Goldfarb, Belmont, CA (US); Andrew Lantz, Redwood City, CA (US); Robert Edwin Schneider, Erie, CO (US); Tyler Bennett Bigham, Boulder, CO (US)

(73) Assignee: Tusker Medical, Inc., Menlo Park, CA (US)

( * ) Notice: Subject to any disclaimer, the term of this patent is extended or adjusted under 35 U.S.C. 154(b) by 602 days.

(21) Appl. No.: 17/623,726

(22) PCT Filed: Jul. 17, 2020

(86) PCT No.: PCT/US2020/042484
§ 371 (c)(1),
(2) Date: Dec. 29, 2021

(87) PCT Pub. No.: WO2021/011855
PCT Pub. Date: Jan. 21, 2021

(65) Prior Publication Data
US 2022/0240771 A1 Aug. 4, 2022

Related U.S. Application Data

(60) Provisional application No. 62/875,298, filed on Jul. 17, 2019.

(51) Int. Cl.
*A61B 1/227* (2006.01)
*A61B 1/00* (2006.01)
(Continued)

(52) U.S. Cl.
CPC .......... *A61B 1/227* (2013.01); *A61B 1/00045* (2013.01); *A61B 1/00114* (2013.01);
(Continued)

(58) Field of Classification Search
CPC ....... A61B 1/227–1/2275; A61B 1/233; A61B 1/05; A61B 1/06; A61B 1/00045; A61B 1/00165
See application file for complete search history.

(56) References Cited

U.S. PATENT DOCUMENTS 4,034,759 A 7/1977 Haerr
4,159,719 A 7/1979 Haerr
(Continued)

FOREIGN PATENT DOCUMENTS

CN 102122067 A 7/2011
CN 105725955 A 7/2016
(Continued)

OTHER PUBLICATIONS

European Application No. 20753579.0-1122 Examination Report dated Feb. 24, 2022.
(Continued)

*Primary Examiner* — Julianna N Harvey
(74) *Attorney, Agent, or Firm* — Dickinson Wright PLLC

(57) ABSTRACT

Visualization during medical procedures is provided using a visualization system comprising: a control device defining an upper surface and a lower surface; a display visible through the upper surface of the control device; a handle coupled to the lower surface and extending away from the lower surface; a knob coupled to the control device, the knob configured to rotate about a rotational axis; an imaging assembly mechanically coupled to the knob and communicatively coupled to the control device, the imaging assembly configured to rotate around the rotational axis based on
(Continued)

rotation of the knob; and the control device configured to display an image on the display, the image captured by the imaging assembly.

14 Claims, 33 Drawing Sheets

(51) Int. Cl.
*A61B 1/05* (2006.01)
*A61B 1/06* (2006.01)
*A61B 1/32* (2006.01)

(52) U.S. Cl.
CPC ............ *A61B 1/00165* (2013.01); *A61B 1/05* (2013.01); *A61B 1/06* (2013.01); *A61B 1/32* (2013.01)

(56) References Cited

U.S. PATENT DOCUMENTS

| | | | |
|---|---|---|---|
| 4,706,682 | A | 11/1987 | Stypulkowski |
| 5,300,018 | A | 4/1994 | Walsh |
| 5,489,286 | A | 2/1996 | Cinberg et al. |
| 5,954,682 | A | 9/1999 | Petrus |
| 6,045,528 | A | 4/2000 | Arenberg et al. |
| 6,120,484 | A | 9/2000 | Silverstein |
| 6,358,231 | B1 | 3/2002 | Schindler |
| 6,685,697 | B1 | 2/2004 | Arenberg |
| 8,052,693 | B2 | 11/2011 | Shahoian |
| 8,747,883 | B2 | 6/2014 | Labib et al. |
| 8,864,774 | B2 | 10/2014 | Liu et al. |
| 8,998,927 | B2 | 4/2015 | Kaplan et al. |
| 9,233,068 | B2 | 1/2016 | Lichter et al. |
| 9,320,652 | B2 | 4/2016 | Andreas et al. |
| 9,326,668 | B1 * | 5/2016 | Berbee ............... A61B 1/00112 |
| 9,370,448 | B2 | 6/2016 | Loushin et al. |
| 9,681,891 | B2 | 6/2017 | Andreas et al. |
| 9,833,360 | B2 | 12/2017 | Andreas et al. |
| 2010/0256653 | A1 | 10/2010 | Kaplan et al. |
| 2011/0208161 | A1 | 8/2011 | Ivri |
| 2012/0130252 | A1 | 5/2012 | Pohjanen et al. |
| 2012/0253267 | A1 | 10/2012 | Reed et al. |
| 2014/0276906 | A1 | 9/2014 | Andreas et al. |
| 2015/0293877 | A1 | 10/2015 | Liang et al. |
| 2016/0022497 | A1 | 1/2016 | Labib et al. |
| 2016/0038342 | A1 | 2/2016 | Van et al. |
| 2016/0067179 | A1 | 3/2016 | Lichter et al. |
| 2017/0172804 | A1 | 6/2017 | Watanabe et al. |
| 2017/0239091 | A1 | 8/2017 | Franz et al. |
| 2018/0125345 | A1 | 5/2018 | Rebella et al. |
| 2019/0167378 | A1 | 6/2019 | Wood |
| 2020/0337544 | A1 | 10/2020 | Goldfarb et al. |
| 2021/0038234 | A1 | 2/2021 | Amis et al. |

FOREIGN PATENT DOCUMENTS

| | | |
|---|---|---|
| GB | 842965 A | 10/1958 |
| TW | 201200098 A | 1/2012 |
| WO | 0128407 A1 | 4/2001 |
| WO | 02056756 A2 | 7/2002 |
| WO | 2015168642 A1 | 11/2015 |
| WO | 2019143587 A1 | 7/2019 |

OTHER PUBLICATIONS

International Search Report and Written Opinion for International Application No. PCT/US2020/042484, International Filing Date Jul. 17, 2020, Date of Mailing Jan. 21, 2021, 17 pages.
Chinese Office Action for CN Application No. 201980006220.6, 7 pages.
European Office Action mailed May 24, 2023 for EP Application No. 19703486.1-1126, 7 pages.
Communication pursuant to Rules 161(1) and 162 EPC for EP 19703486.1 dated Sep. 3, 2020, 3 pages.
International Preliminary Report on Patentability mailed Jul. 21, 2020 for International Application No. PCT/US2019/013568, 12 pages.
International Search Report and Written Opinion mailed Jun. 14, 2019 for International Application No. PCT/US2019/013568, 18 pages.
Japanese Office Action mailed Jan. 30, 2023 for JP Application No. 2020536682, 3 pages.

* cited by examiner

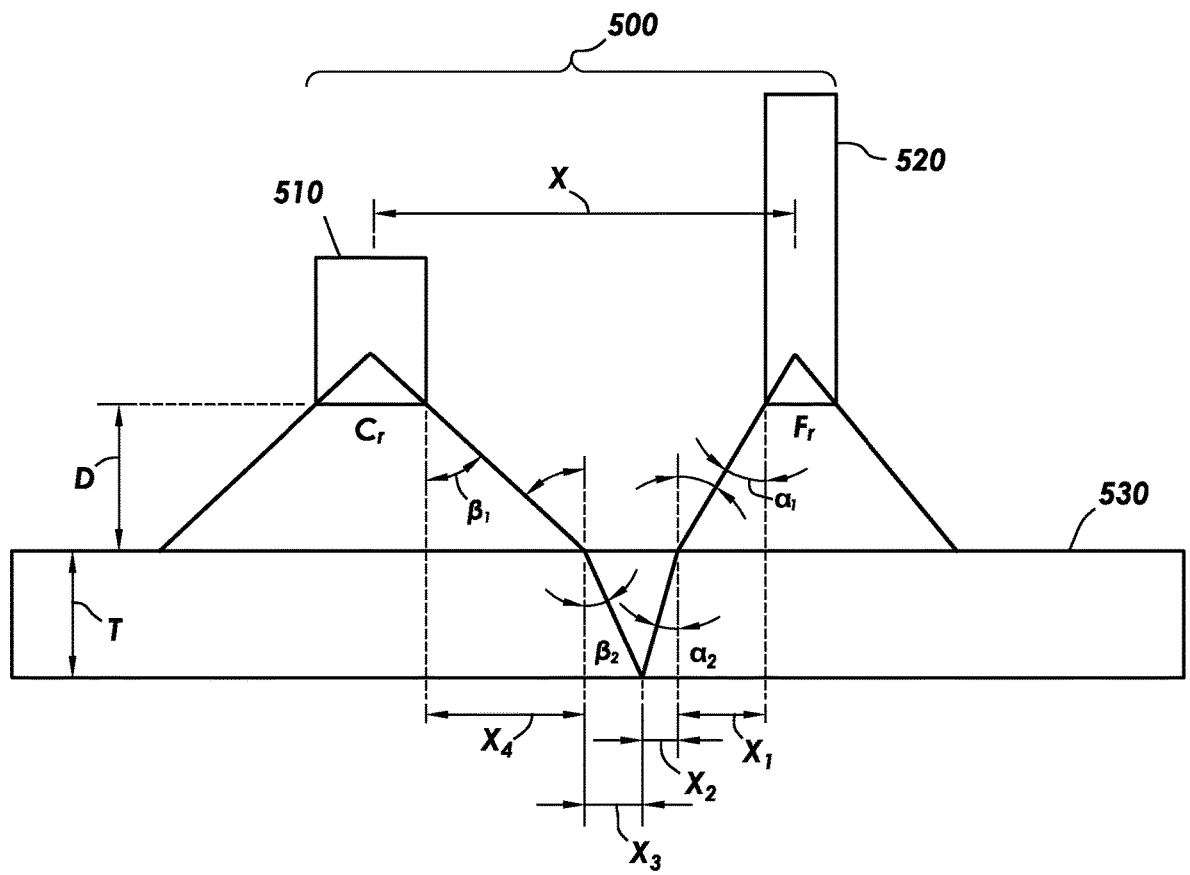
FIG.5
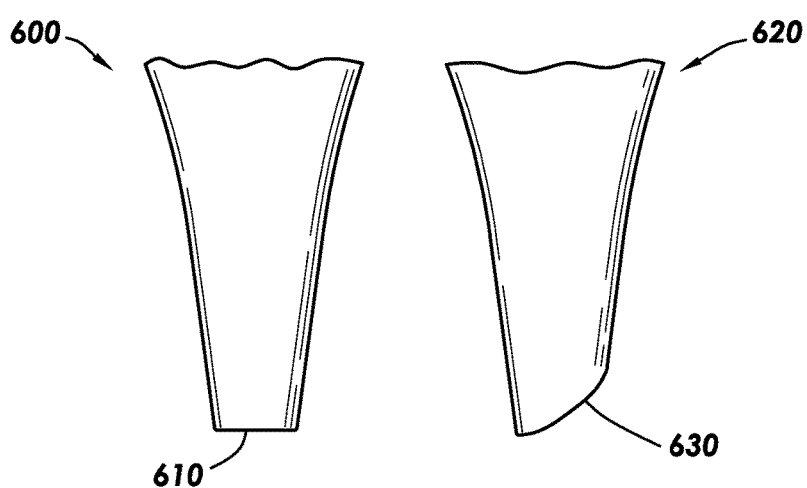
FIG.6A   FIG.6B

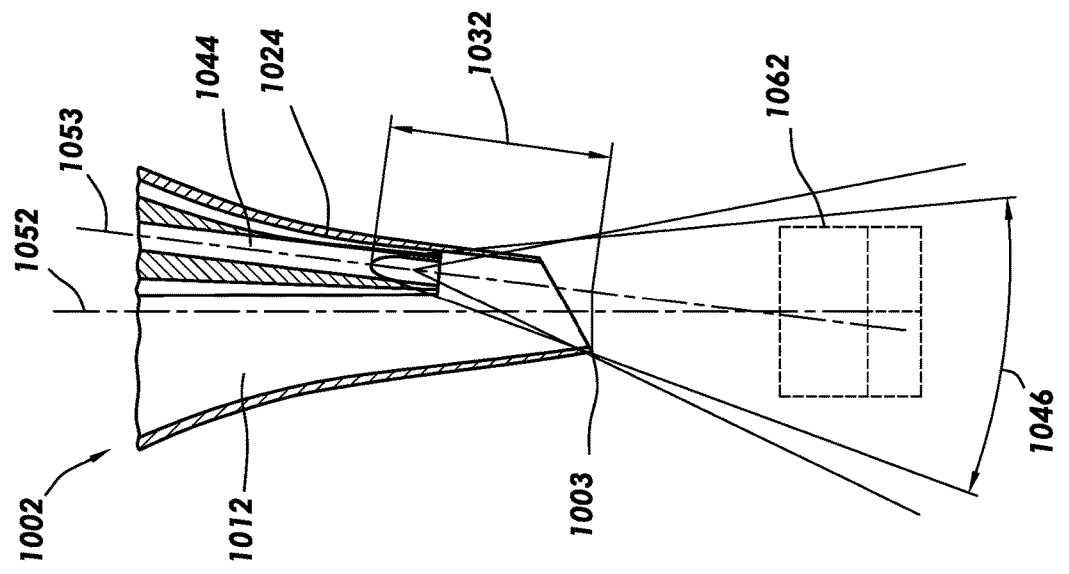
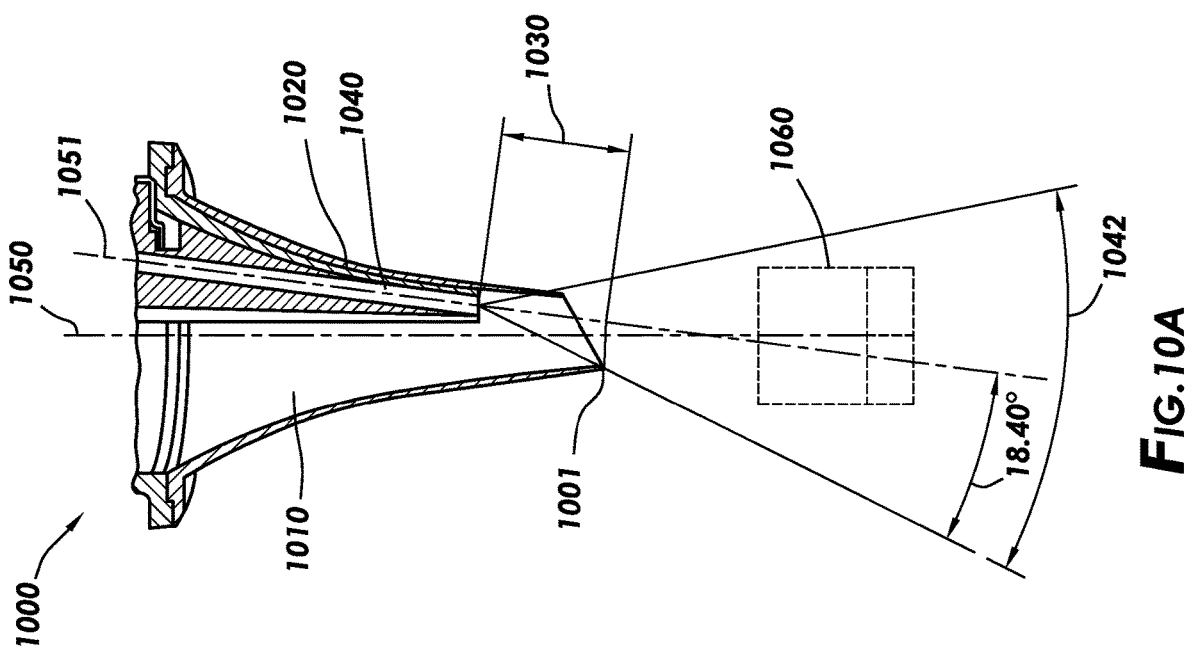

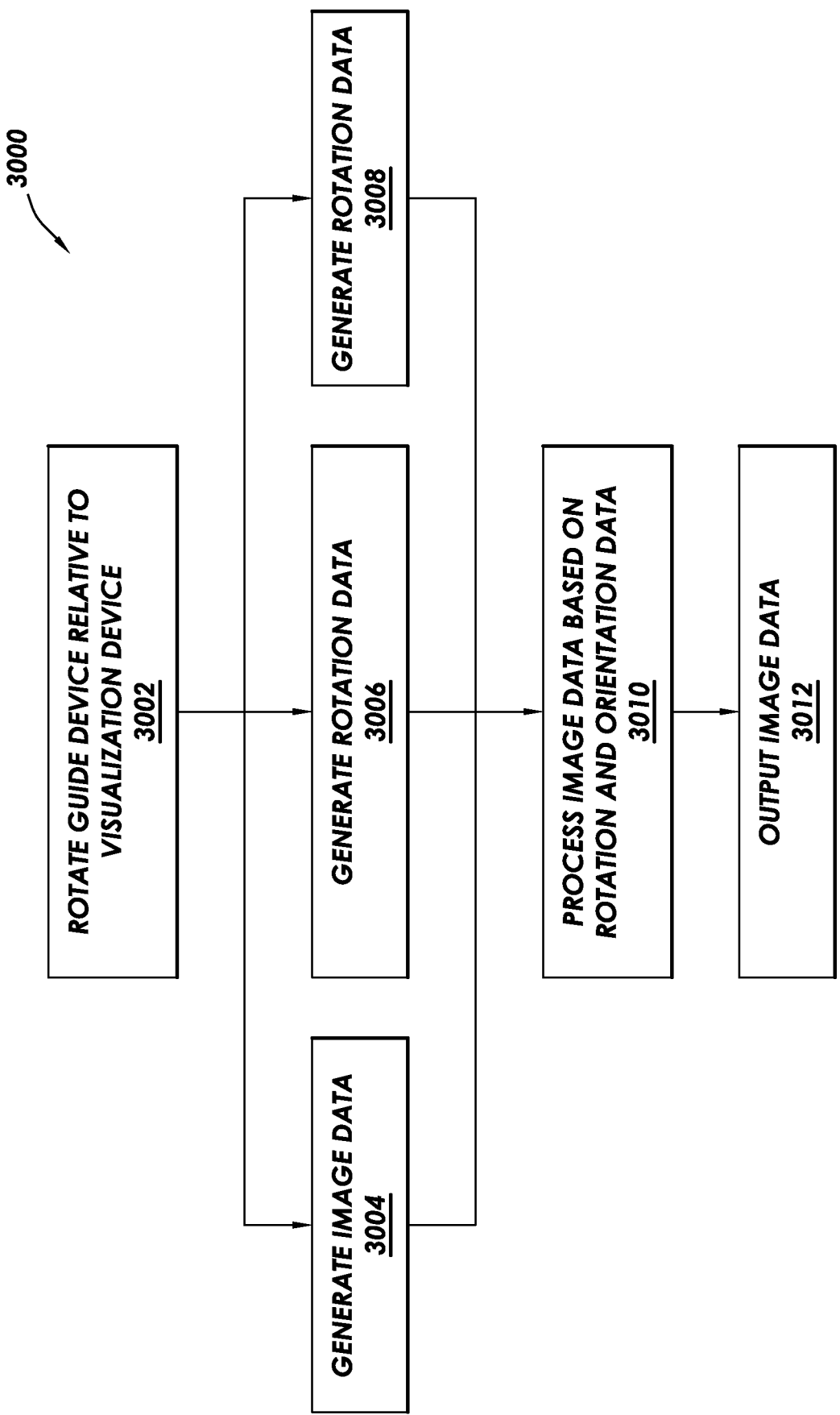

SYSTEMS, DEVICES, AND METHODS FOR VISUALIZATION DURING MEDICAL PROCEDURES

CROSS-REFERENCE TO RELATED APPLICATIONS

This application is a U.S. National Phase entry of PCT Application No. PCT/US2020/042484 filed Jul. 17, 2020 titled "Systems, Devices, And Methods For Visualization During Medical Procedures." The PCT application claims the benefit of U.S. Provisional App. No. 62/875,298 filed Jul. 17, 2019 titled "Systems, Devices, And Methods For Visualization Of Orifices During Medical Procedures." Both applications are incorporated by reference herein as if reproduced in full below.

TECHNICAL FIELD

Various example embodiments relate to systems, devices, and methods for tissue visualization and more particularly to visualization of an ear canal and the structures therein during otological diagnostics and procedures.

BACKGROUND

Otologic procedures, or procedures relating to the ear, involve the insertion of a medical instrument into an ear of a patient. During an otologic procedure, it may be difficult for a physician to view inside the ear. Otologic procedures may be performed using a surgical microscope that provides visualization of the ear but requires a line-of-sight view to a target treatment area. When operating with an instrument within the ear canal, however, the access path of the instrument oftentimes overlaps or blocks the line of sight between the microscope and the target treatment area. Therefore, a clinician may be restricted in operation of the instrument or must operate with an incomplete view of the target treatment area. In addition, the view provided by a microscope may be susceptible to the motion of a patient. Therefore, it is desirable to have a system for otologic procedures that allows instrument access to a target treatment area while providing a clear view that is does not become out of focus based on patient motion.

SUMMARY

At least one example embodiment is a visualization system comprising: a control device defining an upper surface and a lower surface; a display visible through the upper surface of the control device; a handle coupled to the lower surface and extending away from the lower surface; a knob coupled to the control device, the knob configured to rotate about a rotational axis; an imaging assembly mechanically coupled to the knob and communicatively coupled to the control device, the imaging assembly configured to rotate around the rotational axis based on rotation of the knob; and the control device configured to display an image on the display, the image captured by the imaging assembly.

The example visualization may further comprise: a rotation sensor in operational relationship to the knob and communicatively coupled to the control device, the rotation sensor configured to sense rotational of the knob and the imaging assembly; wherein the control device is configured to rotate the image on the display responsive to rotation of the knob such that the image remains in a consistent orientation despite rotation of the image assembly. The rotation sensor may further comprise: a first conductive pattern; a second conductive pattern distinct from and electrically isolated from the first conductive pattern; a conductive member coupled to the knob; a measurement circuit electrically coupled to the first conductive pattern, the second conductive pattern, and the conductive member; the measurement circuit configured to sense rotation of the knob based on a capacitive measurement between the conductive member, the first conductive pattern, and the second conductive pattern. In some cases, the first conductive pattern may further comprise a wide end having a first width and a narrow end having a second width smaller than the first width, the first conductive pattern extending in a circular pattern; and the second conductive pattern may further comprise a wide end having a third width and a narrow end having a fourth width smaller than the third width, the second conductive pattern extending in a circular pattern alongside the first conductive pattern; and a width of the first conductive pattern gets smaller with circular distance in a first direction around the circular pattern, and a width of the second conductive pattern gets larger in the first direction around the circular pattern.

The example visualization system may further comprise: a post defining a proximal end and a distal end, the proximal end of the post coupled to the lower surface of the control device, and the post extending away from the lower surface; a base coupled to the distal end of the post, the base defining an upper surface, a lower surface, and an aperture; the knob disposed on the upper surface of the base; and the imaging assembly extending through the aperture and below the lower surface of the base. The post may further comprise: a first notch medially disposed on a first side of the post, the first notch defines a closed bottom, an open top, and a channel; and a second notch medially disposed on a second side of the post opposite the first side, the second notch defines a closed bottom, an open top, and a channel. The example visualization system may further comprise the channel of the first notch being parallel with the channel of the second notch.

In the example visualization the imaging assembly may further comprise: an elongate shaft defining a proximal end and a distal end, the proximal end rigidly coupled to the knob; an optical sensor disposed within the elongate shaft, the optical sensor defining an optical axis, and the optical sensor communicatively coupled to the control device; and an illumination source disposed within the elongate shaft; wherein the optical axis forms a non-zero angle with the rotational axis of the knob. The example visualization system may further comprise: a distal optical lens disposed on the distal end of the elongate shaft, the imaging assembly having a field of view through the distal optical lens along the optical axis; and an illumination window disposed on the distal end of the elongate shaft, the illumination window having a illumination ray path at least partially coextensive with the field of view. In some cases, the optical axis of the optical sensor intersects the rotational axis of the knob.

The example visualization system may further comprise a communication cable coupled between the imaging assembly and the control device, the communication cable remains coupled between the control device and the imaging assembly as a rotational orientation of the knob changes. The example system may further comprise: a base rigidly coupled to the control device, the base defining an aperture; a stationary circular rack rigidly coupled to and at least partially circumscribing the aperture; a rotatable circular rack rigidly coupled to the knob and at least partially circumscribing the rotational axis of the knob; a pinion disposed between the stationary circular rack and the rotatable circular rack, the pinion configured to translate along the stationary circular rack responsive to relative rotational movement of the rotatable circular rack; a circular disk having an annular channel defined on an outside diameter of the circular disk, the circular disk coupled to the pinion and configured to translate with the pinion; and the communication cable at least partially circumscribes the circular disk within the annular channel.

The example visualization system may further comprise: a speculum defining a longitudinal axis and a distal tip, the speculum coupled to the knob such that the longitudinal axis is coaxial with the rotational axis of the knob, and the speculum rotates as the knob rotates; an imaging lumen disposed on an inside surface of the speculum, the imaging lumen defining a closed bottom, the imaging assembly disposed within the imaging lumen; and a working channel defined through the speculum, the working change distinct from the imaging lumen.

In the example visualization system, a distal end of the imaging lumen may define a setback distance from the distal tip such that a field of view of the imaging assembly overlaps a portion of an inside diameter of the speculum at the distal tip. In some cases, the speculum defines a shape of an inverted conic frustum.

Other example embodiments are a speculum for use with a surgical otoscope, the speculum comprising: an outer wall defining a frustum with a longitudinal central axis;

a proximal end defining a first aperture; a distal tip defining a second aperture, the second aperture smaller than the first aperture; an internal volume defined by an inside surface of the outer wall; an imaging lumen disposed on the inside surface, the imaging lumen having a proximal end that is open and a distal end; a working channel defined by a remainder of the internal volume not occupied by the imaging lumen; and a window disposed at the distal end of the imaging lumen, the window fluidly isolates the imaging lumen from the working channel.

In the example speculum, the second aperture may define a plane that is perpendicular to the longitudinal central axis. In some cases, the distal end of the imaging lumen is disposed at an axial position relative to the longitudinal central axis different than an axial position of the distal tip. In some cases, the axial positon of the distal end of the imaging lumen is between 9 and 13 millimeters, inclusive.

The example may further comprise: a proximal portion that defines a first aperture fluidly coupled to the working channel, and a second opening fluidly coupled to the imaging lumen; and a distal portion that defines an inverter frustum. The example speculum may further comprise a means for coupling the speculum to a surgical otoscope, the means for coupling disposed at an intersection of the proximal portion and the distal portion. The means for coupling may further comprise an annular surface that circumscribes the speculum at the intersection of the proximal portion and the distal portion. The means for coupling may further comprise: a leaf spring partially circumscribing the speculum at the intersection of the proximal portion and the distal portion, the leaf spring defining an annular groove; an engagement member medially disposed on an outer surface of the leaf spring; wherein in a non-compressed orientation of the leaf spring the means for coupling defines a first diameter, and in a compressed orientation the means for coupling defines a second diameter smaller than the first diameter.

The example speculum may further comprise: an optical axis defined by the imaging lumen and the window disposed at the distal end of the imaging lumen; the optical axis intersects the longitudinal central axis at a location beyond the distal tip of the speculum. In some cases, an angle between the optical axis and the longitudinal central axis is about 7.5 angular degrees.

Other example embodiments are a method of performing on otological procedure, comprising: displaying images of an ear canal on a display device of an otoscope, the images captured by an imaging assembly in operational relationship to a speculum within the ear canal, the images in a first rotational orientation; sensing rotation of the speculum and the imaging assembly; and rotating, by the otoscope, the images on the display device responsive to the sensing such that the images remain in the first rotational orientation.

The example method may further comprise, prior to insertion into the ear canal, coupling the speculum to the otoscope such that the imaging assembly is disposed within an imaging lumen of the speculum. The example method may further comprise: inserting an instrument through a working channel of the speculum; displaying on the display device a physical relationship between a distal end of the instrument and an anatomical structure within the ear canal; and performing an otological procedure using the instrument.

Example otological procedure may further comprise performing at least one selected from a group comprising: a myringotomy; a tympanostomy tube delivery; wax removal; and foreign body removal.

In the example method, displaying images may further comprise displaying in the images at least a portion of a distal end of the speculum in the images.

The example method may further comprise: coupling the speculum to the otoscope such that the imaging assembly is disposed within an imaging lumen of the speculum; holding the otoscope by a clinician, the otoscope residing on a plane defined by the thumb and index finger a hand of the clinician; placing the speculum and the imaging assembly the ear canal; stabilizing the otoscope by resting a lower portion of the hand of the clinician on a head of a patient. In some cases, the first rotational orientation corresponds to a perspective of the clinician relative to the patient.

BRIEF DESCRIPTION OF THE DRAWINGS

For a detailed description of example embodiments, reference will now be made to the accompanying drawings in which:

FIG. 5 shows, in block diagram form, considerations regarding an illumination source, an optical sensor, and thickness of the optical tip, in accordance with at least some embodiments;

FIGS. 6A and 6B show side elevation views of two example speculums in accordance with at least some embodiments;

FIGS. 10A and 10B are cross-sectional views of speculums to show placement of the imaging lumens relative to the speculum tip, in accordance with at least some embodiments;

FIG. 30 is an example method of image processing for visualization of a target treatment area, in accordance with at least some embodiments;

DEFINITIONS

Figure 1:
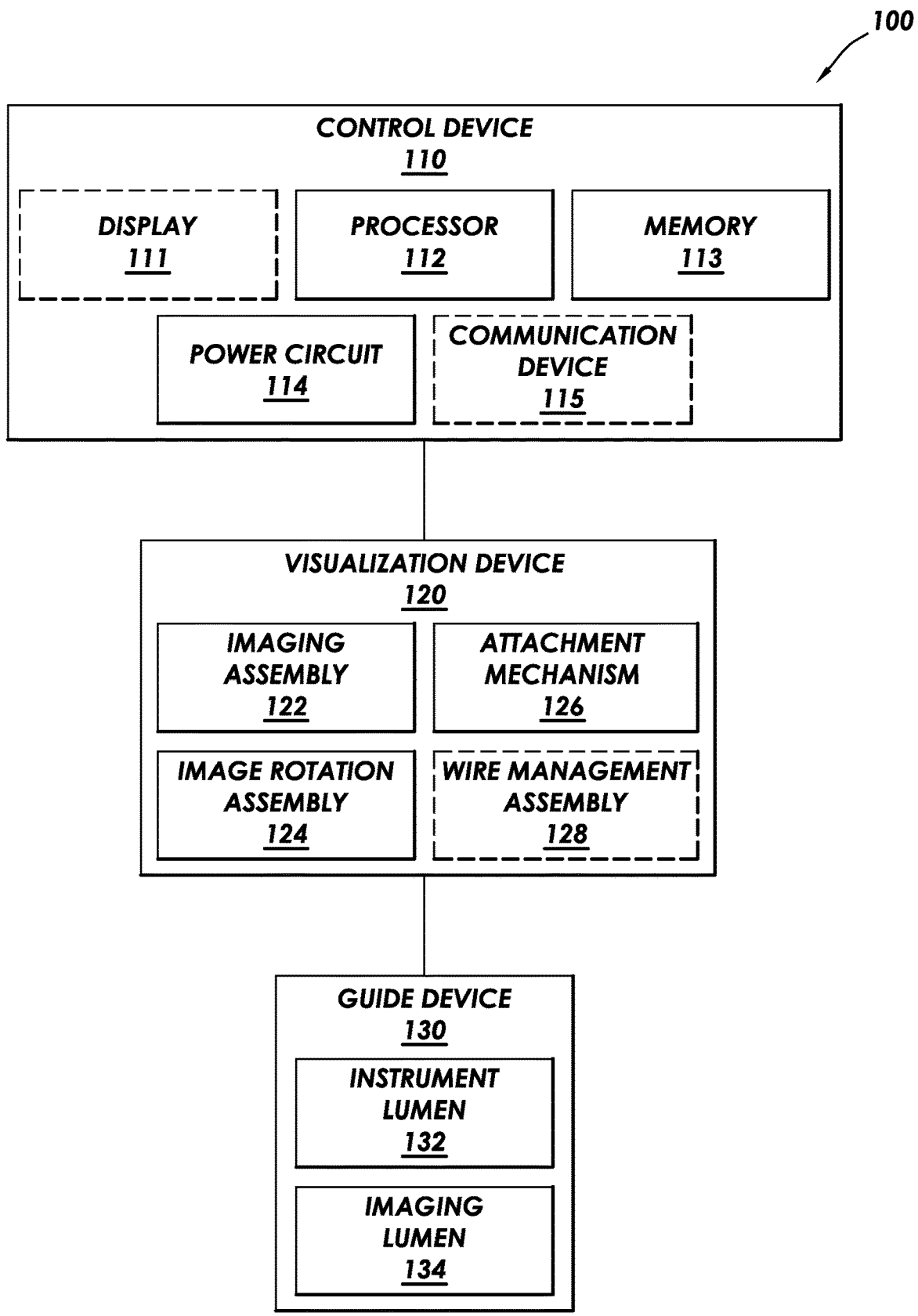
FIG. 1 is a block diagram of a visualization system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terms 'transparent', 'transparency', and variants thereof shall mean light transmission at a predetermined wavelength and/or range of wavelengths of about 10% or more through an object, while the terms 'opaque', 'opacity', 'opaqueness', and variants thereof shall mean light transmission at the predetermined wavelength and/or range of wavelengths of about 10% or less through an object. For example, acrylic may be considered transparent as it provides about 90% transmission of wavelengths from UV through infrared.

The terms "about" and/or "approximately" when used in conjunction with numerical values and/or ranges refer to those numerical values and/or ranges near to a recited numerical value and/or range. The terms "about" and "approximately" shall mean within ±10% of the recited value. For example, in some instances, "about 100 [units]" may mean within ±10% of 100 (e.g., from 90 to 110). The terms "about" and "approximately" may be used interchangeably.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Some medical procedures, such as in an ear canal, may be challenging to perform and visualize due to sensitive tissue, constrained anatomy, and the size of devices disposed therein. Accordingly, one or more of an image resolution, field of view (FOV), device access, and device range of motion (ROM) are conventionally limited. In addition, views provided by conventional systems may be susceptible to patient motion (e.g., move in response to patient motion) which can further limit a clinician's ability to consistently view the patient anatomy and/or track movement of a medical instrument relative to the patient anatomy.

Various example embodiments are directed systems, devices, and methods for visualizing an orifice of a patient. The systems, devices, and methods may be used to visualize an ear canal at regions of interest during an otological diagnostic and treatment procedure. An example visualization system may include a speculum configured to be advanced into an ear canal of a patient. A speculum may be removably coupled to a surgical otoscope (hereafter just "scope") that includes an imaging assembly (e.g., camera), display, and rotation mechanism. When the speculum is attached to the scope, at least a portion of the imaging assembly may be disposed within an imaging lumen of the speculum. The speculum may be advanced into the ear canal such that the imaging assembly enables visualization of the ear canal. An instrument may be advanced into the ear canal through an instrument lumen (e.g. "working channel") of the speculum. The clinician may manipulate the instrument and speculum while performing a procedure. For example, the clinician may rotate the speculum relative to the scope to modify instrument access of the ear canal.

As described in more detail below, the systems, devices, and methods may improve one or more of a field of view, range of motion, image resolution, and ease of use. For example, image data output to a clinician may be processed to compensate for rotation of the speculum such that a consistent orientation is provided to the clinician. Moreover, in some embodiments, the speculum may be separable from the scope such that the scope may be a reusable and the speculum may be a single-use disposable component.

The specification is organized as shown in the following outline:
 I. VISUALIZATION SYSTEM BLOCK DIAGRAM
 II. EXAMPLE VISUALIZATION SYSTEM
  A. GUIDE DEVICE OR SPECULUM
   i. SETBACK AND FIELD OF VIEW
   ii. OPTICAL AXIS ANGLE B. VISUALIZATION DEVICE
  i. IMAGING ASSEMBLY
  ii. ATTACHMENT MECHANISM
  iii. IMAGE ROTATION ASSEMBLY
  Iii. WIRE MANAGEMENT ASSEMBLY
C. CONTROL DEVICE
  i. DISPLAY
  ii. PROCESSOR
  iii. MEMORY
  iv. POWER CIRCUIT
  v. COMMUNICATION DEVICE
III. METHODS The specification turns first to a high level overview of the example systems.

I. VISUALIZATION SYSTEM BLOCK DIAGRAM

FIG. 1 is a block diagram of a visualization system 100 in accordance with at least some embodiments. In particular, FIG. 1 shows a control device 110, a visualization device 120 (e.g., scope portion of a handheld device), and a guide device 130 (e.g., speculum). In some embodiments, the control device 110 can be coupled to and/or integrated with the visualization device 120. In some embodiments, portions of the visualization system 100, such as the control device 110 and visualization device 120, are designed to be reusable (e.g., used multiple times, and with one or more patients). In some cases, the guide device 130 is designed to be reusable, while in other embodiments the guide device 130 is designed to be a single use, disposable item.

The guide device 130, hereafter referred to as the speculum 130, may include a distal portion that is sized and shaped to be placed into an orifice of a patient, such as an ear canal. The speculum 130 may include one or more lumens such as an instrument lumen 132 and an imaging lumen 134. The instrument lumen 132 may function as a working channel that enables passage of one or more instruments through the working channel for accessing a space beyond an open end (tip) of the speculum 130. For example, tympanostomy tube delivery devices (e.g., as described in U.S. Pat. No. 8,052,693, titled "System and Method for the Simultaneous Automated Bilateral Delivery of Pressure Equalization Tubes," issued Nov. 8, 2011; U.S. Pat. No. 8,864,774, titled "Tympanic Membrane Pressure Equalization Tube Delivery System," issued Oct. 21, 2014; U.S. Pat. No. 9,320,652, titled "Features to Improve and Sense Tympanic Membrane Apposition by Tympanostomy Tube Delivery Instrument," issued Apr. 26, 2016; U.S. Pat. No. 9,681,891, titled "Tympanostomy Tube Delivery Device with Cutting Dilator," issued Jun. 20, 2017; U.S. Patent Application Publication No. 2016/0038342, titled "Tympanostomy Tube Delivery Device with Rotatable Flexible Shaft," published Feb. 11, 2016; and U.S. Pat. No. 9,833,360, titled "Tympanostomy Tube Delivery Device with Replaceable Shaft Portion," issued Dec. 5, 2017) can be inserted through instrument lumen (132) into a portion of the ear canal adjacent to the tympanic membrane. The visualization device 120, in some embodiments, including an imaging assembly 122, may be disposed in the imaging lumen 134 and configured to generate image data corresponding to one or more of tissues and anatomy during a procedure.

In some embodiments, the visualization device 120 may be configured to output image data and further configured to enable rotation of the speculum 130 relative to a portion of the visualization device 120. In some embodiments, the visualization device 120 may include the imaging assembly 122, an image rotation assembly 124, an attachment mechanism 126, and a wire management assembly 128. The imaging assembly 122 may be configured to generate image data for output on a user interface, such as the control device 110. In some embodiments, the visualization device 120 can be attached to, operatively coupled to, and/or integrated with a main body of the control device 110.

In some embodiments, the control device 110 may include a processer 112, a memory 113, a power circuit 114, and a display 111 or communication device 115. In other embodiments, the visualization device 120 can transmit information (e.g., via communication device 115) to a remote computing device including a display or other user interface.

As described in more detail below, portions of the imaging assembly 122 may be configured to be advanced into the imaging lumen 134 of the speculum 130. The imaging assembly 122 may include sensors (e.g., optical sensors, imaging sensors, etc.) and illumination sources (e.g., light emitters). The image rotation assembly 124 may be configured to enable an operator to rotate portions of the visualization device 120 and the speculum 130 relative to other portions of the visualization device 120. For example, the image rotation assembly 124 can enable rotation of the speculum 130 and the imaging assembly 122 relative to the remaining portions of the visualization device 120 (e.g., using a rotatable knob). In some embodiments, the image rotation assembly 124 includes sensors that are configured to generate data including, for example, position data, rotation data, and/or orientation data of the speculum 130 and/or imaging assembly 122. The data generated by the image rotation assembly 124 may be used (e.g., by processor 112) to process the image data received from the visualization device 120 to provide a view of a portion of the ear canal that has a predetermined (e.g., consistent) image orientation. In some embodiments, the attachment mechanism 126 couples the speculum 130 to the visualization device 120 in a selectively releasable fashion.

In example cases the visualization device 120 comprises the wire management assembly 128. The example wire management assembly 128 is configured to provide wired connections between the imaging assembly 122 and one or more components of the control device 110 (e.g., display 111, processor 112, power circuit 114) while enabling rotation of the imaging assembly 122 relative to the visualization device 120. In other embodiments, different components of the visualization device 120 can be configured to exchange information via a wireless connection (e.g., Bluetooth, WiFi, etc.). For example, imaging assembly 122 can include a communication device (e.g., a transmitter or transceiver) that can send information (e.g., imaging data, position data, and/or other sensor data) to one or more components of the control device 110 (e.g., display 111, processor 112, power circuit 114).

The processor 112 and memory 113 may be configured to perform many tasks. For example, the processor 112 and memory 113 may control the visualization device 120 and process data received from sensors of the visualization device 120. The processor 112 and memory 113 may communicate information (e.g., via the communication device 115) to other computing devices, including a remote computing device. The example power circuit 114 provides power to the visualization device 120. In some embodiments, the visualization device 120 can include an onboard power supply operatively coupled to the power circuit 114. In other cases, the visualization device 120 is connected (e.g., via a wired connection) to an external power supply.

The communication device 115 may be configured to transmit and receive data from one or more computing devices. For example, the communication device 115 can transmit imaging data regarding a patient to a computing device for storage, analysis, and/or future review (e.g., in cases involving training).

II. EXAMPLE VISUALIZATION SYSTEM

Figure 2:
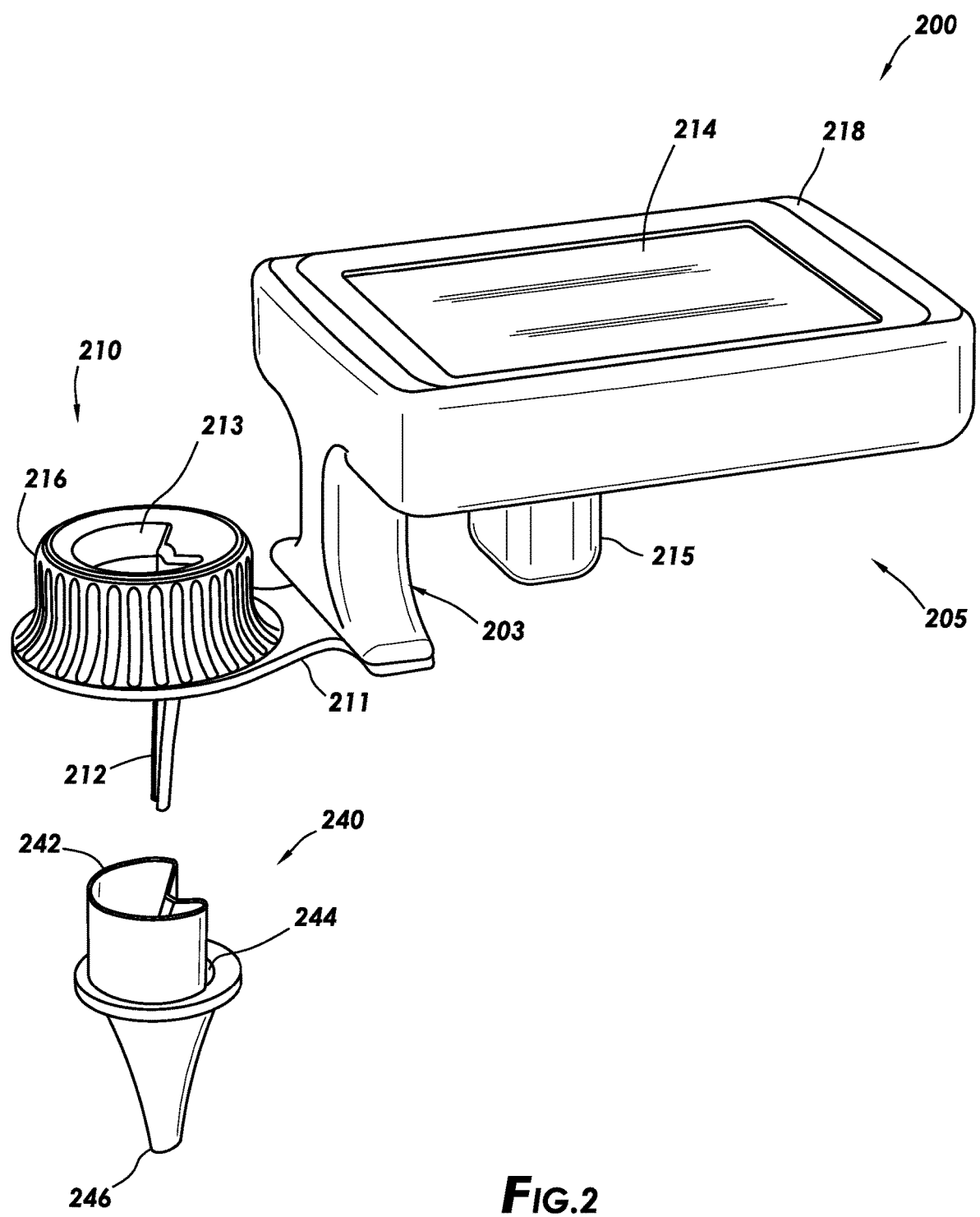
FIG. 2 is a perspective view of a visualization system in accordance with at least some embodiments.

FIG. 2 is a perspective view of a visualization system 200 including a control device 205, a visualization device 210, and a speculum 240. The visualization device 210 comprises a base 211 (e.g., hub) coupled to an imaging assembly 212, and an image rotation assembly 216. The base 211 may include a movable or adjustable linkage (e.g., flexible linkage) between the image rotation assembly 216 and a display 214 disposed within housing 218. The imaging assembly 212 may be coupled to the image rotation assembly 216 so as to enable rotation of the imaging assembly 212 relative to the base 211. The example imaging assembly 212 may include an elongate portion (e.g., optical sensor support arm) configured to extend components of the imaging assembly 212 into the speculum 240. More particularly, the elongate portion may be designed and constructed to fit within an imaging lumen 244 of the speculum 240.

A processor (not visible in FIG. 2) disposed within the housing 218 may be communicatively coupled to the image rotation assembly 216. The image rotation assembly 216 and the base 211 may define an opening 213 (e.g., aperture, through hole, working channel) configured to enable an instrument to pass through an instrument lumen 242 of the speculum 240. In example systems, the opening 213 is configured to receive a proximal portion of the instrument lumen 242 of the speculum 240 such that the opening 213 and imaging lumen 244 is protected from contact with an instrument (not shown for the sake of clarity) or the ingress of fluid (e.g., solid, liquid particles) that may enter into the speculum 240 (e.g., to protect from biological contamination).

In the example shown, the base 211 is coupled to the housing 218, and the housing 218 encloses and/or supports the display 214 and other electronic components of the visualization system 200, such as the processor, the memory, the power circuit, the battery, and the communication device similar to those components described above with respect to FIG. 1. In some embodiments, a grip, handle, hand piece or palm support 215 may be extend from the housing 218 in a direction opposite the display 214. The example palm support 215 is configured for a clinician to hold the visualization system 200 and position the visualization system 200 relative to the patient. The palm support 215 may be adjustable, (e.g., extendable, slidable, rotatable, etc.) relative to the housing 218. In some embodiments, a clinician may use a single hand to hold and operate the visualization system 100. For example, the clinician may use one hand to hold the palm support 215, and another hand to manipulate an instrument (not shown). Additionally or alternatively, a clinician may hold the palm support 215 while using one or more of the fingers and thumb to rotate the image rotation assembly 216.

In particular, the example housing 218 defines a post 203. The post 203 defines a proximal end coupled to a bottom side of the housing 218, and the post 203 extends parallel to the palm support 215. In the example of FIG. 2, the post 203 defines two finger notches, one finger notch on each side, and thus the example post 203 defines an inverted "T" shape. In use, the visualization system 200 is placed on the clinician's hand, and more particularly the bottom side of the housing 218 rests on a plane defined by the index finger and thumb of the clinician. The palm support 215 resides at the intersection of the index finger and thumb. The index finger extends through one finger notch of the post 203 to touch the image rotation assembly 216, and the thumb extends through the other finger notch of the post 203 to also touch the image rotation assembly 216. Thus, the clinician may turn the image rotational assembly 216 while simultaneously viewing the display 214 and manipulating an instrument. In some cases, the lower portion of the clinician's hand rests on or abuts against the patient's head when the speculum and imaging assembly is disposed within the ear canal of the patient.

The example speculum 240 defines the instrument lumen 242 and the imaging lumen 244. The lower portion of the example speculum 240 has the shape of an inverted frustum such that the speculum tapers in diameter from a larger proximal end to a distal open end (e.g., at the tip 246). In some cases, the lower portion of the example speculum 240 has the shape of an inverted cone where the walls of the cone have a cross-sectional shape of the function $F(x)=-1/x^2$ (i.e., wider at the top, and asymptotically approaching longitudinal axis at the distal tip). The larger proximal open end of the speculum 240 may be selectively coupled to and decoupled from the image rotation assembly 216 via a speculum attachment mechanism (not shown in FIG. 2, but discussed more below).

In some embodiments, the visualization system 200 may be a durable assembly that may be reused for a plurality of patients and/or procedures. The visualization system 200, when used with the speculum 240, can be designed to avoid contacting any portion of the patient anatomy, while the speculum 240 is designed to contact the patient anatomy. Accordingly, after a procedure, the speculum 240 can be cleaned and/or disinfected while the visualization system 200 may not need to be disinfected. In some embodiments, the speculum 240 is a disposable component that is replaced for each patient and/or procedure (e.g., a single-use consumable). The speculum 240 can be configured to contact the patient while shielding the visualization device 210 from contacting the patient during use.

The speculum 240 may be constructed of any suitable material. In cases where the speculum 240 is a single-use consumable, the outer wall of the speculum may be a plastic material that may be clear or opaque. In cases where the speculum 240 is reusable, the speculum may be constructed using any material suitable for cleaning (e.g., autoclave), such as metallic material and some plastics.

The speculum 240 may be sized to fit a predetermined orifice, such as an ear canal. As illustrated and described in more detail below, the tip 246 of the speculum 240 may be angled. That is, in the angled tip example, a plane defined by the tip 246 is not perpendicular to a longitudinal central axis of the speculum 240. The angled tip 246 of the speculum 240 modifies a field of view of the imaging assembly 212 disposed within the imaging lumen 244 of the speculum 240.

A. Guide Device or Speculum

Figure 3A:
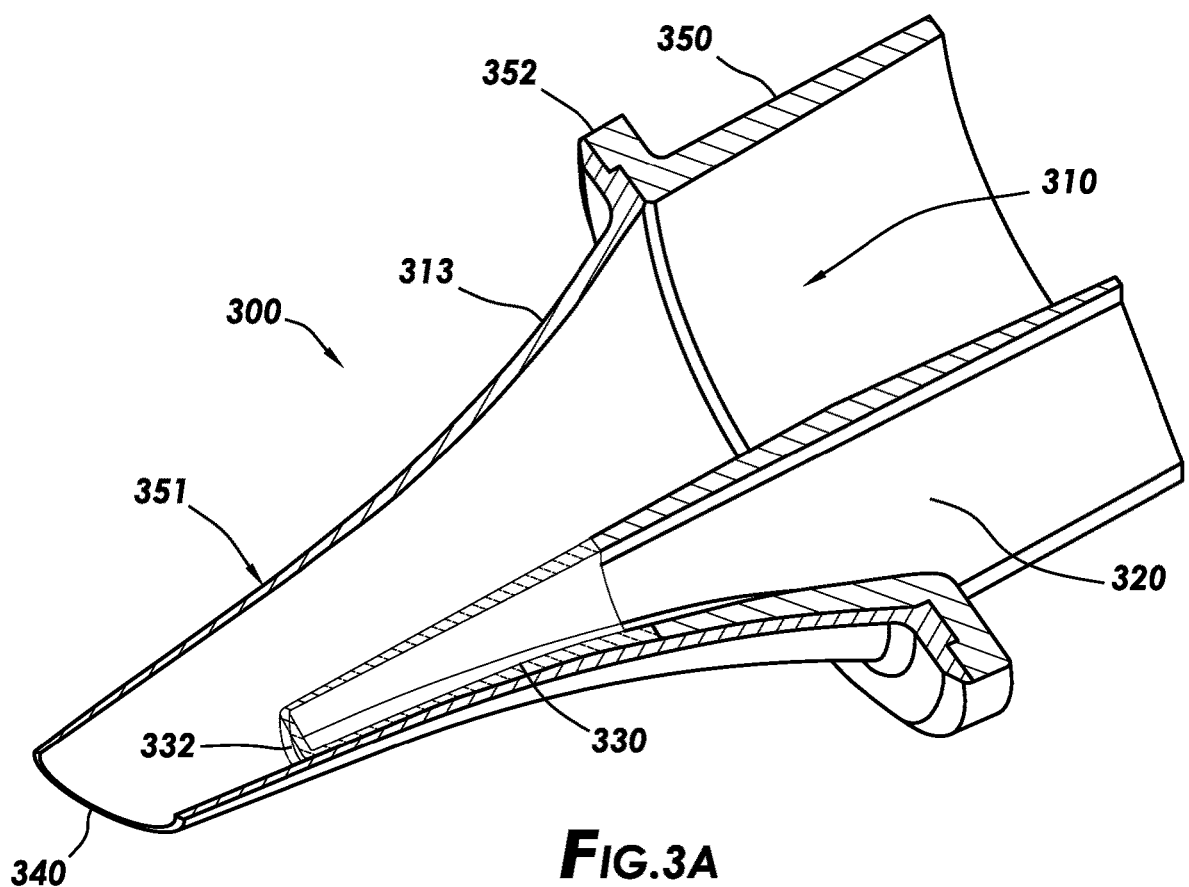
FIG. 3A is a cross-sectional perspective view of a speculum in accordance with at least some embodiments.

FIG. 3A is a cross-sectional perspective view of a speculum 300 in accordance with example embodiments. In particular, FIG. 3A shows an instrument lumen 310 (e.g., working channel), an imaging lumen 320, a speculum tip 340, and attachment portion 350. In some embodiments, the speculum 300 is supplied as a pre-assembled component, and in some cases the entire speculum 300 is disposable. In other embodiments, the speculum 300 is supplied as multiple components (e.g., a component that is designed to contact patient anatomy and a component that does not contact patient anatomy) such that certain components of the speculum 300 can be disposed while others can be retained for repeated use. For example, the frustum shaped lower portion 351 may be a disposable component, while the attachment portion 350 may be a re-usable component.

Different portions and/or components of the speculum 300 can be formed of different materials depending on the function of such portions. For example, a portion designed to contact patient anatomy (e.g., the lower portion 351) can be formed of softer materials while a portion designed to couple to the visualization device (e.g., the attachment portion 350) can be formed of a more rigid material.

The speculum tip 340, disposed at the distal end of the speculum 300, defines an aperture or outlet for an instrument advanced through the speculum 300. The instrument lumen 310 may define an aperture or inlet configured to receive an instrument. The attachment portion 350 may be configured to attach to an attachment mechanism of a scope (e.g., attachment mechanism 126 of FIG. 1). In the example shown, the attachment portion 350 includes an alignment feature (352) configured to releasably couple the speculum 300 to a scope.

In particular, the example speculum 300 comprises an outer wall 313 that defines a frustum comprising a longitudinal central axis. The outer wall 313 defines a first aperture at the tip 340, and a second aperture on the proximal end of the speculum 300. The aperture at the tip 340 is smaller than the aperture at the proximal end of the speculum 300. The outer wall 313 defines an inside diameter and an internal volume. The imaging lumen 310 is disposed on the inside diameter of the outer wall 313. The imaging lumen 310 has a proximal end and a distal end. The distal end includes a lens or optical tip 332. The example speculum further defines the instrument lumen 310 by the remainder of the internal volume not occupied by the imaging lumen 320.

In example embodiments, the speculum 300 is substantially opaque except for an optical portion 330 that may be transparent, e.g., to enable light transmission. For example, the imaging lumen 320 may include the optical portion 330 having the optical tip 332 on the distal end of the imaging lumen 320. The optical portion 330 enables an imaging assembly to provide illumination through the tip 340, and enables the imaging assembly to generate images of a target treatment area, all by passing and receiving light through the optical tip 332. In the example shown, the optical tip 332 occludes, blocks, or encloses the distal end of the imaging lumen 320 to provide a barrier between the imaging lumen 320 and the instrument lumen 310. The fluidly separated instrument lumen 310 and imaging lumen 320 enables an imaging assembly placed within the imaging lumen 320 to be protected from contact with an instrument in the instrument lumen 310 and/or the ingress of fluid that may enter into the speculum 300 from the ear canal.

In example embodiments, the imaging lumen 320 is designed and constructed to increase a cross-sectional area and/or usable volume of the instrument lumen 310. In the example shown, the imaging lumen 320 is located along a sidewall of the speculum 300 such that the instrument lumen 310 can have larger dimensions and more usable space. In particular, because the dimensions of an orifice such as an ear canal of a patient is limited (e.g., between about 0.5 cm and about 0.8 cm for adults, and smaller for children), the distal end of the speculum 300, including the instrument lumen 310 and the imaging lumen 320, is constrained to those dimensions. Accordingly, the size of the imaging lumen 320 and/or positioning of the imaging lumen 320 relative to the instrument lumen 310 provides a working channel for receiving an instrument through the speculum 300. Moreover, the imaging lumen 320 is sized to fit the dimensions of an imaging assembly.

In some embodiments, and as shown in FIG. 3A, the optical tip 332 may be located within the speculum such that the imaging lumen 320 does not extend all the way to the tip 340 of the speculum 300 (e.g., does not extend the full length of the speculum 300). Stated otherwise, the distal end of the imaging lumen 320 is disposed a first axial position relative to the longitudinal central axis, and the tip 340 is disposed at a second axial position different than that of the distal end of the imaging lumen 320. The position, depth, and orientation of the imaging lumen 320 are described in more detail below.

Figure 3B:
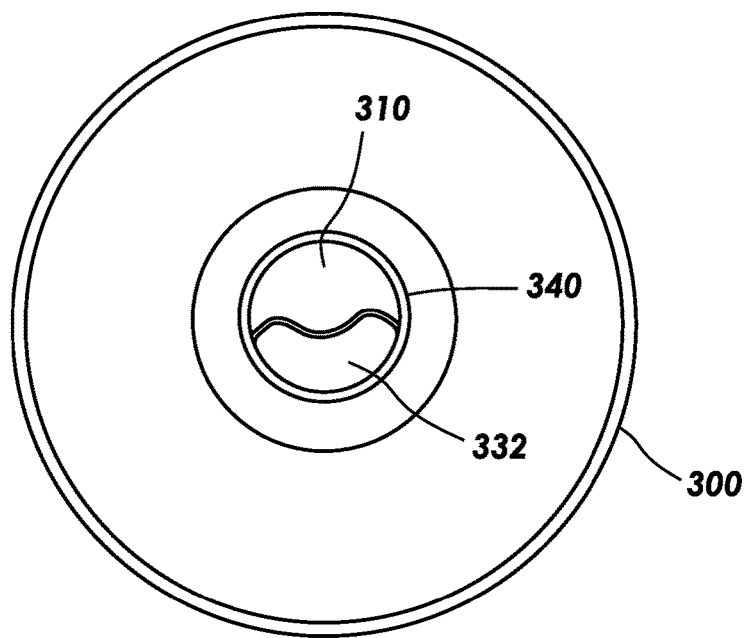
FIG. 3B is a bottom plan view of a speculum in accordance with at least some embodiments.

FIG. 3B is a bottom plan view of the example speculum 300. Visible in FIG. 3B is the tip 340, the optical tip 332, and the instrument lumen 310. In accordance with example embodiments, the axial location of the optical tip 332 is set back from the tip 340 such that, in use, the tip 340 of the speculum is visible to the imaging assembly and thus provides a line-of-sight out of the tip 340.

Figure 4:
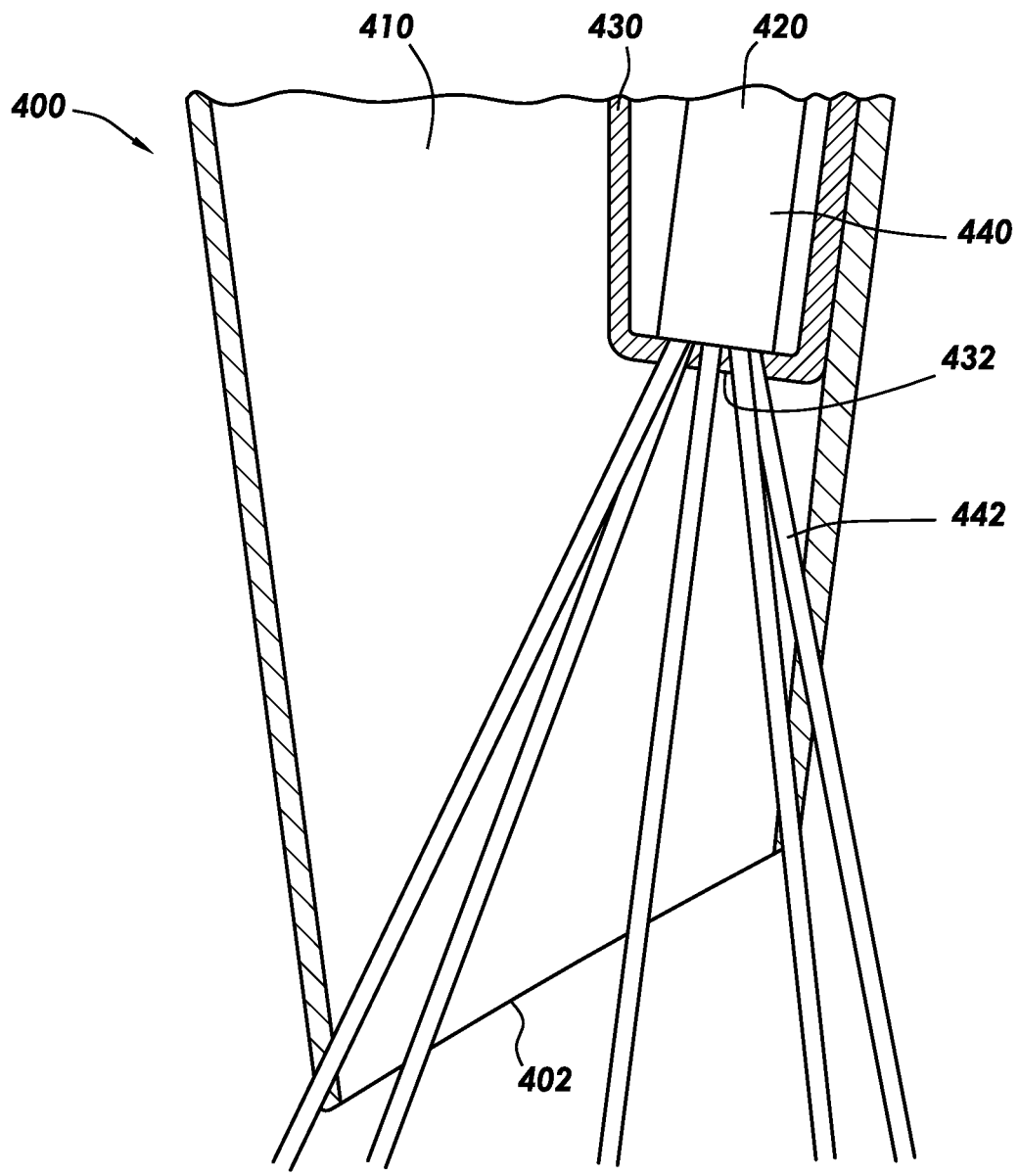
FIG. 4 is a cross-sectional elevation view of a speculum and imaging assembly in accordance with at least some embodiments.

FIG. 4 is an elevation, partial cross-sectional, view of distal end of a speculum 400 with an imaging assembly 440 disposed therein. The speculum 400 may be an example of any of the previously discussed speculums. The example speculum 400 includes an instrument lumen 410 and an imaging lumen 420. The example imaging lumen 420 comprises an optical portion 430 having a lens or optical tip 432. The imaging assembly 440 may be configured to shine illumination 442 (illustratively shown as rays of light) from an end of the imaging assembly 440, through the optical tip 432, and through the tip 402 to illuminate a target treatment area (e.g., a portion of an ear canal adjacent to a tympanic membrane). FIG. 4 shows that, in some cases, the ray path of the illumination 442 may be wider than the inside diameter of the distal end of the speculum 400 at the tip 402. Having the ray path of the illumination 442 wider than the diameter at the tip 402 provides illumination to the inside surface of the speculum 400 at the tip 402 to aid in visualization of the tip 402 by the imaging assembly 440. Thus, though FIG. 4 shows the some rays passing through the outer wall of the speculum, those rays in practice are used to illuminate the inside surface and would not pass through an opaque speculum. Nevertheless, the illumination 442 is configured to illuminate a target treatment area (not shown) outside and beyond the tip 402, and as shown may optionally illuminate portions of the speculum 400 to assist in visualization of the distal end of the instrument during initial insertion into the speculum 400. However, reflectance back into the speculum of the illumination 442 directed to the tip 402 is reduced based on the angle of attack of the illumination 442.

In accordance with some embodiments, the imaging lumen 420 has a length that enables the imaging assembly 440 to telescope into the imaging lumen 420 and contact or abut an inside surface of the optical tip 432. However, due to manufacturing variances, the imaging assembly 440 may not always fit exactly into the imaging lumen 420 such the imaging assembly abuts the inside surface of the optical tip 432. In other cases, to avoid damaging the imaging assembly 440, the length of the imaging lumen 420 and the length of the imaging assembly 440 are designed and constructed such that, when the imaging assembly 440 is fully inserted into the imaging lumen 420, a small gap may exist between the distal end of the imaging assembly 440 and the inside surface of the optical tip 432. However, the gap between the distal end of the imaging assembly 440 and the inside surface of the optical tip 432 may affect quality of image data generated by the imaging assembly 440 because of reflections due to internal and surface refraction of the optical tip 432.

Still referring to FIG. 4, in some embodiments the optical portion 430 of the imaging lumen 420 may include a dome and/or Fresnel features configured to steer light toward the tip 402, and thus reduce light scattering within the speculum. Moreover, in some embodiments, the imaging assembly 440 may include one or more baffles between the optical sensor and illumination source(s) and configured to block light scattering within the optical tip 432.

In embodiments in which the imaging assembly 440 is designed and constructed to abut the inside surface of the optical tip 432, the imaging assembly 440 may include a spring (not shown) configured to apply a force such that the imaging assembly can be biased toward the optical tip 432. For example, an elongate portion of the imaging assembly 440 may include a spring having a predetermined k-value that enables the distal end of the imaging assembly 440 to align and make flush contact with the inside surface of the optical tip 432 without clinician adjustment. In some embodiments, the spring may have a short throw and be configured to reduce a gap between the imaging assembly 440 and optical tip 432 by up to about 0.3 mm.

Additionally or alternatively, an optical gel may be disposed between the imaging assembly 440 and optical tip 432. For example, the optical gel may have a refraction index substantially matched to the optical tip 432 to reduce refraction and reflection (e.g., caused by any air gap). In some embodiments, the speculum 400 may be pre-assembled with an optical gel applied at least to the inside surface of the optical tip 432. The imaging assembly 440 may be inserted into the imaging lumen 420 and optically coupled to the optical tip 432 via the optical gel. In other cases, an optical gel is applied to a distal tip of the imaging assembly 440 prior to being inserted into the imaging lumen 420. When the speculum 400 is separated from the imaging assembly 440 after use, the distal end of the imaging assembly 440 may be cleaned (e.g., wiped down) to remove any remaining gel on the imaging assembly 440.

In cases where a gap exists between the distal end of the imaging assembly 440 and the inside surface of the optical tip, a distance between the distal end of the imaging assembly 440 and an inside surface of the optical tip 432 may be selected to improve image quality while reducing the dimensions of the imaging assembly and speculum. In some embodiments, the illumination 442 output by an illumination source of the imaging assembly 440 may be focused at a center of a target treatment area and away from the inside surface of the speculum 400 in order to reduce reflection. In some embodiments, the side walls of the speculum 400 are formed of a light absorbing material to reduce the amount of reflected light. Moreover, the thickness of the optical tip 432 may be selected to reduce interference (e.g., refraction loss, image blurring, cross-talk) between illumination source(s) and an optical lens of the imaging assembly 440 while having sufficient thickness to be durable and aid in manufacture. For example, the configuration and dimensions of an imaging lumen and imaging assembly may depend on a numerical aperture (NA) of an illumination source and a field of view of an optical lens imaging assembly.

FIG. 5 shows, in block diagram form, considerations regarding placement of an illumination source, an optical sensor, and thickness of the optical tip. In particular, FIG. 5 shows an imaging assembly 500 and an optical tip 530. The imaging assembly 500 comprises a lens system 510 (e.g., camera, optical sensor) and one or more illumination sources 520 (e.g., light and/or optical fiber; single fiber shown for the sake of clarity). The lens system 510 and the illumination source 520 define a center-to-center spacing X. The optical tip 530 defines a thickness T. The lens system 510 and the illumination source 520 define a gap or separation from the inside surface of the optical tip 530, the separation shown as distance D. The distance D may be given by Equation (1):

$$D = \frac{X - (X_2 + X_3 + C_r + F_r)}{\tan(\alpha_1) + \tan(\beta_1)}. \quad (1)$$

where $C_r$ is the radius of the exposed portion of the lens system entrance element, $F_r$ is the radius of the illumination source, $\alpha_1$ is half of an acceptance angle of the illumination source 520 by the optical tip, and $\beta_1$ is half of a viewing angle (semi-field of view (SFOV)) of the lens system.

The remaining parameters of Equation (1) may be given by the following equations:

$$\alpha_2 = a\sin\left(\frac{\sin(\alpha_1)}{n_{ac}}\right) \quad (2)$$

where $n_{ac}$ is the refractive index of the light exit port material of the illumination source (e.g., optical tip material), $$\beta_2 = a\sin\left(\frac{\sin(\beta_1)}{n_{ac}}\right) \quad (3)$$

$$X_1(D) = D \cdot \tan(\alpha_1) \quad (4)$$

$$X_2 = T \cdot \tan(\alpha_2) \quad (5)$$

$$X_3 = T \cdot \tan(\beta_2) \quad (6)$$

$$X_4(D) = D \cdot \tan(\beta_1). \quad (7)$$

In an example case in which the optical tip is composed of acrylic with a numerical aperture of 0.51, the optical window has a thickness T of 0.5 mm, the optical sensor has a field of view of 50 degrees, and a distance X of about 1.5 mm, then the imaging assembly 500 can be designed to have a maximum distance D of about 0.09 mm to reduce or prevent reflection. In some embodiments, the optical tip 530 may be composed of a material having a low refractive index, such as polycarbonate and acrylic. For example, polycarbonate may be injection molded and may be ultrasonically welded to form the speculum.

FIGS. 6A and 6B show side elevation views of two example speculums. In particular, the tips of the speculums may be configured to enable an instrument to pass into an orifice of a patient, such as an ear canal, and also enable a view of the target treatment area and/or instrument (e.g., located near the target treatment area). The first speculum 600 has a symmetric tip 610. That is, a longitudinal central axis of the speculum 600 is orthogonal to a plane defined by the tip 610. The second speculum 620 has a beveled tip 630. That is, a longitudinal central axis of the speculum 620 is not orthogonal to, and rather forms a non-right angle to, a plane defined by the tip 630. The tip 630 of speculum 620 may improve instrument access to an ear canal (e.g., increase a range of motion of an instrument) and may increase a field of view of an imaging assembly disposed within the speculum. In particular, because the imaging lumen and imaging assembly are biased to one side of the speculum, the beveled tip 630 reduces the amount of the interior of the speculum visible to the imaging assembly, thus increasing amount of light that reaches the tympanic membrane and the number of pixels used to image the tympanic membrane. In some embodiments, the tip 630 form an angle of less than about 30 degrees relative to a plane orthogonal to the longitudinal central axis.

In some embodiments, the tip of the speculum may be atraumatic. For example, the tip may be formed of a silicone material or may include thermoplastic elastomer over-molding. In some embodiments, the speculum can be a Size 4 speculum with an inner diameter of the tip between about 4 mm and about 4.2 mm, inclusive. A size 4 speculum enables accommodation of an instrument having an outer diameter of about 3.5 mm. While a Size 4 speculum is contemplated, the size of the speculum can vary (e.g., ranging from children to adults). Example speculums can also include Size 5 speculums (e.g., an inner diameter of the tip between about 5 mm and about 5.2 mm, inclusive), Size 6 speculums (e.g., an inner diameter between about 6 mm and about 6.2 mmm, inclusive), and all ranges and sub-values in-between.

Figure 7:
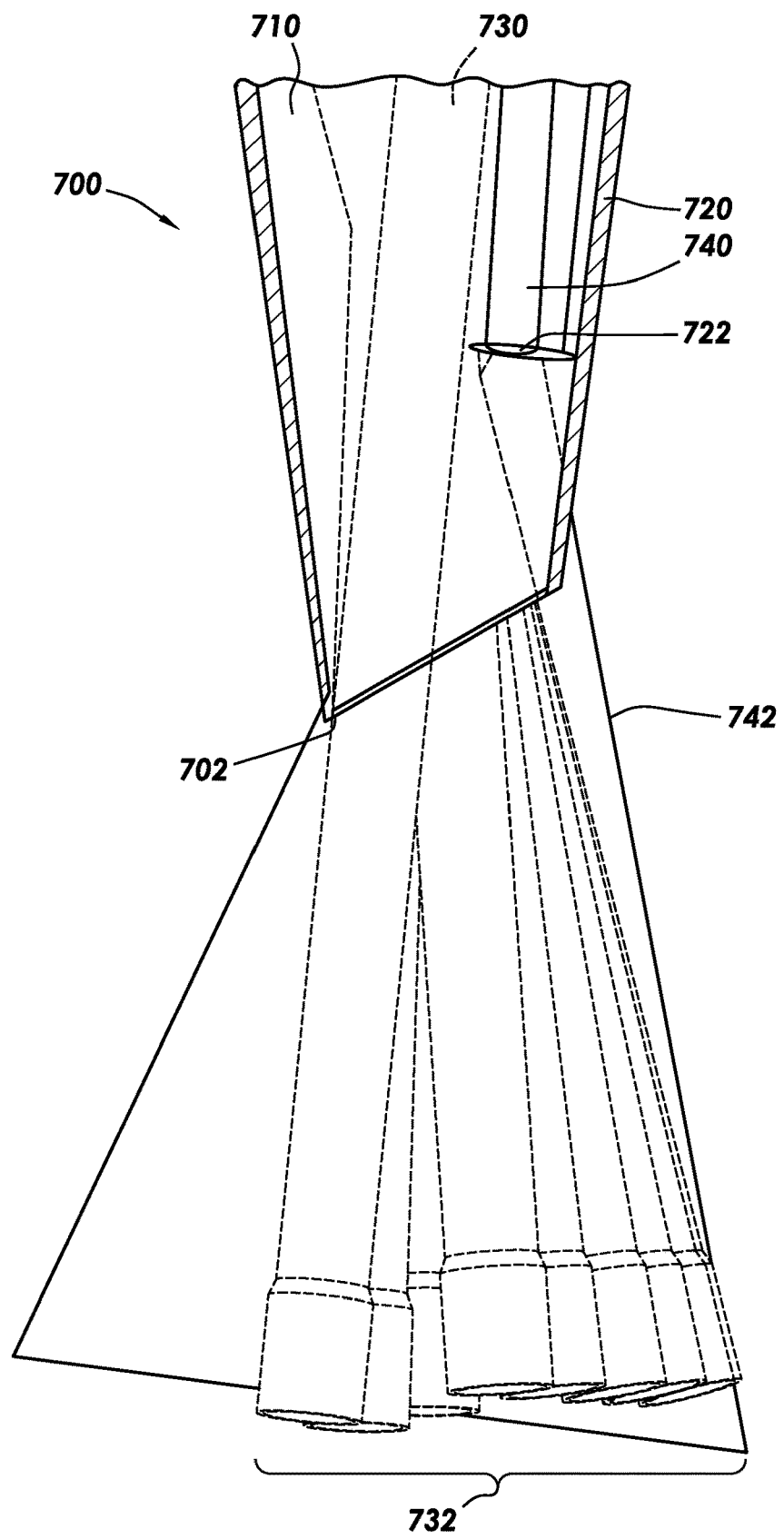
FIG. 7 shows a cross-sectional view of a speculum with an instrument extending through the speculum to illustrate range of motion of the instrument, in accordance with at least some embodiments.

FIG. 7 shows a cross-sectional view of a speculum with an instrument extending through the speculum to illustrate range of motion of the instrument. In particular, FIG. 7 shows a speculum 700 and an instrument 730 extending through the speculum 700. The instrument 730 is shown in multiple positions to illustrate a range of motion 732 of a distal tip of the instrument 730. In one example case, the instrument 730 is a tympanostomy tube delivery system. The example speculum 700 includes an instrument lumen 710, and disposed within the instrument lumen 720 is an example imaging assembly 740, with a distal end of the imaging assembly 740 abutting an optical tip 722. The imaging assembly 740 may be configured to generate image data from a field of view 742 sufficient to visualize a target treatment area (e.g., tympanic membrane).

The field of view 742 is shown to overlap the distal end of the speculum 700. In example embodiments, the outer wall of the speculum 700 is opaque, and thus the imaging assembly 740 will not be able to "see through" the speculum 700. Rather, FIG. 7 illustrates that, in example embodiments, the field of view 742 includes the ability to visualize the tip 702, which is why the example field view 742 overlaps the outer wall of the speculum 700. Though not specifically shown in FIG. 7, the breadth of the effective field of view at the target treatment site will be smaller than the field of view 742 illustrated in FIG. 7.

The field of view 742 of the imaging assembly 740 and range of motion 732 of the instrument 730 depend on the inner dimensions of the speculum 700, axial location and size of the imaging lumen 720, angle of the speculum tip 702, and imaging properties of the imaging assembly 740. In the example shown in FIG. 7, the instrument 730 does not have range of motional as wide as the field of view 742. The relationship between imaging assembly location and optical imaging properties are described in more detail below.

Figure 8:
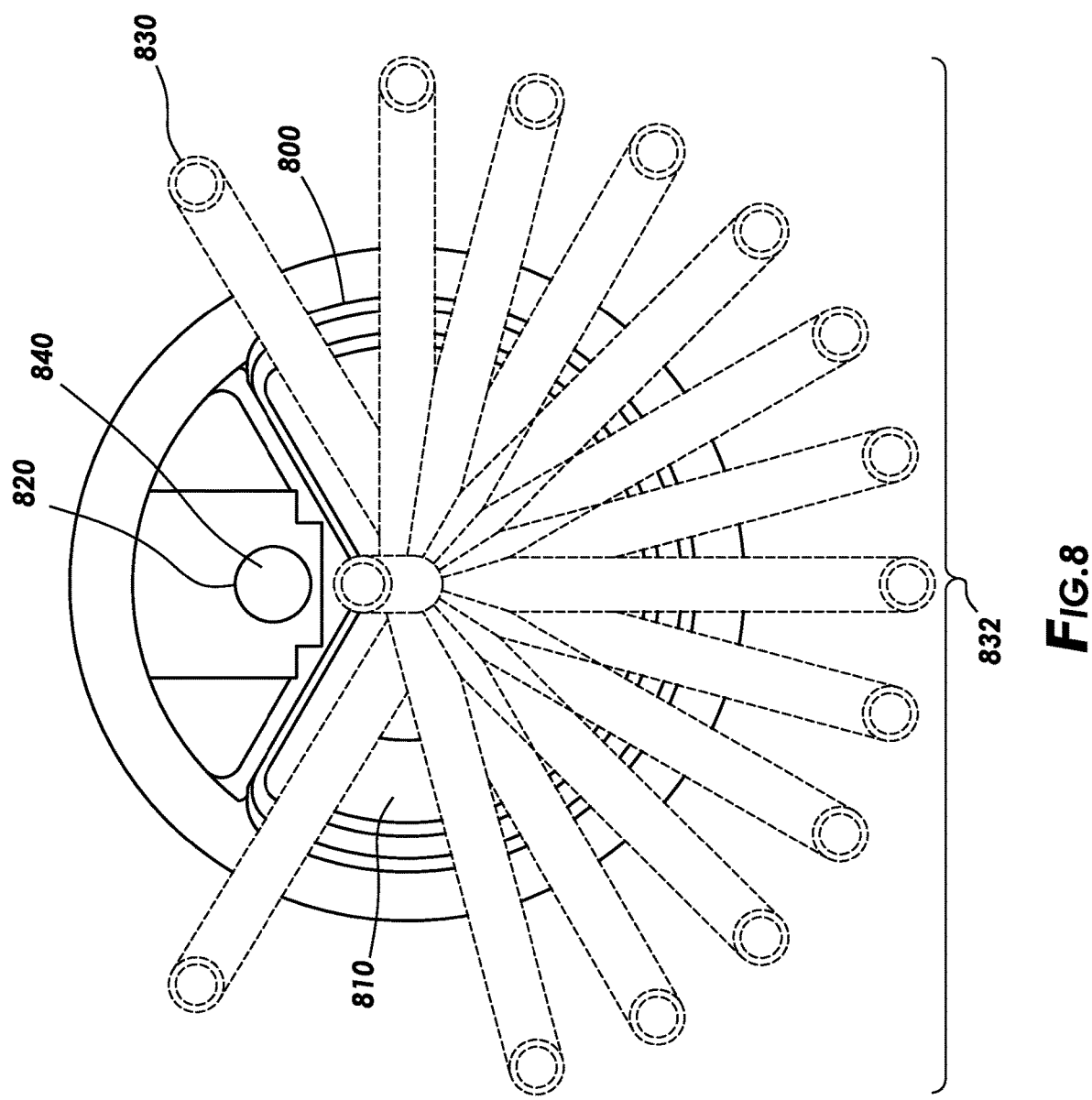
FIG. 8 is an overhead view of a speculum with an instrument extending through the speculum to illustrate range of motion of the instrument at the proximal end to result in the range of motion at the distal end, in accordance with at least some embodiments.

FIG. 8 is an overhead, partial cross-sectional, view of a speculum with an instrument extending through the speculum to illustrate range of motion of the instrument at the proximal end of the speculum. In particular, visible in FIG. 8 is a speculum 800 and an instrument 830. The speculum 800 includes the instrument lumen 810 configured to accommodate advancement and manipulation of the instrument 830. In the partial cross-sectional view, also shown is an imaging lumen 820 and an imaging assembly 840. The instrument 830 is shown in multiple positions to illustrate a range of motion 832 of the instrument 830 once advanced through the speculum 800. The range of motion 832 of the instrument 830 may depend on the dimensions of the speculum 800, and/or position and size of the imaging lumen 820. In the example system, the instrument 830 does not have a full 360-degree range of motion since the imaging lumen 820 and imaging assembly 840 impede the instrument 830 along a portion of the full 360 degrees.

Figure 9:
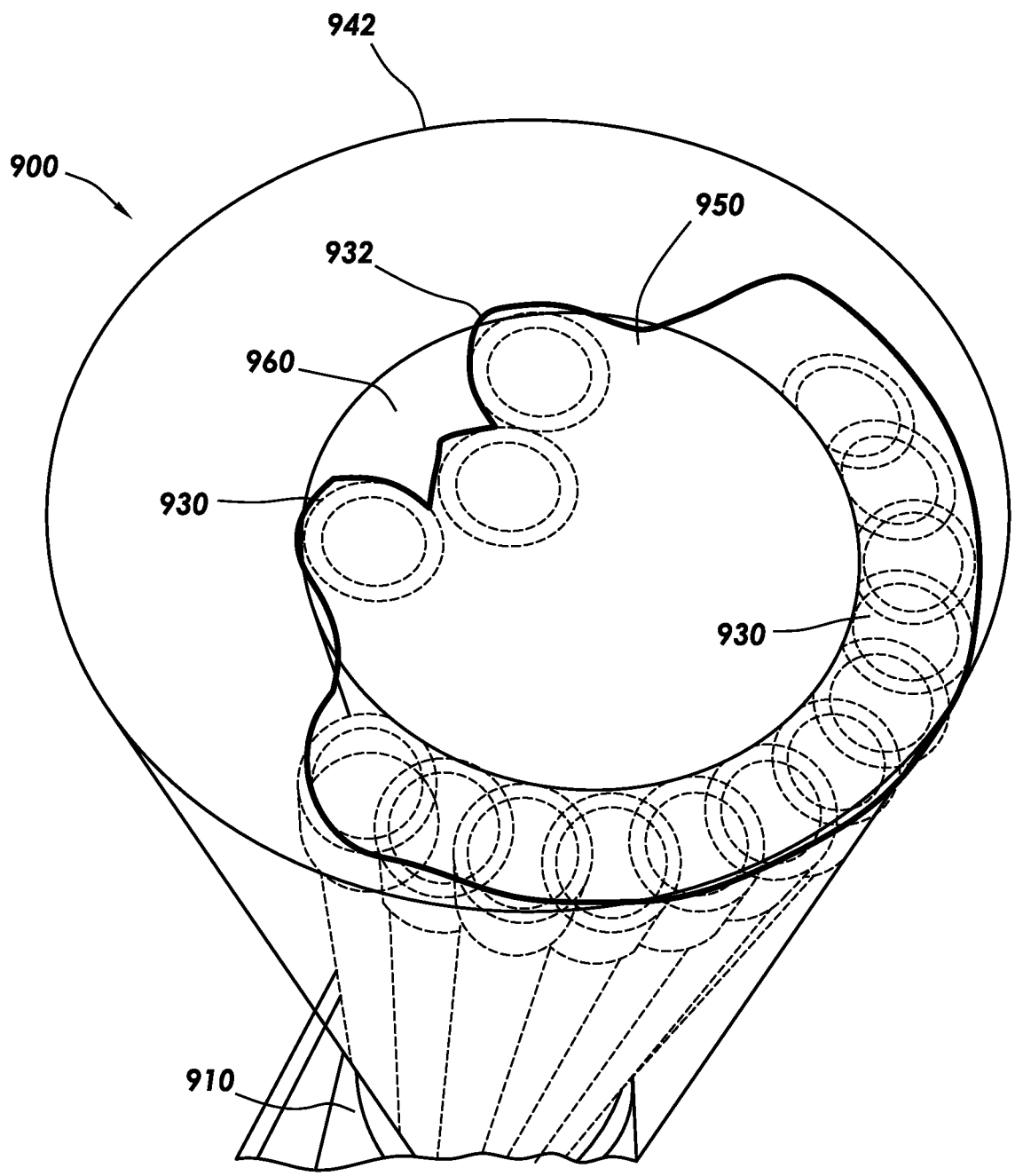
FIG. 9 is a perspective view that shows a relationship of an imaging field of view and a range of motion of an instrument, in accordance with at least some embodiments.

FIG. 9 is a perspective view that shows a relationship of an imaging field of view and a range of motion of an instrument. In particular, FIG. 9 shows a distal end of an instrument 930 after insertion through a speculum 400, and also shows an imaging field of view 942 relative to the speculum 910 and instrument 930. The imaging field of view 942 overlaps an example target treatment area 950 (e.g., the target treatment area 950 having a diameter of between about 9 mm and about 10 mm). The target treatment area 950 may be a tympanic membrane of an ear (shown as a flat plane orthogonal to the speculum central axis for the sake of clarity). For example, the speculum 910 may be directly aligned over a center of the target treatment area 950. In the example shown, the imaging field of view 942 encompasses an entirety of the target treatment area 950 but is offset from the target treatment area 950 (i.e., not concentric with respect to the target treatment area 950) due to the placement of the imaging assembly along a sidewall of the speculum 910. In example embodiments, it is desirable to increase an overlap between the imaging field of view 942 and an area covering a range of instrument motion such that the instrument 930 can reach a larger visible portion of the target treatment area 950.

The visualization system 900 may be configured to enable the instrument 930 to interact with any portion of a target treatment area 950 with limited repositioning (e.g., rotation, translation, etc.) of the speculum 910. The example instrument 930 may be advanced through the speculum 910 and may be manipulated through the speculum 910 to have the range of motion 932. In the example shown, the range of motion 932 of the instrument 930 is not circular due to the geometric constraints of the speculum 910 and the instrument lumen (not shown), such as the space within the speculum 910 occupied by the imaging lumen. The range of motion 932 of the instrument 930 covers, for example, about 90% of the target treatment area 950 with the remaining portion of the target treatment area 950 defining a coverage gap 960. In some embodiments, rotation of the speculum 910 (e.g., by about 20 degrees) modifies the range of motion 932 of the instrument 930 so as to overlap the coverage gap 960 and provides an operator access to the entire target treatment area 950. Accordingly, in some embodiments, the visualization system 900 enables rotation of the speculum 910 and/or imaging assembly. Additionally or alternatively, the speculum 910 may be manipulated (e.g., tilt, pivot, advance, retract, moved laterally) to modify the range of motion 932 of the instrument 930 relative to the target treatment area 950.

Example visualization systems may include the imaging assembly disposable at a predetermined depth, position, and angle relative to a distal end or tip of the speculum in order to increase visualization of a procedure. Consider that, when positioned at a speculum tip, an imaging assembly may be unable to visualize an instrument until the instrument extends beyond the speculum tip. Accordingly, by having the imaging assembly disposed proximal to the speculum tip, the imaging assembly may visualize an instrument as it advances out of the speculum tip toward the target treatment area. This visualization capability may increase a clinician's spatial awareness and depth perception, and thereby improve patient safety and patient outcomes.

FIGS. 10A and 10B are cross-sectional views of speculums to show considerations regarding placement of the imaging lumens relative to the speculum tip and field of view. Referring first to FIG. 10A, FIG. 10A shows a speculum 1000 having an instrument lumen 1010, an imaging lumen 1020, and an imaging assembly 1040 disposed within the imaging lumen 1020. The example imaging lumen 1020 has a distal end that is disposed proximal from the tip 1001 by a first setback distance 1030. The setback distance may be measured as a distance along an optical axis 1051 of the imaging assembly from the distal end of the imaging lumen 1020 to a line that intersects the intersection of the field of view and the internal wall of the speculum at or near the distal-most point of the tip 1001, and the line is perpendicular to the optical axis 1051. Stated differently, the example imaging lumen 1020 has a distal end that is disposed at a first axial position along the longitudinal axis of the 1050, and the distal tip 1001 is disposed at a second axial position along the longitudinal axis 1050, and in the view of FIG. 10A the difference in axial position (e.g., the setback) is about 9 mm. The imaging assembly 1040 generates image data having a first field of view 1042 and a target depth of focus 1060.

Similarly, FIG. 10B shows a speculum 1002 having an instrument lumen 1012, an imaging lumen 1024, and an imaging assembly 1044 disposed within the imaging lumen 1024. The example imaging lumen 1024 has a distal end that is disposed proximal to the tip 1003 by a second setback distance 1032 (e.g., 13 mm, being greater than the setback distance 1030 of FIG. 10A), and the setback distance 1032 measured along the optical axis 1053 equivalently to setback distance 1030. Stated differently, the example imaging lumen 1024 has a distal end that is disposed at a first axial position along the longitudinal axis of the 1052, and the distal tip 1003 is disposed at a second axial position along the longitudinal axis 1050, and in the view of FIG. 10B the difference in axial position (e.g., the setback) is about 13 mm. The imaging assembly 1044 generates image data having a second field of view 1046 and a target depth of focus 1062.

In example systems, the first setback distance 1030 may be about 9 mm and the second setback distance 1032 may be about 13 mm. The first field of view 1042 may be about 36.8 angular degrees and the second field of view 1046 may be about 25.5 angular degrees. Accordingly, as setback distance between a speculum tip and a distal end of the imaging assembly increases, an effective field of view of the visualization system decreases (e.g., due to a size of the opening at the speculum tip).

In some embodiments, the imaging assembly may have a resolution of between about 15 micro-meters ($\mu$m) and about 120 $\mu$m depending on the distance of the object visualized from the imaging assembly. Consider, as an example, that the imaging assembly 1040 has a depth of focus (DOF) of between about 9 mm and about 28 mm, inclusive. A far field focus of about 28 mm, measured from a distal end of the imaging assembly 1040 along the optical axis 1051, puts the far field focus at about 19 mm away from the speculum tip 1001. From about 9 mm to about 20 mm from the distal end of the imaging assembly 1040, the focus resolution is less than the resolution at the target depth of focus 1060; however, the reduced resolution in the range of 9 mm to about 20 mm may be at least about 150 $\mu$m such that objects can be identified and visualized even if fine details are not fully visible. As the design of a speculum further sets back the imaging assembly, the target depth of focus relative to the speculum tip may decrease. For example, in the embodiment depicted in FIG. 10B with a 13 mm setback distance, the depth of focus of the imaging assembly 1044 can be between about 13 mm to about 32 mm, with a target depth of focus 1062 being between about 24 mm to about 32 mm, inclusive. For other camera systems (e.g., camera sensors disposed at the distal tip of the imaging assembly), the camera sensor may have a depth of focus between 0 and 50 mm, in which case the setback distance is controlled largely by the desired range of motion.

i. Setback and Field of View

In accordance with example embodiments, the setback distance between the speculum tip and the distal end of the imaging lumen (measured along the optical axis) may be between about 4 mm and about 24 mm, inclusive. The setback distance controls the effective field of view of the imaging assembly, where the internal edge of the aperture of the speculum tip, in some embodiments, is within the field of view. In an example embodiment, a setback distance of about 8 mm corresponds to an effective field of view of about 40 degrees and, and a setback distance of 24 mm corresponds to an effective field of view of about 12 degrees.

FIGS. 10A and 10B also illustrate a tradeoff or balancing of considerations at the design stage of the speculum and related imaging assembly. In particular, in the example of FIG. 10A the field of view 1042 is an example 36.80 angular degrees. At an example setback distance 1030 of 9 mm and an example depth of focus of 16 mm from the distal tip 1001 a point within the depth of focus 1060, a tympanic membrane (e.g., 10 mm in diameter) occupies a particular amount (less than the entire) field of view at the depth of focus. On the other hand, in the example of FIG. 10B the field of view 1046 is an example 25.53 angular degrees. At the example setback distance 1032 of 13 mm and the example depth of focus, a tympanic membrane (e.g., 10 mm in diameter) occupies less than the entire field of view at the depth of focus, but occupies more of the field of view than the FIG. 10A. It follows that, in the case of FIG. 10B, more pixels of an image are dedicated to imaging the tympanic membrane than for the case of FIG. 10A. Stated differently, the resolution of an image of the tympanic membrane in FIG. 10B will be greater than the resolution of the image of the tympanic membrane in FIG. 10A for equal size tympanic membranes. In some example cases, a tympanic membrane residing at the depth of focus (e.g., 1060, 1062) occupies at least 50% of the visible area at the depth of focus, in some cases at least 60% of the visible area at the depth of focus, and in other cases at least 80% of the visible area at the depth of focus.

ii. Optical Axis Angle

Given the inverted frustum shape of the example speculums, the optical axis of the imaging assembly may be angled relative to the speculum longitudinal axis, with the magnitude of the angle based on the setback distance. For example, the first speculum 1000 defines a first longitudinal axis 1050, and a setback distance 1030 of about 9 mm results in a tilt angle of about 7.5 degrees measured between the longitudinal axis 1050 and the optical axis 1051. As the setback distance of a design increases, the tilt angle between the longitudinal axis of the speculum and the optical axis also increases. Stated otherwise, the optical axis 1051 may also be defined solely in terms of the imaging lumen 1020. For example, the optical axis 1051 may be equivalently defined as a line perpendicular to the optical window at the distal end of the imaging lumen 1020, and in some cases the line perpendicular to the optical window is parallel to a line tangent to the inside surface of the speculum at the distal end of the imaging lumen. Nevertheless, the tilt angle between the optical axis (however defined) and the longitudinal axis may increase as the design of the speculum has increased setback distance.

Figure 28A:
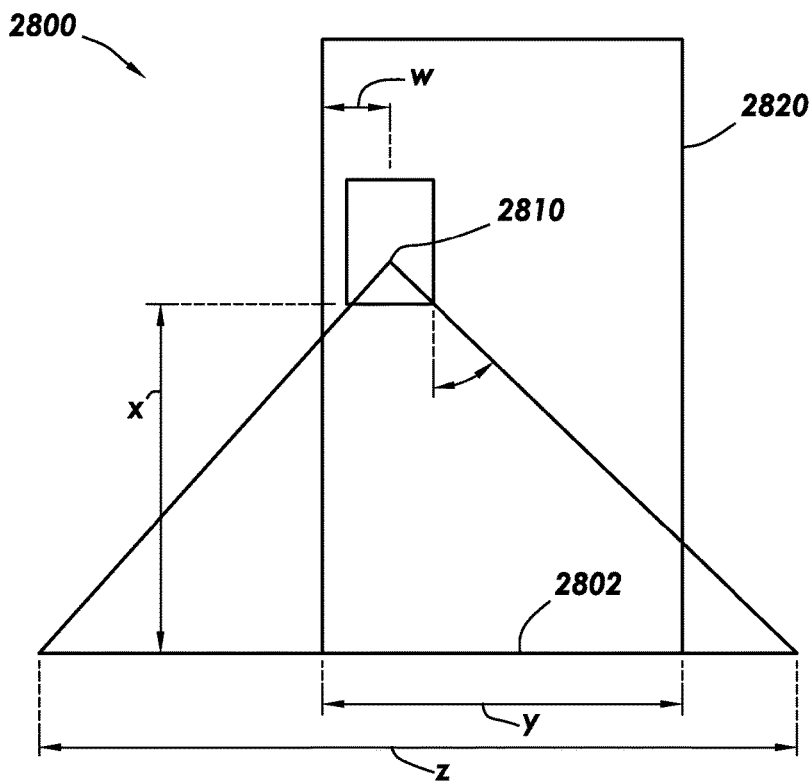
FIG. 28A shows a block diagram of various relationships of a visualization system, in accordance with at least some embodiments.
Figure 28B:
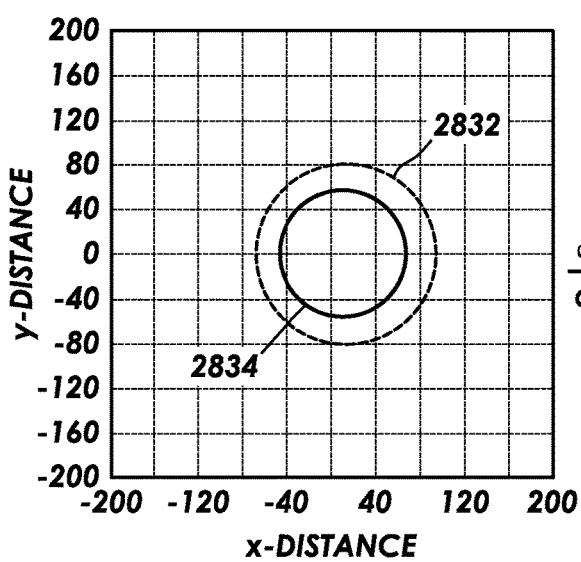
FIG. 28B is a plot showing a relationship of fields of view of two types of optical sensors, in accordance with at least some embodiments.
Figure 28C:
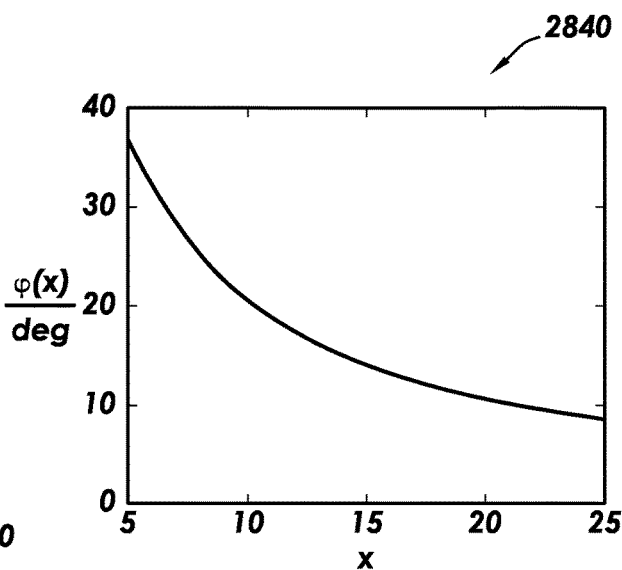
FIG. 28C is a plot showing a relationship of tilt angle ($\varphi$) as a function of distance to a center field of view, in accordance with at least some embodiments.

In accordance with example embodiments, a speculum is designed and constructed to compensate for the fact that the imaging lumen is offset from the longitudinal axis, the compensation in the form of the tilt angle. That is, during design of a speculum the tilt angle is selected such that the optical axis intersects the longitudinal axis of the speculum near or within the target treatment area. Stated otherwise, during design of a speculum the tilt angle is selected such that the optical axis intersects the longitudinal axis of the speculum at the designed the depth of focus of the imaging assembly. FIGS. 28A-28C show relationships of tilt angle of an optical axis and a target treatment area with respect to the imaging assembly's field of view.

FIG. 28A shows a block diagram of various relationships of an example visualization system 2800. In particular, FIG. 28A shows a camera or optical sensor 2810 disposed within an ear canal 2820. The optical sensor 2810 may be a predetermined distance X from a target treatment area 2802 (e.g., a tympanic membrane) having a diameter Y. And the optical sensor 2810 is disposed a distance W from a sidewall of the example ear canal 2820. The example optical sensor 2810 has a field of view with a diameter Z centered about the optical axis of the optical sensor 2810. In one example embodiment, the distance X can be 16 mm, the diameter Y can be 9 mm, and a distance W can be 0.75 mm.

In the example situation of FIG. 28A, the optical axis of the optical sensor does not intersect the center of the target treatment area 2802. In order to have the optical axis of the optical sensor 2810 intersect, or pass within a predetermined distance from, the center of the target treatment area 2802, the optical axis of the optical sensor 2810 needs to be placed at a tilt angle (e.g., relative to a longitudinal axis of a speculum, not shown).

FIG. 28B is a plot showing a relationship of fields of view of two types of optical sensors that may be disposed within an imaging assembly of the various embodiments. The Y axis of FIG. 28B is distance from zero in a first direction, with zero centered along the axis. The X axis of FIG. 28B is distance from zero in a second direction orthogonal to the first direction, with zero centered along the axis. In particular, FIG. 28B of viewing areas 2832 and 2834 (at a uniform distance) for two types of optical sensors. Specifically, an optical sensor implemented as a cube camera may have a viewing area 2832 as shown, and an optical sensor implemented as a round camera may have a viewing area 2834. The difference in viewing area may be attributable to the half-viewing angle of each optical sensor type. The example round camera may have a half-viewing angle of 35 angular degrees and the cube optical sensor may have a half-viewing angle of 45 angular degrees.

FIG. 28C is a plot showing a relationship of tilt angle ($\varphi$) as a function of distance to a center of a field of view, in accordance with at least some embodiments. The Y axis of FIG. 28C shows tilt angle ($\varphi$) in angular degrees (e.g., tilt angle of an optical axis relative to a longitudinal axis of a speculum). The X axis of FIG. 28C shows distance from the optical sensor to the target treatment area (e.g., distance X of FIG. 28A). In particular, the plot of FIG. 28C shows an example relationship between tilt angle ($\varphi$) and distance X to center a field of view of the optical sensor. Stated otherwise, the plot of FIG. 28C shows a relationship between tilt angle ($\varphi$) and distance X that may be used to have the optical axis of the optical sensor intersect, or pass within a predetermined distance of, the center of the target treatment area. For example, FIG. 28C shows that the tilt angle ($\varphi$) of the optical sensor increases as the distance X between the optical sensor and a target treatment area decreases. Stated in terms of setback distance of an imaging assembly, and assuming the tilt angle increases with increasing setback distance, FIG. 28C shows that the tilt angle ($\varphi$) of the optical sensor increases as the designed target treatment area moves closer to the speculum tip.

B. Visualization Device

The visualization systems described herein may be coupled to a speculum and enable visualization of an ear canal and tympanic membrane during a procedure using one or more instruments (e.g., a tympanostomy tube delivery device). For example, a scope attached to a speculum may be configured to capture image data while enabling rotation of portions of the scope and/or the speculum. As described with respect to FIG. 1, the visualization system 100 may include an imaging assembly, speculum attachment mechanism, image rotation assembly, and wire management system, all described in greater detail below, starting with the imaging assembly.

i. Imaging Assembly

An example imaging assembly may include sensors (e.g., optical sensors such as, for example, a camera, serializers) and illumination sources (e.g., a light emitters and/or light guide). The imaging assembly may comprise an elongate portion configured to position various components of the imaging assembly within an imaging lumen of a speculum such that those components can image a target treatment area (e.g., tympanic membrane). For example, the elongate portion can be a shaft or arm that comprises a housing configured to support and/or enclose at least a portion of an optical sensor and an illumination source.

Figure 11:
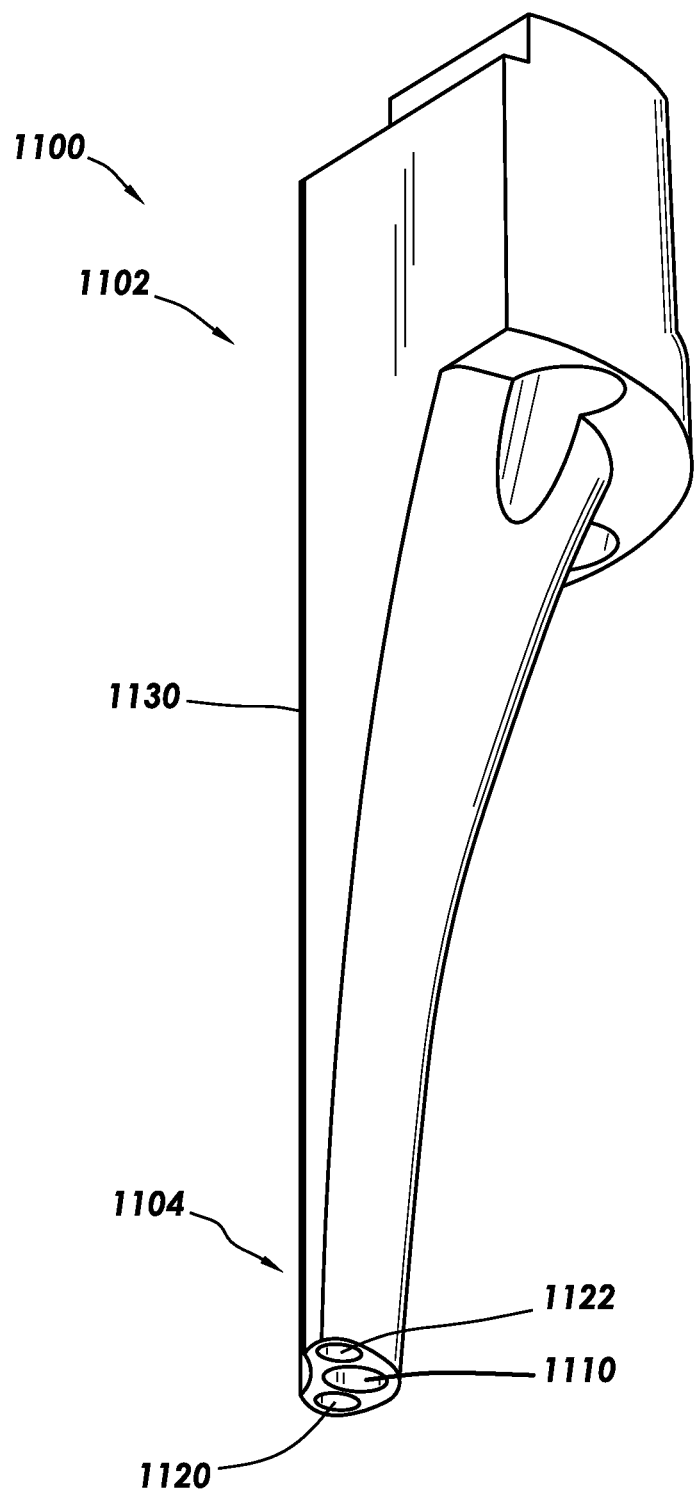
FIG. 11 shows a perspective view of an imaging assembly in accordance with at least some embodiments.

FIG. 11 shows a perspective view of an imaging assembly 1100 in accordance with at least some embodiments. The example imaging assembly 1100 is representative of any of the previously discussed imaging assemblies. The imaging assembly comprises a proximal end 1102, a distal end 1104, and an elongate shaft or elongate portion 1130. The proximal end 1102 of the imaging assembly 1100 is configured to couple to a base of a visualization system (the entire visualization system not shown for clarity). The distal end 1104 of the imaging assembly 1100 is configured to telescope within an imaging lumen of a speculum, and further configured to provide illumination and image sensing within a speculum (e.g., any of the example speculums previously discussed). Thus, the elongate portion 1130 is designed and constructed to fit within an imaging lumen of a speculum. In some embodiments, the elongate portion can be a sealed enclosure configured to enable routine cleaning and maintenance of the imaging assembly.

The example imaging assembly 1100 comprises a distal optical lens 1110 disposed on a distal face of the elongate shaft. The distal optical lens 1110 is operatively disposed between a first illumination source 1120 and a second illumination source 1122. In some embodiments, an optical sensor (not specifically shown) may physically reside at the distal end of the imaging assembly; however, in other embodiments the optical sensor may reside proximally within the elongate portion 1130 of the imaging assembly 1100 and be optically coupled to the distal optical lens 1110 by way of a rod lens system (not specifically shown in FIG. 11, but discussed in greater detail below).

Figure 12A:
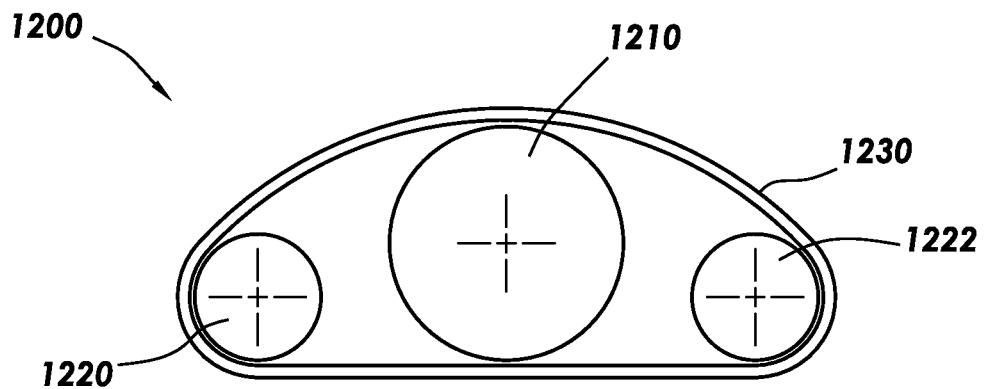
FIG. 12A is a bottom plan view of an imaging assembly with an optical sensor in the form of a round camera, in accordance with at least some embodiments.

FIG. 12A is a bottom plan view of an imaging assembly with a distal optical lens suitable for an optical sensor in the form of a round camera, in accordance with at least some embodiments. The example imaging assembly 1200 comprises a housing 1230 enclosing a distal optical lens 1210 disposed between a first illumination source 1220 and a second illumination source 1222. In the example system, the center-to-center spacing between the first illumination source 1220 and the second illumination source 1222 is about 2.92 mm. The thickness of the overall imaging assembly 1200 (measured at the apex of the curved surface to the flat bottom) in the example system may be about 1.6 mm. The distal optical lens 1210 is illustrative shown as a round to accommodate a round camera with a circular cross-sectional shape (the cross-section for the shape taken in the plane of page of FIG. 12A). The imaging assembly 1200 is designed and constructed to telescope with an imaging lumen of a speculum and be disposed in operational relationship to a lens or window that defines the distal end of an imaging lumen of a speculum.

Figure 12B:
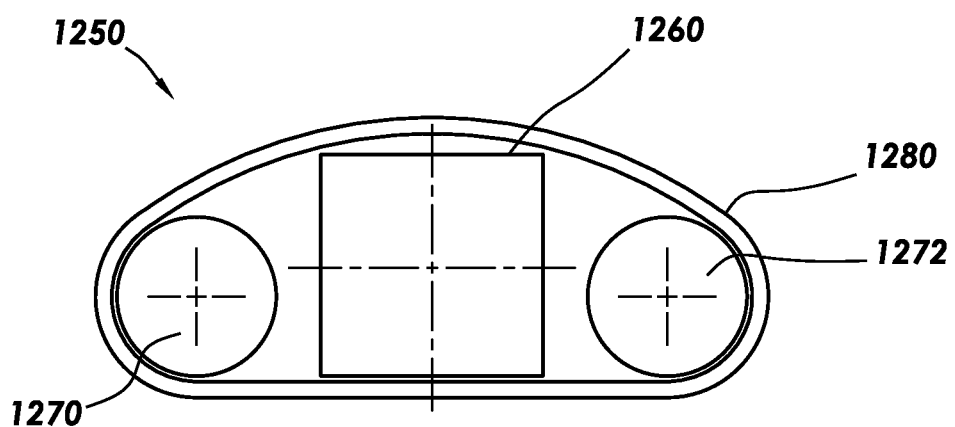
FIG. 12B is a bottom plan view of an imaging assembly with an optical sensor in the form of a cube camera, in accordance with at least some embodiments.

FIG. 12B is a bottom plan view of an imaging assembly with a distal optical lens suitable for an optical sensor in the form of a cube camera, in accordance with at least some embodiments. The example imaging assembly 1250 comprises a housing 1280 enclosing a distal optical lens 1260 disposed between a first illumination source 1270 and a second illumination source 1272. In the example system, the center-to-center spacing between the first illumination source 1270 and the second illumination source 1272 is about 2.2 mm. The thickness of the overall imaging assembly 1250 (measured at the apex of the curved surface to the flat bottom) in the example system may be about 1.32 mm. The distal optical lens 1260 is illustrative shown as square to accommodate a cube camera with a rectangular cross-sectional shape (the cross-section for the shape taken in the plane of page of FIG. 12B). The imaging assembly 1250 is designed and constructed to telescope with an imaging lumen of a speculum and be disposed in operational relationship to a lens or window that defines the distal end of an imaging lumen of a speculum.

The optical sensor, round or cube, may take any suitable form. For example, the optical sensor may comprise a photodiode, charged coupled device (CCD), or complementary metal-oxide semiconductor (CMOS) optical sensor, and in some cases an optical lens assembly. In some embodiments, the optical sensor may have a resolution of between about 1 megapixel and about 5 megapixels, inclusive. The optical sensor may have a pixel size of between about 1.12 µm and about 2 µm, inclusive. The optical sensor may have a sensor image area of between about 6 mm$^2$ and about 12 mm$^2$, inclusive. The optical sensor may have a sensitivity of between about 600 mV/Lux-sec and about 700 mV/Lux-sec, inclusive. The optical sensor may have a chief ray angle of up to about 29.1 degrees. The optical sensor may have a framerate of up to about 30 frames per second. In some embodiments, the optical sensor may be recessed a distance from a speculum tip of between about 2 mm and about 24 mm, inclusive, and have a focus optimized working distance (e.g., target depth of focus) of between about 11 mm and about 19 mm, inclusive, from the speculum tip corresponding to a focus tolerance of between about +3 mm and about −5 mm, inclusive. The optical sensor may have a detail resolution target of between about 12 µm and about 40 µm, inclusive, across the working distance. In some embodiments, the full depth of focus of the optical system may be between about 2 mm and about 43 mm, and the field of view may be between about 12 degrees and about 50 degrees, inclusive (dependent on the optical system recessed distance from the tip of the speculum and other factors).

Figure 13:
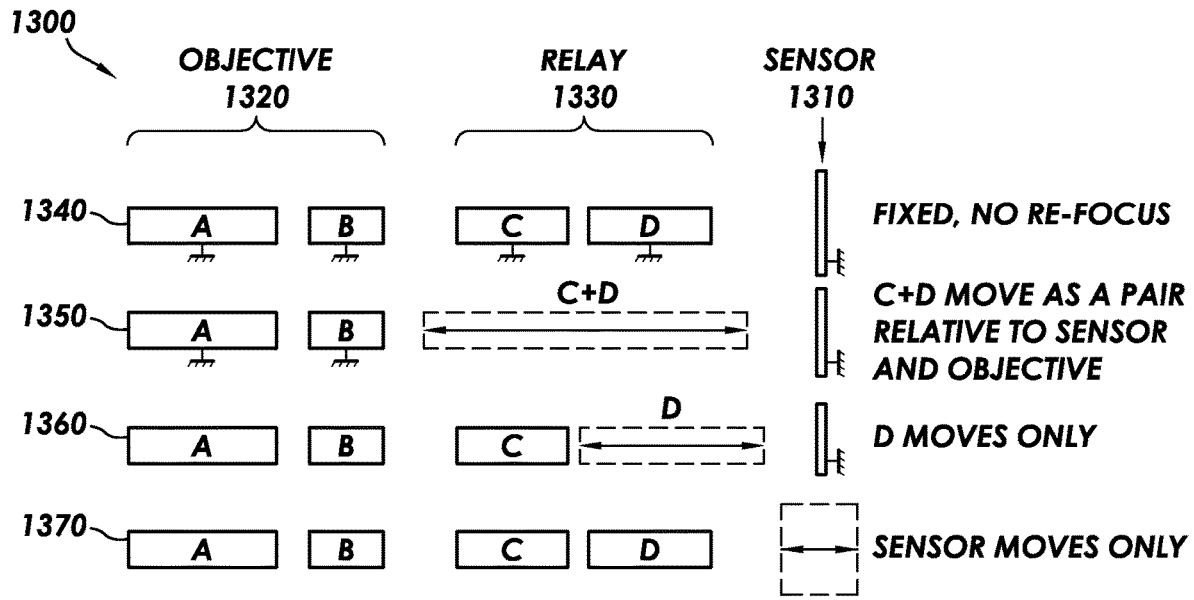
FIG. 13 shows a set of schematic diagrams of optical lens assembly configurations 1300 of an imaging assembly that may include a passive or active focus mechanism, in accordance with at least some embodiments.

FIG. 13 shows a set of schematic diagrams of optical lens assembly configurations 1300 of an imaging assembly that may include a passive or active focus mechanism. In particular, an optical lens assembly may include objective lens elements 1320 and relay lens elements 1330. In some embodiments, the optical lens assembly may include two or more elements (four elements shown for the sake of example). The optical lens assembly may be configured to balance feature resolution and depth of field to accommodate variations in patient anatomy (e.g., ear structure, ear canal shape, ear canal size). For example, focus of an optical lens system may be configured to provide a working distance of about 16 mm with a tolerance of between about +3 mm and about −5 mm for a total working depth of focus of between about 19 mm and 22 mm, inclusive. The resolution across working depth of focus range may vary. For example, an imaging assembly having an optical lens assembly recessed about 9 mm from a speculum tip may have a focus optimized working distance of between about 20 mm and about 28 mm. Resolution may rapidly degrade outside of this working distance range (e.g., in the nearfield direction). The full depth of focus range takes into consideration the recessed distance to the end of the working distance. For example, for an optical lens assembly recessed about 9 mm from the speculum tip, the full depth of focus would be between about 9 mm and about 28 mm. In the nearfield range of the full depth of focus, between about 9 mm and about 20 mm, inclusive, the resolution may be about 150 µm.

In some embodiments, an imaging assembly may include a focus assembly configured to modify a working depth of focus to increase resolution when a desired focus is outside a current working depth of focus range. For example, a working depth of focus may be modified by moving one or more of the optical sensor 1310, objective lens elements 1320, and relay lens elements 1330 relative to each other. The objective lens elements 1320 may comprise a first lens A and a second lens B. The relay lens elements 1330 may comprise a third lens C and a fourth lens D. While FIG. 13 illustrates two objective lens elements 1320 and two relay lens elements 1330, it can be appreciated that any number of objective lens elements and two relay lens elements can be used, including, for example, a single objective lens element and a single relay lens element.

A first focus configuration 1340 may include a set of objective lens elements 1320, a set of relay lens elements 1330, and an optical sensor 1310 that are each fixed relative to each other such that a working depth of focus is set with a fixed range. A second and a third focus configuration 1350, 1360 may comprise a set of relay lens elements 1330 configured to move relative to the set of objective lens elements 1320, and an optical sensor 1310. In the second focus configuration 1350, the third lens C and fourth lens D may move together. In the third focus configuration 1350, at least one of the relay lens elements 1330 (e.g., lens D) may be movable relative to a fixed relay lens (e.g., lens C). A fourth focus configuration 1370 may include an optical sensor 1310 configured to move relative to a fixed set of objective lens elements 1320 and a fixed set of relay lens elements 1330.

In some embodiments, a voice coil mechanism (VCM) and/or elastic membrane mechanism (MEM) may be configured to move at least one of the lens element 1320, 1330 and optical sensor 1310 relative to the other components. In some embodiments, a mechanical actuator (e.g., knob, dial, slider) may enable a clinician to manually modify a focus of the imaging assembly. In some embodiments, the clinician may modify a focus of the imaging assembly using an input device such as a user interface (e.g., including a touch screen, keyboard, display, audio device, etc.) operatively coupled to and/or integrated into the scope.

In some embodiments, each illumination source may comprise a light emitter and/or an optical waveguide. Non-limiting examples of a light emitter include incandescent, electric discharge (e.g., excimer lamp, fluorescent lamp, electrical gas-discharge lamp, plasma lamp, etc.), electroluminescence (e.g., light-emitting diodes, organic light-emitting diodes, laser, etc.), and induction lighting. For example, a light-emitting diode (LED) may be disposed at a proximal end of the imaging assembly and be coupled to an optical waveguide that extends along a length of the imaging assembly. The optical waveguide may receive light from the light emitter having a predetermined combination of light output parameters (e.g., wavelength, frequency, intensity), and convey and transmit that light to an area that is being imaged (e.g., an ear canal). Additionally or alternatively, a distal end of the imaging assembly may directly include a light emitter (e.g., a LED).

An optical waveguide may refer to a physical structure that guides electromagnetic waves, such as visible light spectrum waves, to passively propagate and distribute received electromagnetic waves. Non-limiting examples of optical waveguides include optical fiber, rectangular waveguides, light tubes, light pipes, combinations thereof, or the like. For example, light pipes may include hollow structures with a reflective lining or transparent solids configured to propagate light through total internal reflection. The optical waveguides described herein may be made of any suitable material or combination of materials. For example, in some embodiments, the optical waveguide may be made from optical-grade polycarbonate or glass. In some embodiments, the housings as described herein may be co-injected molded to form the optical waveguides. In other embodiments, the optical waveguides may be formed separately and coupled to a respective housing. In some embodiments, the optical waveguides described herein may include one or more portions configured to emit light through.

In some embodiments, the illumination source may include an optical fiber configured to direct light output through an aperture tip towards a predetermined target treatment area (e.g., a tympanic membrane). That is, given the relative position of the imaging assembly (and therefore the illumination source) relative to the target treatment area and/or a distal aperture of the speculum, the illumination source can be designed and constructed such that light emitted by the optical fiber can be directed at the target treatment area. For example, a tip of a 0.75 mm diameter optical fiber may have an angled tip (e.g., cut angle, bevel) of between about 40 degrees and about 50 degrees, inclusive. The tip of the fiber may be angled relative to a longitudinal axis of a speculum by up to about 0 degrees to about 15 degrees to direct emitted light out of the speculum tip onto a target treatment area. In some embodiments, the light emitted from one or more symmetric illumination sources can be directed on the target treatment area at a nominal working distance range of about 16 mm, with a tolerance of about +3 mm and about −5 mm. The light emitted by the one or more illumination sources can be adjusted, e.g., by angling or shaping the tips of the fibers or by using lensing element(s) molded into the optical tip.

Figure 14:
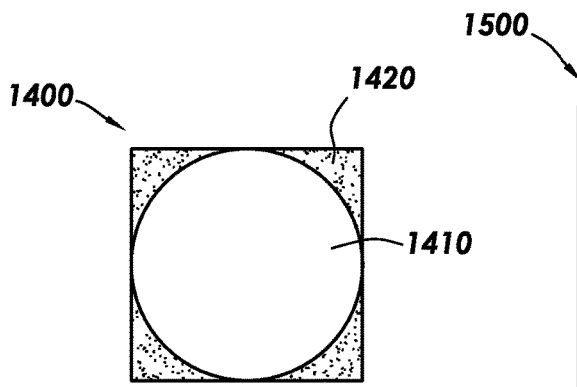
FIG. 14 is a schematic diagram of image data 1400 generated by an imaging assembly of a visualization system, in accordance with at least some embodiments.

FIG. 14 is a schematic diagram of image data 1400 generated by an imaging assembly of a visualization system. The image data 1400 may include a square image corresponding to an image of a target treatment area 1410 and an image 1420 of a portion of a speculum (i.e., the portion of the distal end of the speculum visible in the frames). A lens system of an imaging assembly can map incoming light (e.g., light received from a target treatment area) to an imaging area of an optical sensor, as schematically represented in FIG. 14. By mapping the incoming light to the short dimension of the optical sensor, no image data is cropped or lost before that data is sent to a processor for further post-processing. The size or overall area of the image 1420 of the speculum may increase as the design of the speculum uses greater setback distances. In some of these embodiments, the field of view may be reduced to avoid losing pixels to image cropping. Narrowing the field of view may enable an increase in image resolution due to a higher pixel density over the total area of the image data 1400 (see, e.g., FIGS. 10A, 10B, and related discussion above).

Figure 15:
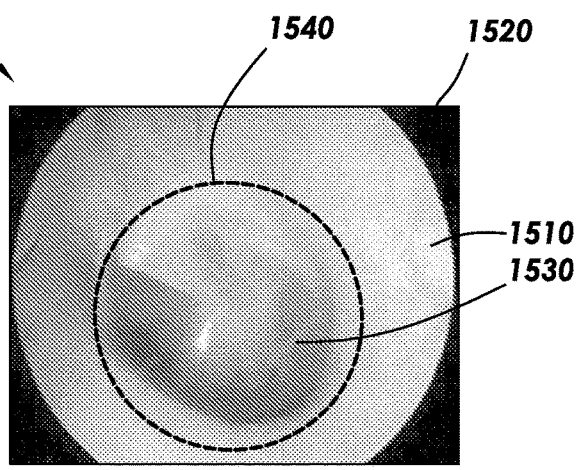
FIG. 15 is an example image of a tympanic membrane and adjacent tissue generated by an imaging assembly of a visualization system, in accordance with at least some embodiments.

FIG. 15 is an example image 1500 of a tympanic membrane 1530 and adjacent tissue 1510 generated by an imaging assembly of a visualization system. The image 1500 depicts a portion of tissue 1510 (e.g., ear canal tissue) adjacent to the tympanic membrane 1530, a target treatment area 1540, and an image 1520 of a speculum (e.g., tip of the speculum). In some cases, the tympanic membrane 1530 may have a diameter of between about 9 mm and about 10 mm. The imaging assembly may be configured to increase illumination and increase resolution within the target treatment area 1540.

ii. Attachment Mechanism

In some embodiments, an attachment mechanism (e.g., attachment mechanism 126) is configured to couple the speculum to the visualization system, which enables a disposable (e.g., single use) speculum to be used with a durable and reusable visualization system. Engagement of an image rotation assembly to the speculum via the attachment mechanism enables the imaging assembly and speculum to rotate about the longitudinal axis of the speculum, the rotation relative to a base of the visualization system.

In example embodiments, the attachment mechanism is configured to provide an attachment interface for the speculum. In some embodiments, the attachment mechanism fixes a longitudinal position of the speculum relative to the base while enabling the speculum to rotate a predetermined number of degrees (e.g., 360 angular degrees) relative to the base and around the longitudinal axis of the speculum via rotation of the image rotation assembly.

In example cases, the attachment mechanism comprises a fastener (e.g., latch, clip, screw, strap) or any other mechanical structure configured to engage a speculum. For example, the attachment mechanism may comprise a spring-loaded latch or an interface with an internal thread. As another example, the speculum may comprise a snap arm configured to engage with a corresponding feature disposed on the image rotation assembly and/or the imaging assembly.

In some embodiments, the attachment mechanism may comprise a release mechanism configured to release the speculum from the visualization system. For example, an operator may actuate a release mechanism that enables manual removal by the clinician or gravity to separate the speculum from the visualization system. In some embodiments, the attachment mechanism may comprise a mechanical attachment mechanism, a pressure-based attachment mechanism, a magnetic attachment mechanism, and/or an electrical attachment mechanism. For example, the attachment mechanism may comprise a magnet configured to attract a corresponding magnet or set of magnets disposed on a speculum. That is, a sidewall of the speculum may comprise a first magnet configured to attract a second magnet disposed within the elongate portion of an imaging assembly. In some embodiments, the magnetic engagement may form a rotational coupling between the speculum and rotation mechanism.

In some embodiments, the attachment mechanism may comprise an iris mechanism configured to transition from a closed configuration to an open configuration based upon a position of an actuator. The iris mechanism may include a set of elongate portions configured to hold or release a speculum to/from a visualization system. The following discussion and figures provide examples of attachment mechanisms.

Figure 31A:
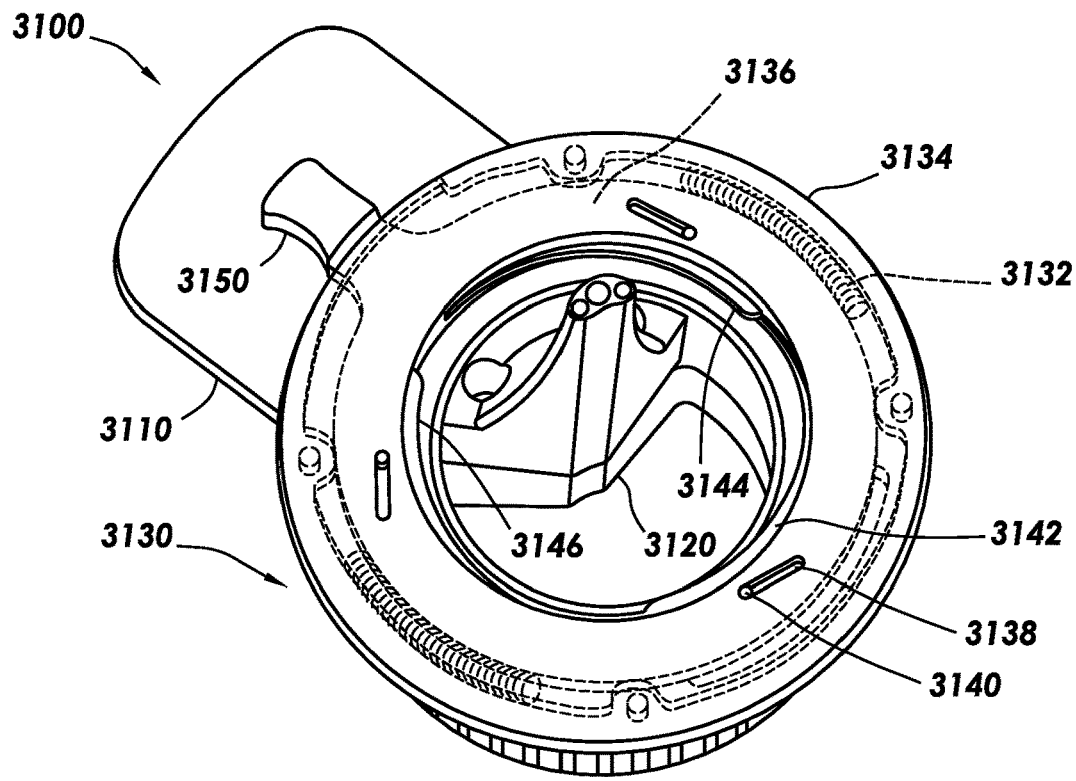
FIG. 31A is a bottom perspective view of a visualization device with an attachment mechanism in a closed configuration, and in accordance with at least some embodiments.

FIG. 31A is a bottom perspective view of a visualization device 3100 with an attachment mechanism in a closed configuration. In particular, the visualization device 3100 comprises a base 3110, an imaging assembly 3120, and an attachment mechanism 3130. The example attachment mechanism 3130 comprises an attachment base 3134 that defines an aperture or lumen (through which the imaging assembly 3120 projects), and an annular ring 3136 that defines an actuator or tab 3150 extending therefrom. A set of springs biases the annular ring 3136 toward a first rotational orientation relative to the attachment base 3134. For example, spring 3132 couples between the attachment base 3134 and the annular ring 3136, and biases the annular ring counter-clockwise (in the view of FIG. 31A). While three springs are shown in FIG. 31A to bias the annular ring 3136 relative to the attachment base 3134, one or more may be used.

The example annular ring 3136 defines a plurality of elongate apertures or slots, and in the example case three slots corresponding to three engagement members. For example, slot 3138, representative of all the slots, is in operational relationship with a cylinder or pin 3140. The pin 3140 is disposed within the slot such that as the annular ring 3136 is rotated relative to the attachment base 3134, the pin 3140 slides within the slot 3138. Movement of the pin 3140 within the slot 3138 causes movement of the associated engagement member 3142. Two additional engagement members 3144 and 3146 are visible, and each engagement member is associated with a slot and pin (not specifically numbered). While three engagement members 3142, 3144, and 3146 are shown, two or more engagement members operated as an iris mechanism may be used.

Figure 31B:
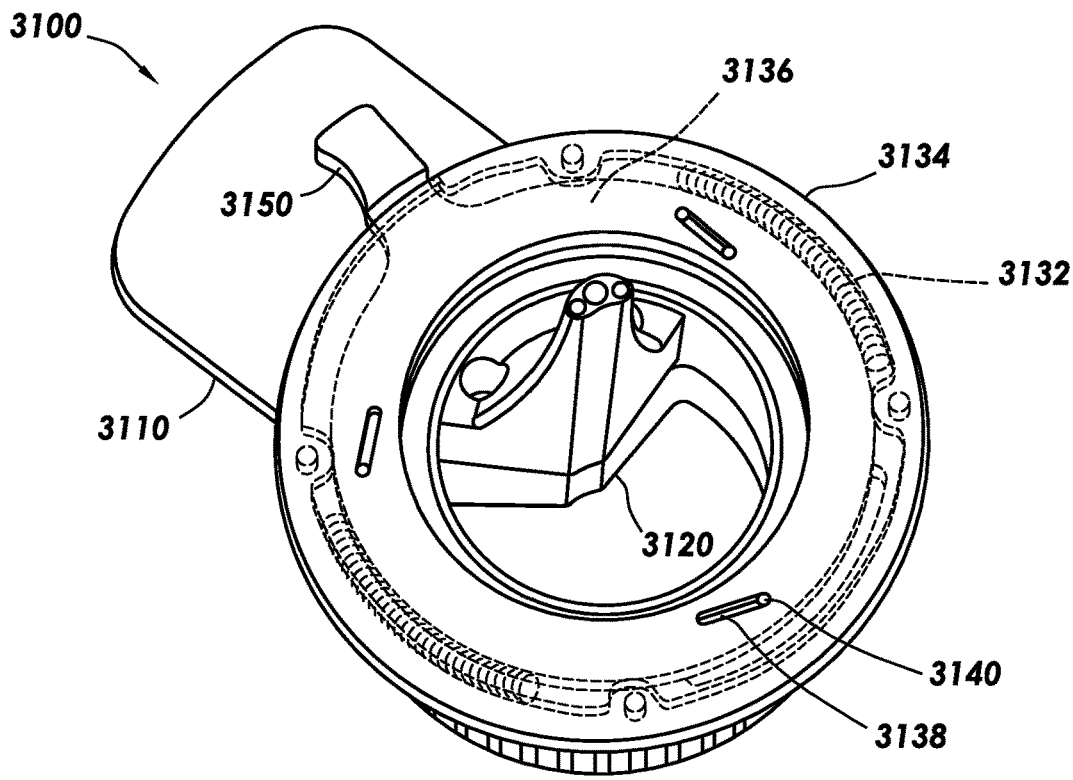
FIG. 31B is a bottom perspective view of a visualization device with an attachment mechanism in an open configuration, and in accordance with at least some embodiments.

FIG. 31B is a bottom perspective view of the visualization device with an attachment mechanism in an open configuration. In particular, in FIG. 31B the annular ring 3136 has been rotated relative to the attachment base 3134, which both charges the springs (e.g., spring 3132), and translates the pins with the slots (e.g., pin 3140 within slot 3138). Translation of the pins along and within their respective slots causes the respective engagement members to retract away from the aperture defined within the annular ring 3136 and attachment base 3134. Thus, in the orientation shown in FIG. 31B none of the engagement members are visible within the aperture through which the imaging assembly 3120 projects.

Referring simultaneously to FIGS. 31A and 31B, in operation a clinician rotates the annular ring 3136 relative to the attachment base 3134, such as by interacting with the tab 3150. With the annular ring 3136 rotated to the rotational position shown in FIG. 31B, the proximal end of a speculum (not shown so as not to unduly complicate the figure) is placed within the aperture. Once the speculum is placed, the clinician releases the tab 3150. With the tab 3150 released, the annular ring 3136 is biased back to the first orientation by the springs (e.g., spring 3132), and the movement to the first orientating extends the engagement members 3142, 3144, and 3146, as shown in FIG. 31A, such that the engagement members 3142, 3144, and 3146 hold the speculum in operational relationship with the visualization device 3100.

While the examples of FIGS. 31A and 31B show the tab 3150 and annular ring 3136 moving in a clockwise direction to retract the engagement members 3142, 3144, and 3146, and moving or allowing the tab 3150 and annular ring 3136 to move in a counter-clockwise direction to deploy or extend the engagement members 3142, 3144, and 3146, the visualization assembly can be designed and constructed to operation with opposite rotational movements as well. In yet still further cases, the tab 315 may be designed and constructed to move radially to engage and release the engagement members.

Figure 32A:
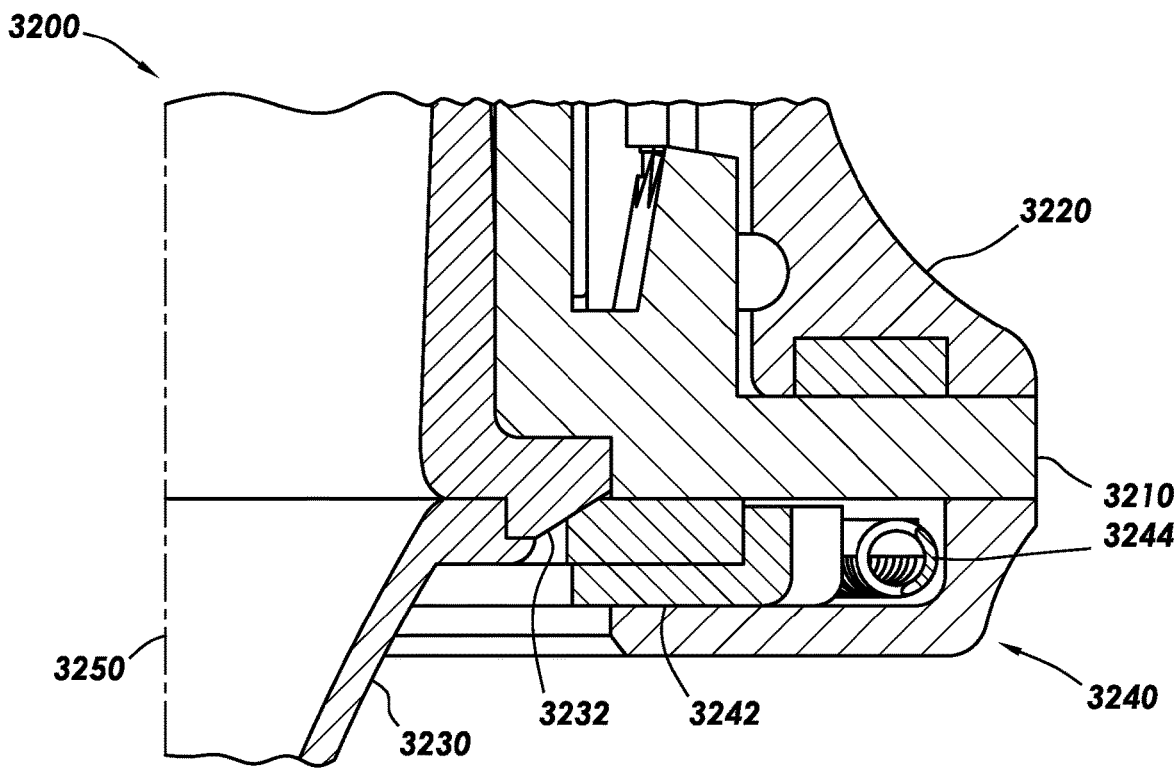
FIG. 32A is a side cross-sectional view of a speculum locked within a visualization device, in accordance with a least some embodiments.

FIG. 32A is a side cross-sectional view of a speculum locked within a visualization device 3200. In particular, visible in FIG. 32A is a base 3210, a knob 3220 configured to rotate about the base 3210, a speculum 3230, and an attachment mechanism 3240. The example attachment mechanism 3240 comprises a spring 3244 and an engagement member 3242 configured to advance and retract to engage and disengage, respectively, from the speculum 3230.

FIG. 32A shows the example attachment mechanism 3240 in a closed configuration where the engagement member 3242 is engaged the engagement portion 3232 (e.g., lip, shoulder) of the speculum 3230 so as to hold the speculum 3230 within the base 3210. While engaged, the speculum 3230 may rotate relative to the base 3210, such as rotation about a longitudinal axis 3250 of the speculum 3230, and the rotation as the clinician turns the knob 3220. The example engagement portion 3232 and engagement member 3242 have mating surfaces having matching angles to aid rotation, friction reduction, and releasable attachment. The engagement portion 3232 can function (or include a sub-portion that functions) as a channel or guide that enables movement of the engagement member 3242 therein, such that the speculum 3230 can rotate relative to the base 3210.

Figure 32B:
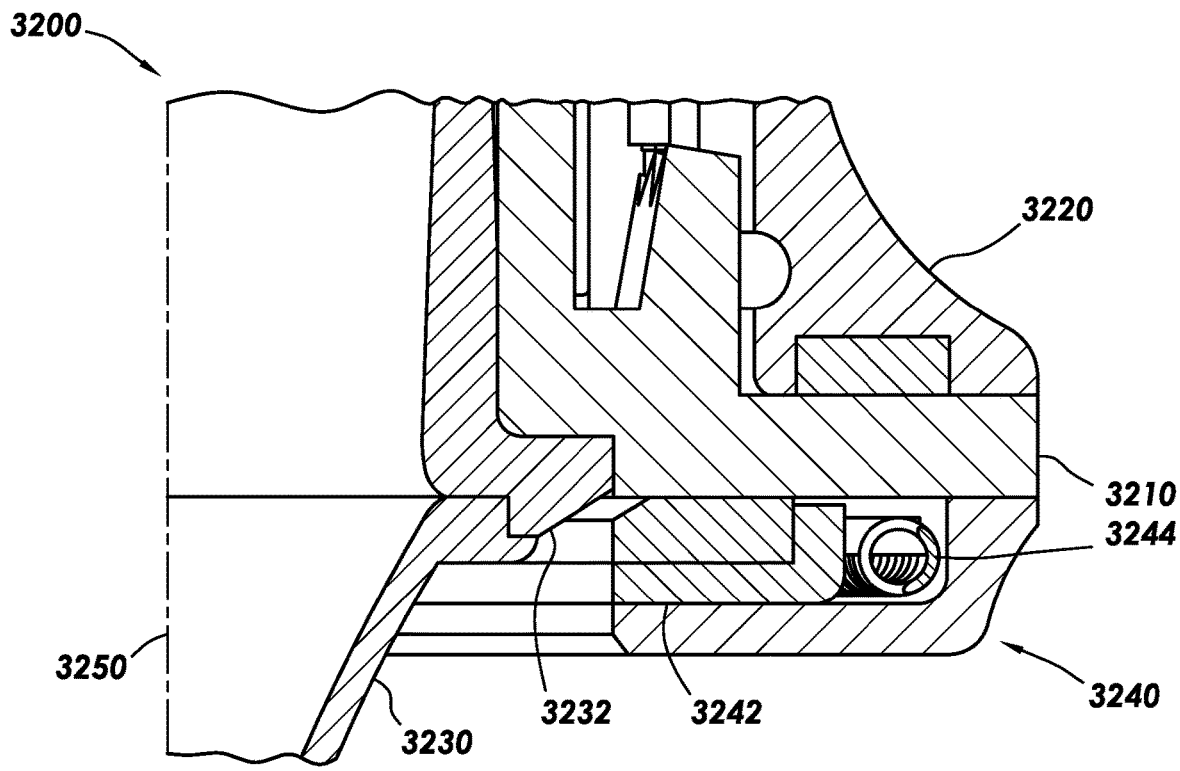
FIG. 32B is a side cross-sectional view of a speculum within a visualization device, but with the engagement members retracted, in accordance with at least some embodiments.

FIG. 32B is a side cross-sectional view of a speculum within a visualization device, but with the engagement members retracted. In particular, FIG. 32B shows the attachment mechanism 3240 in an open configuration with the engagement member 3242 retracted away from the engagement portion 3232 of the speculum 3230 such that the speculum 3230 may be released (e.g., separated) from the base 3210. For example, in the configuration shown in FIG. 32B the speculum 3230 may fall away from the base 3210 due to gravity, or be pulled away by the clinician.

Referring simultaneously to FIGS. 32A and 32B. The base 3210 is stationary relative to the remaining portions. The knob 3220 is coupled to the base 3210 to enable the knob 3220 to rotate relative to the base 3210. Though not shown in FIGS. 32A and 32B, the knob 3220 is coupled to the imaging assembly. When the speculum 3230 is attached as shown in the figures, the imaging assembly is telescoped within the imaging lumen of the speculum 3230. As the knob 3220 is turned by the clinician, the speculum 3230 rotates about the longitudinal axis 3250 based on rotational force imparted to the speculum 3230 by the knob 3220. In some cases, the rotational force is imparted to the speculum 3230 by way of the imaging unit.

In FIGS. 32A and 32B, the attachment mechanism is coupled to and is part of the visualization device (e.g., visualization device 120). In other embodiments, the attachment mechanism may be provided on or integrated with the speculum. The speculum-based attachment mechanism may comprise movable portions (e.g., elastic or resilient portions) and/or living springs. For example, a speculum-based attachment mechanism may be configured to transition from a first configuration (e.g., expanded configuration) to a second configuration (compressed configuration) based on a compression force applied to one or more elastic portions. In the expanded configuration, the speculum-based attachment mechanism may be engaged to a corresponding feature of a rotation mechanism. In the compressed configuration, a diameter of the speculum attachment mechanism is reduced via compression such that the speculum may be released (e.g., separated) from the rotation mechanism.

Figure 33A:
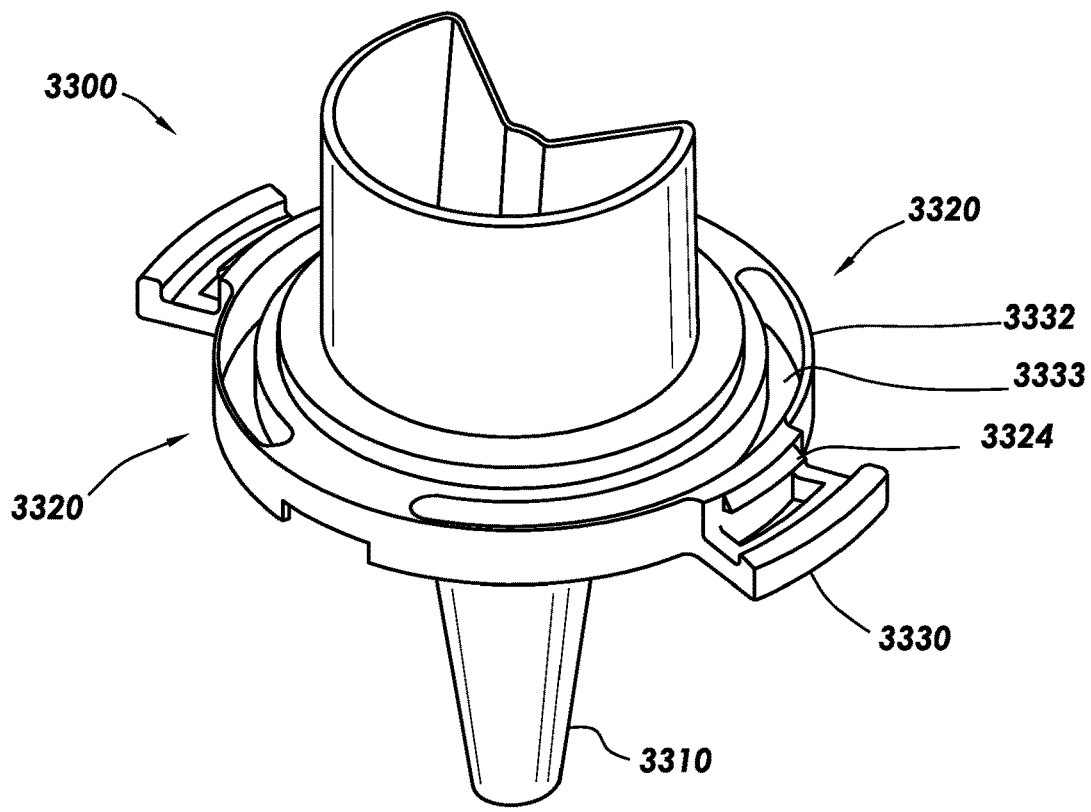
FIG. 33A is a perspective view of a speculum having an attachment mechanism carried by the speculum, in accordance with at least some embodiments.

FIG. 33A is a perspective view of an example speculum 3300 having an attachment mechanism carried by the speculum. In particular, visible in in FIG. 33A is a tip 3310 and an example speculum-based attachment mechanism 3320. The speculum-based attachment mechanism 3320 comprises a set of actuators (e.g., 3330), engagement members (e.g., engagement member 3324), and springs (e.g., spring 3332). Considering actuator 3330 and spring 3332 as representative, spring 3332 rigidly couples on each end to the medial portion of the speculum 3300. The spring 3332 may take any suitable form, such as a leaf spring or living spring. The spring 3332, which may be integrally formed with the speculum, defines an annular groove 3333 between an inside surface of the spring 3332 and the medial portion of the speculum 3300, where the annular groove 3333 partially circumscribes the speculum. The example actuator 3330 is disposed on an outer surface of the spring 3332 opposite the groove 3333, and as shown in some cases the actuator 3330 is medially disposed between the ends of the spring 3332. In operational relationship with the actuator 3330 is an engagement member 3324 illustratively shown as an angled ridge, where the slope of the ridge increases in height with increasing distal distance along the speculum 3300.

In accordance with these example embodiments, the actuator 3330 and spring 3332 form a squeeze tab. That is, actuator 3330 (and the actuator on the opposite side not specifically numbered) may be configured to be moved (e.g., compressed) inward toward a longitudinal axis of the speculum 3300. For example, a clinician may hold the set of actuators (e.g., actuator 3330) with a thumb and finger and apply a compression force to squeeze the actuators together and reduce a diameter of the speculum 3300 to place or release (e.g., separate) the speculum 3300 on or off a scope, respectively. In particular, in the compressed configuration the engagement members (e.g., engagement member 3324) slides out of operational relationship with an attachment member on the visualization device (not shown) to enable sliding the speculum 3300 on or off the scope.

Figure 33B:
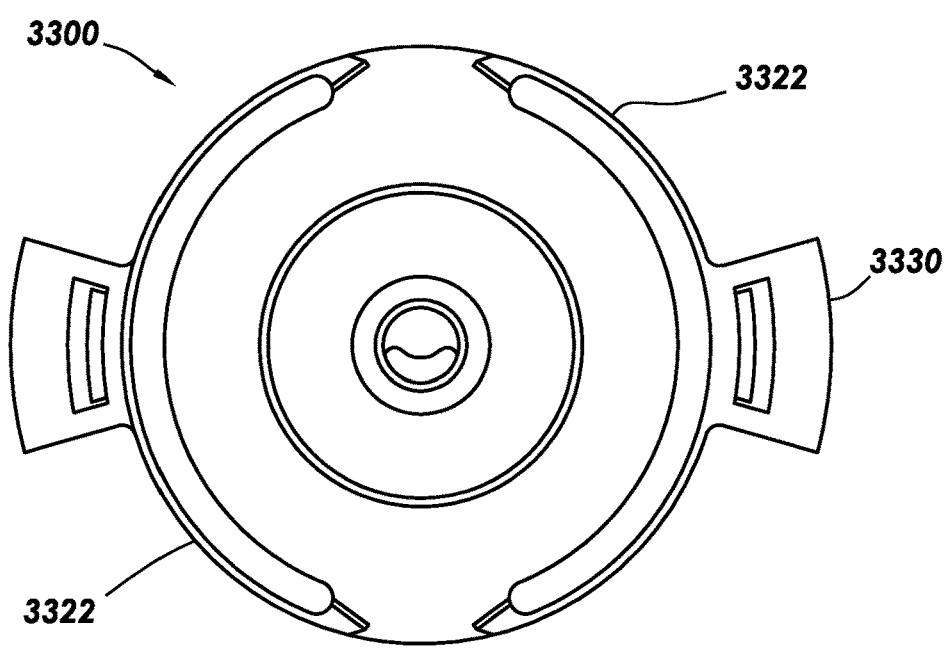
FIG. 33B is a bottom view of a speculum having an attachment mechanism carried by the speculum, in accordance with at least some embodiments.

FIG. 33B is a bottom view of the speculum 3300 of FIG. 33A. Referring simultaneously to FIGS. 33A and 33B, the speculum 3300 is shown in a first (e.g., resting or expanded) configuration. To couple the speculum 3300 to the scope (e.g., to couple the engagement member 3324 with corresponding engagement portion(s) of the scope), a clinician applies a compression force to the actuators (e.g., actuator 3330) to move the engagement portion inward (e.g., to change the speculum 3300 into a second or compressed configuration). The clinician may then telescope the speculum 3300 into mating relationship with the scope, and more particularly engage the imaging lumen with the imaging assembly and telescope the proximal end of the speculum into an aperture formed by the rotation mechanism (e.g., knob). Once in place, the clinician releases the actuators to enable the speculum 3300 to return to its resting or expanded configuration, which thus places the engagement portions into mating relationship with corresponding features of the scope.

In other embodiments, the force used to compress the springs and thus create the compressed orientation may be provided merely by pushing the speculum 3300 into place on the scope. That is, the speculum 3300 in the expanded configuration is telescoped onto the scope, and the force of the springs 3322 can be overcome by the sloped surface of the engagement portions (e.g., engagement member 3324) interacting with a corresponding feature of the speculum 3300 to move into a compressed configuration and engage with the scope. For example, as the speculum 3300 is being pressed against the scope, the springs can be compressed such that the movable portions of the speculum 3300 that carry the engagement portions move inwards and enable the speculum 3300 to slide into engagement with the scope and then spring back into its expanded configuration to maintain its engagement with the scope. Such engagement is further described with reference to FIG. 34.

Figure 34:
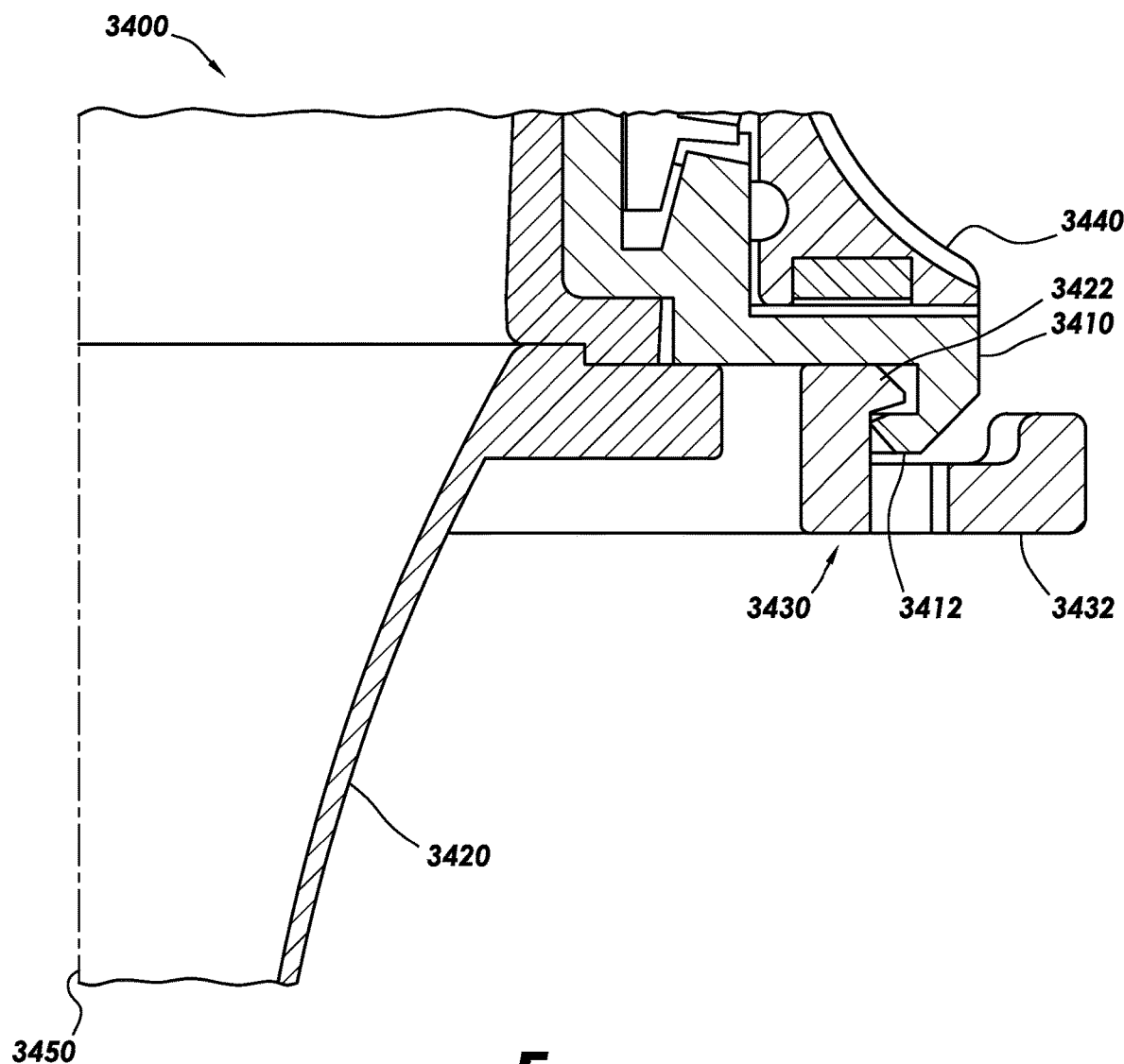
FIG. 34 shows a side cross-sectional view of a speculum within a visualization device in accordance with at least some embodiments.

FIG. 34 shows a side cross-sectional side view of a speculum coupled to a visualization device 3400. In particular, visible in FIG. 34 is a base 3410, a knob 3440 configured to rotate about the base 3410, a speculum 3420, and a speculum-based attachment mechanism 3430. The visualization device 3400 of FIG. 34 may comprise components that are structurally and/or functionally similar to other visualization systems described herein, and in particular, those described in reference to FIGS. 33A and 33B. The example speculum 3420 comprises a latch or engagement portion 3422 configured to engage a corresponding engagement portion 3412 of the base 3410 so as to hold the speculum 3420 relative to the base 3410. However, the speculum 3420 may be configured to rotate relative to the base 3410 about a longitudinal axis 3450 of the speculum 3420. The speculum attachment mechanism 3430 in the first configuration is biased to be in an expanded configuration (as shown), such that the speculum 3420 can be engaged with the base 3410.

The speculum-based attachment mechanism 3430 may include the actuator 3432 configured to be pressed towards the longitudinal axis 3450. When the attachment mechanism 3430 is compressed, the diameter of the attachment mechanism 3430 is reduced and the engagement portion 3412 disengages from the engagement portion 3412 of the base 3410. The reduced diameter and disengagement enables the speculum to be released (e.g., separated) from the base 3410. For example, a clinician may push the actuator 3432 inward and then move (e.g., pull) the speculum 3420 away from the base 3410 to release the speculum 3420 from the base 3410.

iii. Image Rotation Assembly

Endoscopes can be configured to generate images having a rotational orientation consistent with a rotational orientation of the endoscope itself. For example, an endoscope rotated with respect to a reference position may generate a rotated image, for example, rotated by up to 180 degrees in either a clockwise or counter-clockwise direction depending on the amount of rotation of the endoscope. A viewer of the image data may become disoriented unless a reference position is provided. In some cases, a symbol such as a chevron mark is overlaid on image data to indicate the relative rotational orientation of the endoscope. However, the symbol-based indication may be a suboptimal solution since the clinician may need to manually manipulate a surgical instrument relative to the rotated endoscope rather than relative to the clinician's own perspective. In this case, if a clinician does not consistently perform a procedure from the perspective of the rotated endoscope, then the clinician may make a mistake and possibly cause injury and/or discomfort to a patient.

Example visualization systems described herein may comprise an image rotation assembly (e.g., image rotation assembly 124) including a rotation mechanism and one or more sensors configured to generate rotation data and orientation data that may be used by a processor (e.g., processor 112), to process image data and present that image data to an operator in a predetermined (e.g., consistent) orientation. For example, the image rotation assembly may include a rotatable knob configured to enable a clinician to rotate the speculum and imaging assembly within an ear canal while a scope is held in place outside a patient's ear.

Figure 16A:
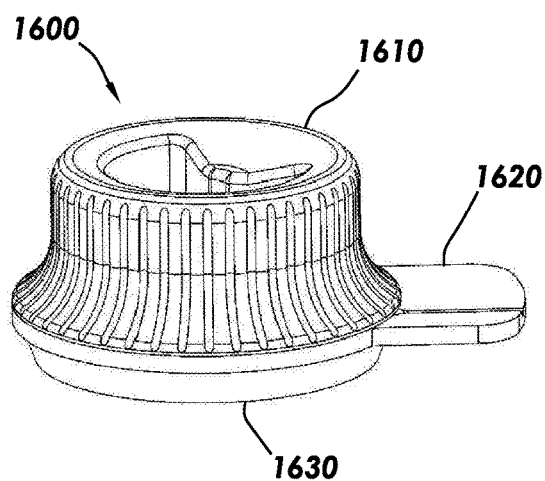
FIG. 16A is a perspective view of an image rotation assembly in accordance with at least some embodiments.
Figure 16B:
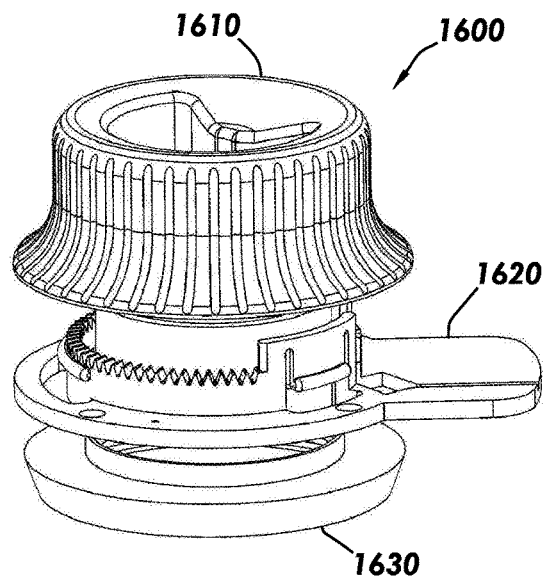
FIG. 16B is an exploded perspective view of an example image rotational assembly in accordance with at least some embodiments.

FIG. 16A shows a perspective view of an image rotation assembly. FIG. 16B shows an exploded perspective view of the example image rotational assembly of FIG. 16A. Referring simultaneously to FIGS. 16A and 16B, a portion of a visualization device 1600 comprises a knob 1610, a base 1620, and an attachment mechanism 1630. The knob 1610 and attachment mechanism 1630 may each be rotatably coupled to the base 1620 and rotate a predetermined number of angular degrees (e.g., 360 angular degrees). As discussed above, the attachment mechanism 1630 may be configured to selectively engage and release a speculum. The example knob 1610 may be coupled such that rotation of the knob 1610 causes rotation of an imaging assembly (not shown for sake of clarity) and an attached speculum. Stated differently, rotation of the knob 1610 and speculum enables the imaging assembly to be rotated relative to a target treatment area (e.g., tympanic membrane) of a patient. Accordingly, the clinician may turn the knob to adjust a field of view of the imaging assembly and a rotational orientation of an attached speculum.

Figure 17:
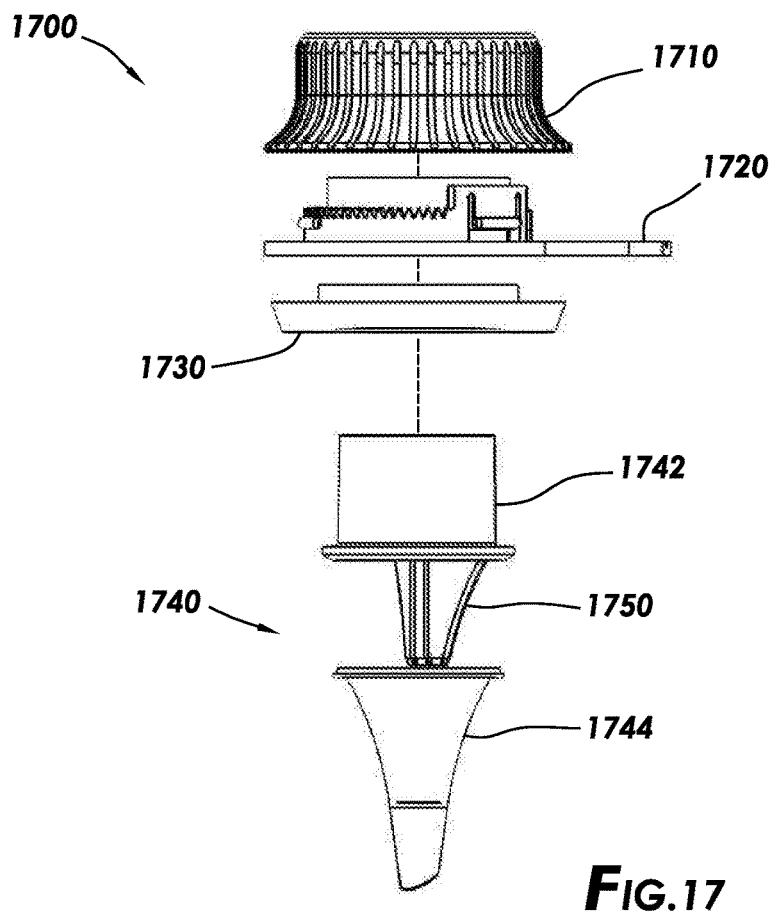
FIG. 17 is an exploded side view of a visualization device in accordance with at least some embodiments.

FIG. 17 is an exploded side elevation view of a visualization device 1700. In particular, FIG. 17 shows a knob 1710, a base 1720, an attachment mechanism 1730, an imaging assembly 1750, and a speculum 1740. The speculum 1740 is itself separated into a proximal portion 1742 and a distal portion 1744 so as to expose the relationship of the imaging assembly 1750 relative to the proximal portion 1742. The knob 1710, the attachment mechanism 1730, and the speculum 1740 may each be configured to rotatably couple to the base 1720. For example, the proximal portion 1742 of the speculum 1740 may be advanced through an opening in the base 1720 and the knob 1710.

Figure 18:
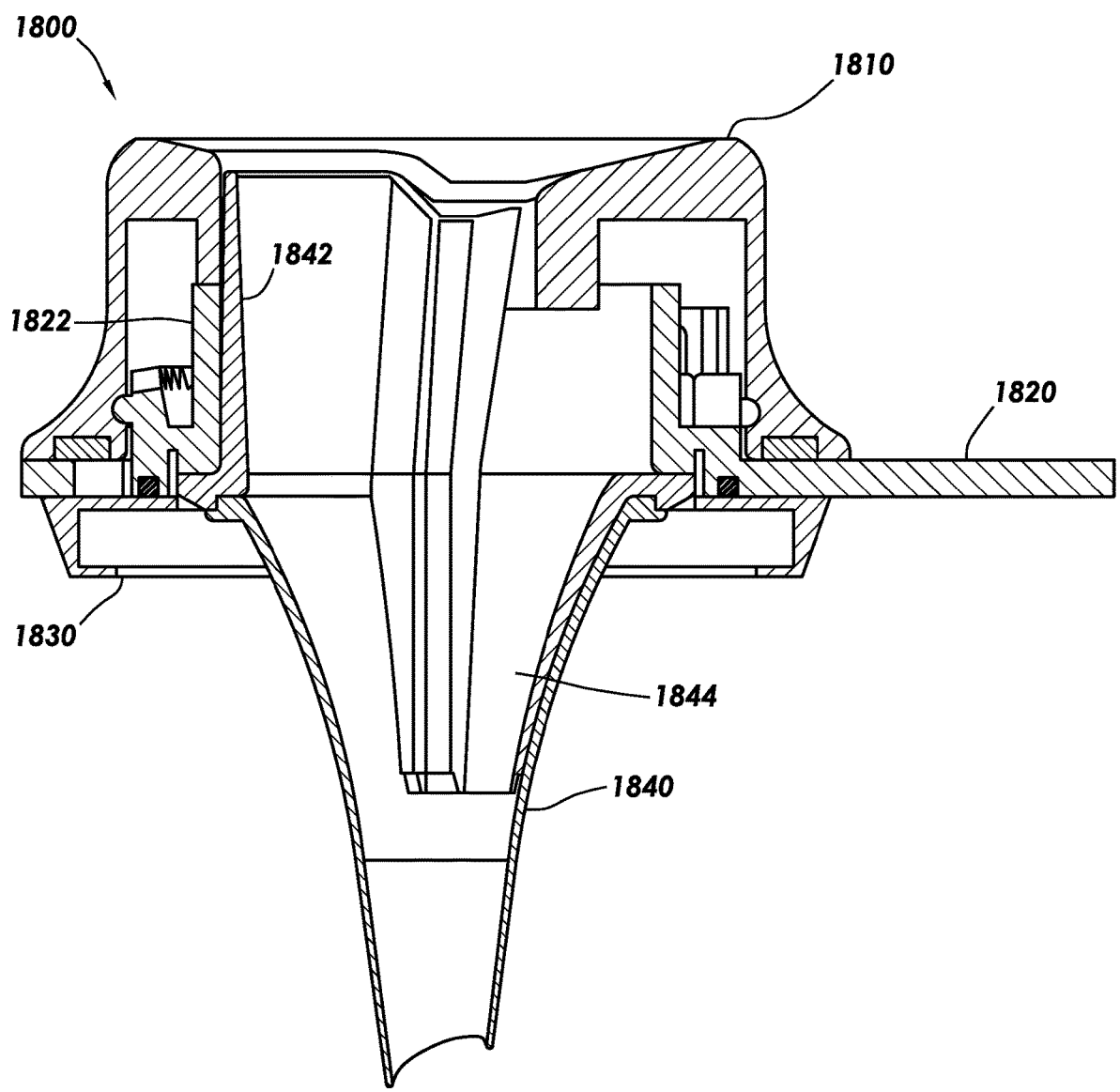
FIG. 18 is a cross-sectional side view of visualization device in accordance with at least some embodiments.

FIG. 18 is a cross-sectional side view of visualization device 1800. In particular, visible in FIG. 18 is a knob 1810, a base 1820, an attachment mechanism 1830, and a speculum 1840. The details of the attachment mechanism 1830 are omitted so as not to unduly complicate the figure. The knob 1810, the attachment mechanism 1830, and the speculum 1840 may each be configured to rotatably couple to the base 1820. The example base 1820 is disposed between the knob 1810 and the speculum 1840. A proximal portion 1842 of the speculum 1840 may be configured to rotate relative to a sidewall 1822 being part of or rigidly coupled to the base 1820. The imaging assembly may be rotatably coupled to the knob 1810 and disposed within an imaging lumen 1844 of the speculum 1840, though the imaging assembly is not shown so as not to unduly complicate the figure. As the knob 1810 is rotated relative to the base 1820, the imaging assembly and speculum 1840 rotate with the knob 1810. In one example case, the knob 1810 and the speculum 1840 may rotate about the full 360 angular degrees. In another case, the knob 1810 and the speculum 1840 may rotate at least about 180 angular degrees, and in yet another case at least about 90 angular degrees.

In example embodiments, a processor and the image rotation assembly may be configured to measure rotation of the knob, imaging assembly, and/or speculum. Image data generated by the imaging assembly may be processed to correspondingly rotate the image data by the measured rotational change, e.g., in an opposite direction. Accordingly, an orientation of the image data viewed by a clinician on a screen or display (e.g., display 111) remain in substantially the same rotational orientation throughout a procedure regardless of rotation of the speculum and imaging assembly. That is, the perspective of the image may substantially match the perspective of the clinician throughout a procedure regardless of a rotational state of the imaging assembly and speculum. Counteracting the rotation of the image in spite of rotation of the imaging assembly around the longitudinal axis of the speculum may reduce a cognitive burden of a clinician and may improve procedure efficiency as well as patient outcomes.

In order to determine an amount of rotation imparted on the knob, and thus the speculum, in some example embodiments the image rotation assembly comprises a sensor configured to generate orientation data that may be used by the processor to process the image data (e.g., rotate the image data) to achieve the predetermined (e.g., consistent) image orientation.

In some embodiments, the sensor(s) to determine rotational position of the imaging assembly may include a position sensor such as an encoder (e.g., rotary encoder) configured to generate rotation data. In some embodiments, the rotation data may include absolute position data and angular position data. The encoder may be configured to generate absolute position data in real-time. The processor may be configured to process (e.g., rotate) the image data to reflect a predetermined orientation based on the rotation data and orientation data.

In some embodiments, the encoder may be configured to measure a predetermined number (e.g., 16) discreet rotational positions and provide a resolution of about 22.5 degrees in order to ensure smooth rotation of the image data. Each position of a sixteen-position encoder may be separated by an angle of about 22.5 degrees. Accordingly, rotation of an image rotational assembly past one of these positions corresponds to a rotation of the image data by about 22.5 degrees. In some cases, the encoder may include between about 16 and 90 discreet positions, inclusive. A 90 position encoder may provide a resolution of about 4 degrees and may enable smoother rotation of an image on a display.

Figure 19:
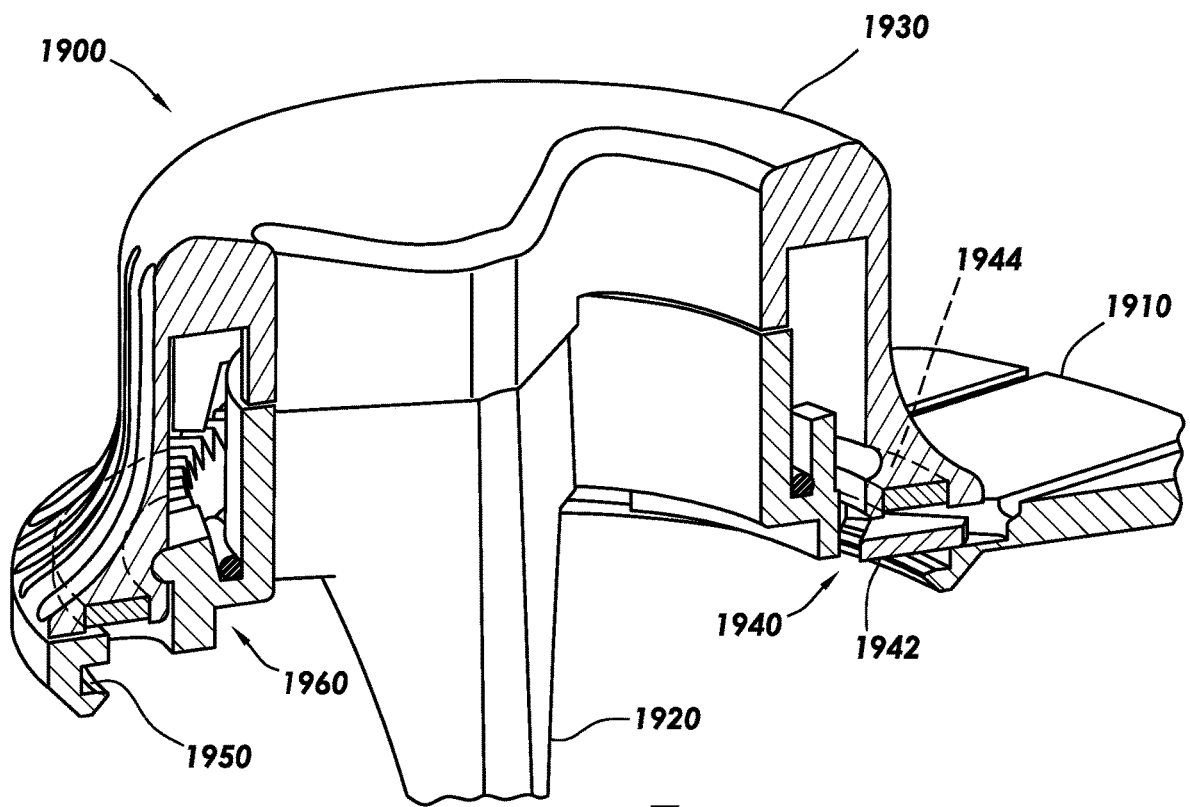
FIG. 19 is a cross-sectional perspective view of a visualization device with a rotational position encoder in accordance with at least some embodiments.

FIG. 19 is a cross-sectional perspective view of a visualization device 1900 with a rotational position encoder. In particular, visible in FIG. 19 is a base 1910, an imaging assembly 1920, an image rotation assembly 1940, an annular channel 1950, and a wire management system 1960. The example visualization device of FIG. 19 is configured for use with a speculum (not shown) that carries a speculum-based attachment mechanism (e.g. as shown in FIGS. 33A, 33B, and 34). The example image rotation assembly 1940 comprises a magnet 1944 and a knob 1930. As before, the imaging assembly 1920, image rotation assembly 1940, and speculum attachment mechanism in the form an annular channel 1950 may each be configured to rotatably couple to the base 1910. In one example embodiment, the base 1910 includes and/or supports a magnetic encoder sensor 1942 that is configured to measure a magnetic field of the magnet 1944. The magnetic encoder sensor 1942 may be fixed relative to the magnet 1944. Stated otherwise, the magnetic encoder sensor 1942 may be stationary relative to the base 1910. The example magnet 1944 takes form of an annular ring with a set of alternating poles radially spaced around the annular ring 1944. The example magnetic encoder sensor 1942 is configured to generate rotation data regarding change in angular position of the image rotation assembly 1940, and in some cases may be able to determine absolute angular position. For example, rotation of the knob 1930 rotates the magnet 1944, and rotational of the magnetic induces magnetic field changes measured by the magnetic encoder sensor 1942, thus creating rotation data. Rotation data generated by the magnetic encoder sensor 1942 may be sent to the processor (e.g., processor 112) and used to process image data generated by imaging assembly 1920 to rotate the image data to account for rotation of the imaging assembly 1920.

Figure 20:
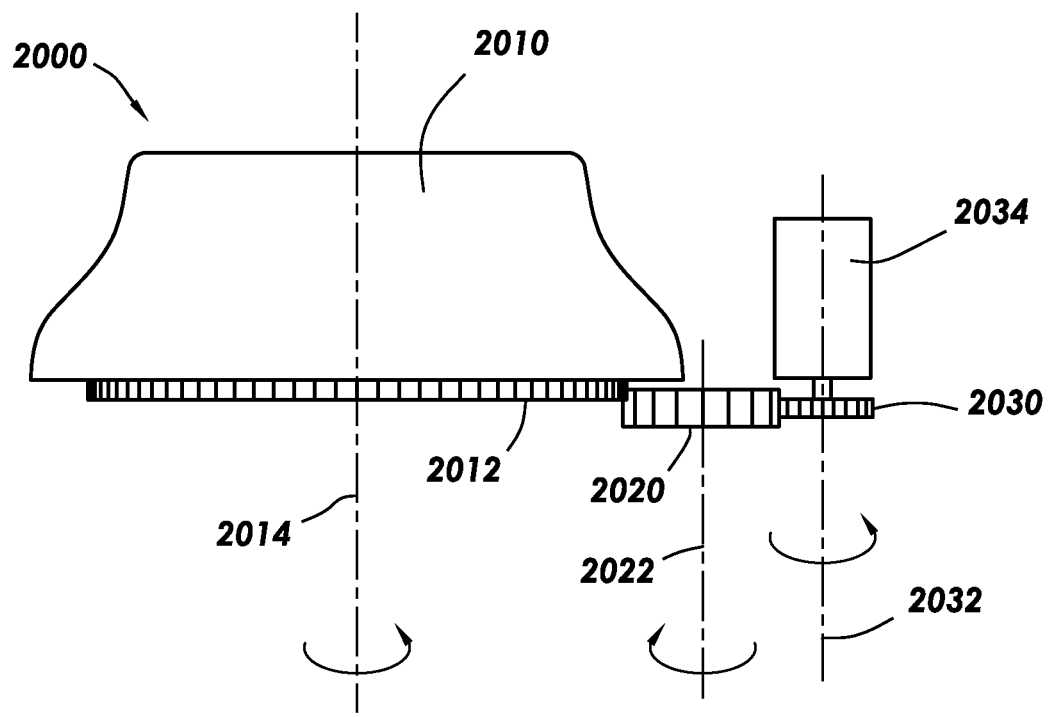
FIG. 20 is a simplified schematic diagram of an image rotation assembly with a position encoder in accordance with at least some embodiments.

FIG. 20 is a simplified schematic diagram of an image rotation assembly of a visualization device 2000 with a mechanical position encoder. In particular, FIG. 20 shows a knob 2010, a sprocket or gear 2012 coupled to the knob 2010, an intermediate sprocket or gear 2020, and a mechanical encoder 2034 comprising a sprocket or gear 2030. The example mechanical encoder 2034 is configured to generate rotation data. In the example shown, the gear 2012 is part of the image rotation assembly (e.g., the knob 2010), and more specifically the gear 2012 is integral formed with or rigidly coupled to the knob 2010. In some cases, the gear 2012 has an axis of rotation 2014 that is coaxial with the longitudinal axis of a speculum (when attached). The gear 2020 is an intermediate gear that transfers the rotation from the gear 2012 to the gear 2030 of the mechanical encoder 2034. Thus, the intermediate gear 2020 has an axis of rotation 2022 that is parallel to and spaced apart from the axis of rotation 2014. The gear 2030 is coupled to the shaft of the mechanical encoder 2034, and defines an axis of rotation 2032 that is parallel to and offset from both the axes of rotation 2014 and 2022. The example encoder 2034 is configured to measure changes in rotation of the image rotation assembly via the gear 2012, the intermediate gear 2020, and the gear 2030, and the example mechanical encoder 2034 generates rotation data. Rotation data generated by the mechanical encoder 2034 may be sent to the processor (e.g., processor 112) and used to process image data generated by the imaging assembly to rotate the image data to account for rotation of the imaging assembly.

Figure 21:
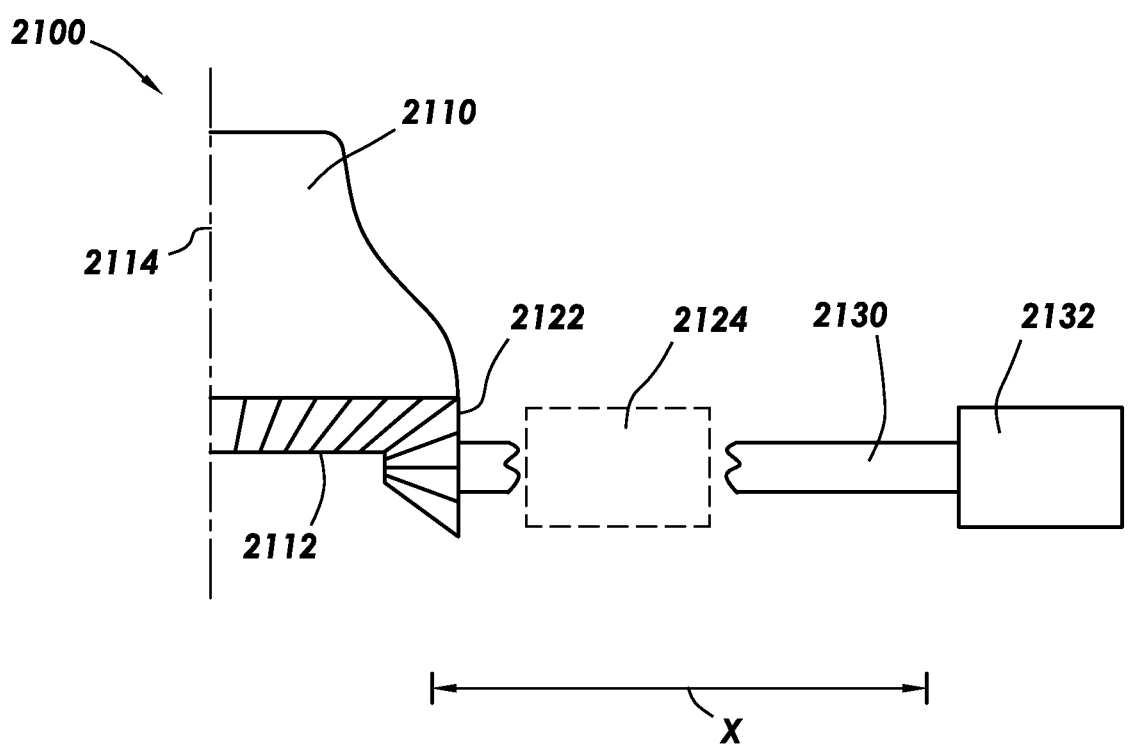
FIG. 21 is a schematic diagram of an image rotation assembly with a position encoder in accordance with at least some embodiments.

FIG. 21 is a schematic diagram of an image rotation assembly of a visualization device 2100 with another example positon encoder. In particular, FIG. 21 shows a knob 2110, a sprocket or gear 2112, a sprocket or gear 2122, and a mechanical encoder 2124. The example mechanical encoder 2124 is configured to generate rotation data. In the example shown, the gear 2112 is part of the image rotation assembly, and more specifically the gear 2112 is integral formed with or rigidly coupled to the knob 2110. The gear 2122 may be rotationally coupled to the gear 2122. As shown, the gear 2112 and the gear 2122 may be bevel gears. The knob 2110 and the gear 2112 may be configured to rotate about a rotation axis 2014, and the gear 2122 may be configured to rotate about an axis perpendicular to the rotation axis 2014. The mechanical encoder 2124 may be configured to measure rotation of the knob 2110 via the gear 2112 and the gear 2122. As an alternative to the gear 2112, the gear 2122, and the mechanical encoder 2124, the image rotation assembly may include the second gear 2112, a cable 2130 (e.g., torque cable), and the encoder 2132. The cable 2130 may be configured to couple the second gear 2122 to the encoder 2132 in order to increase a distance X between the knob 2110 and the encoder 2132.

Figures 22A, 22B:
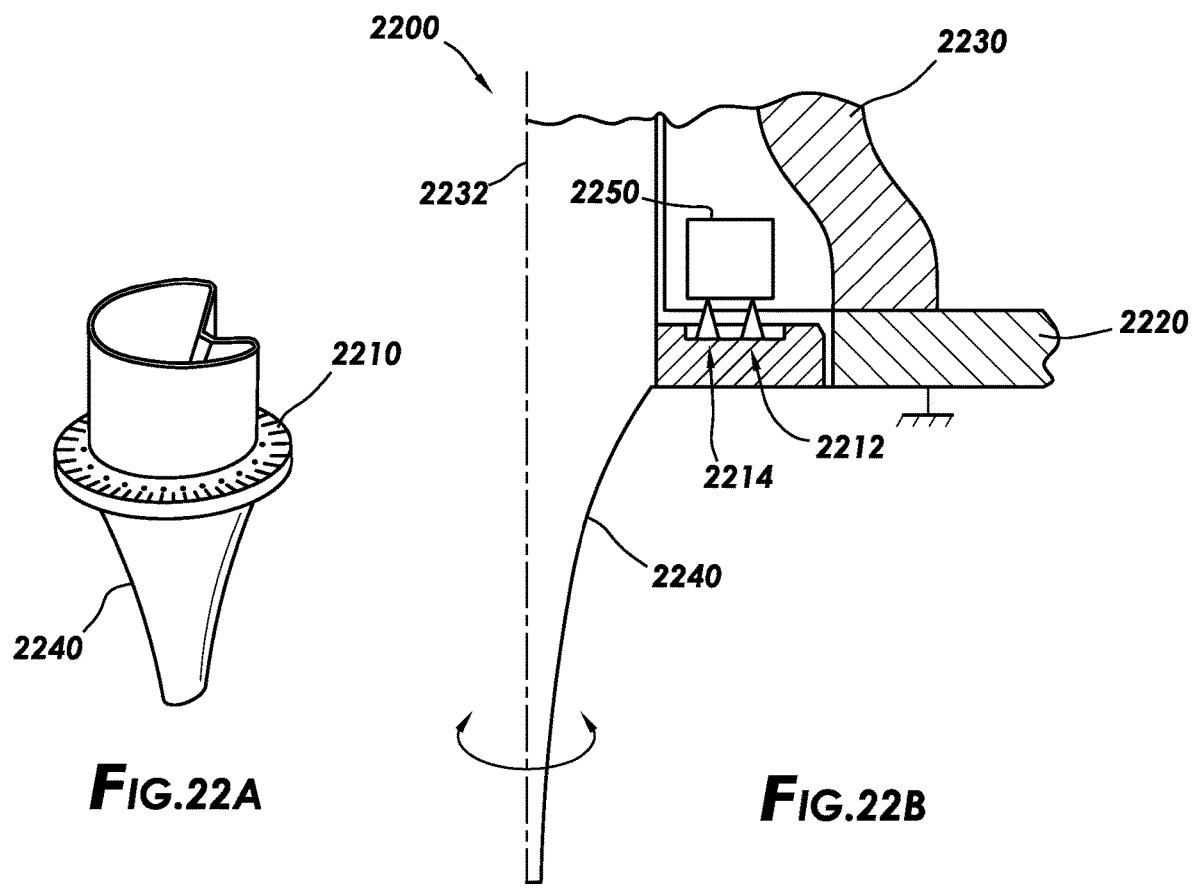
FIGS. 22A and 22B are schematic diagrams of an image rotation assembly with a position encoder in accordance with at least some embodiments.

FIGS. 22A and 22B are schematic diagrams of an image rotation assembly of a visualization system 2200 with another example positon encoder. In particular, FIGS. 22A and 22B show a base 2220, a speculum 2240, an image rotation mechanism 2230, and an optical rotation sensor assembly. The optical rotation sensor assembly comprises an optical encoder 2250 disposed within the rotation mechanism 2230 and fixed relative to the base 2220. The optical encoder 2250 is configured to read an optically-readable pattern 2210 on a portion of the speculum 2240. The image rotation mechanism 2230 and the speculum 2240 may be configured to rotate about a rotation axis 2232. The optical encoder 2250 may be configured to measure rotation of the speculum 2240 via optical measurements of a first pattern 2212 and a second pattern 2214. The optically readable pattern 2210 may include absolute position data 2214 and dynamic position data 2212 (e.g., angular position data). The absolute position data 2214 can include, for example, unique marks and/or patterns at each location, and the dynamic position data 2212 can include, for example, the same type of mark (e.g., a line or a dot) and/or repeated markings or patterns. In some embodiments, when dynamic position data 2212 are used instead of absolute position data 2214, a clinician may need to calibrate the visualization device before uses, e.g., to indicate where a starting or zero position is and/or to indicate a current position of the device. Alternatively, a visualization device (or control device operatively coupled to the visualization device) can be equipped with memory to store its last known position and/or be configured to operate in a lower power state such that the image rotation assembly is capable of tracking its movements when not in use. The optical encoder 2250 may be configured to generate rotation data. Rotation data generated by the optical encoder 2250 may be sent to the processor (e.g., processor 112) and used to process image data generated by the imaging assembly to rotate the image data to account for rotation of the imaging assembly.

In some embodiments, the optical encoder 2250 may include an optical sensor that may include a photodiode, charged coupled device (CCD), or complementary metal-oxide semiconductor (CMOS) optical sensor. In some embodiments, the optical encoder 2250 may be mounted on a portion of the base 2220 within the rotation mechanism 2230, and the optical encoder may be stationary relative to the base 2220.

In some embodiments, the optical pattern 2210 may be printed on a predetermined portion of the speculum 2240 (e.g., flange) or applied to a predetermined surface of the speculum 2240 using an adhesive. For example, the optical pattern 2210 may be disposed on a radial sticker applied to the speculum 2240.

Figure 23:
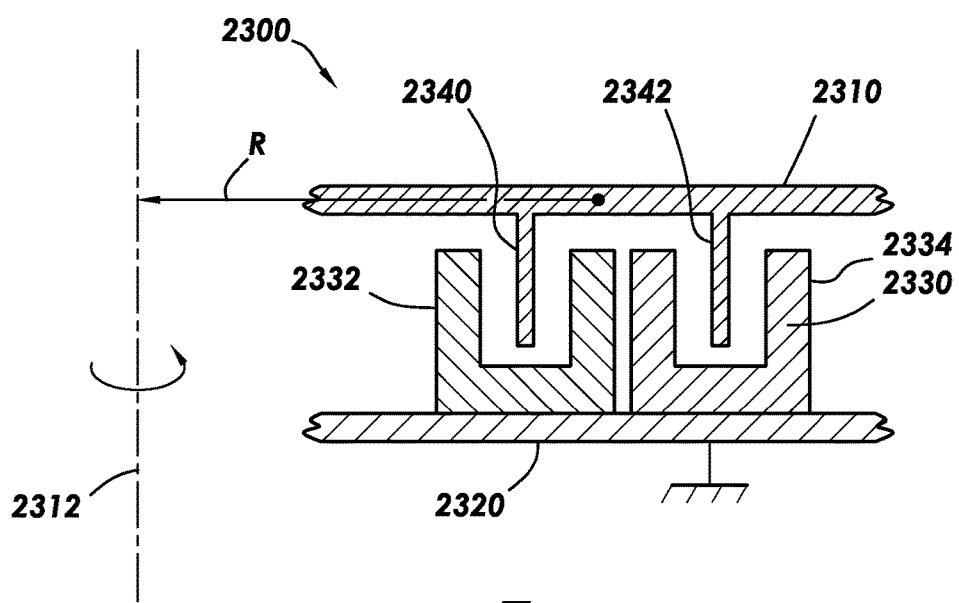
FIG. 23 is a schematic diagram of an image rotation assembly with a position encoder in accordance with at least some embodiments.

FIG. 23 is a schematic diagram of an image rotation assembly of a visualization system 2300 with another example position encoder. In particular, FIG. 23 shows a base 2320, an image rotation mechanism 2310, and optical rotation sensor assembly 2330. The optical rotation sensor assembly 2330 may include a set of optical encoders (e.g., "interrupt" encoders) such as an optical encoder 2332 and an optical encoder 2334, both disposed on a portion of the base 2320. A portion of the image rotation assembly (the portion shown as 2310) rotationally couples to a speculum (not shown) such that the portion 2310 and speculum rotate relative to the optical encoders 2332, 2334 and the base 2220. The portion 2310 (e.g., a knob) may be configured to rotate a rotation axis 2312. The portion 2310 may include a set of optical patterns or tabs 2340, 2342 configured to pass within a respective channel of the optical encoders 2332, 2334 so as to generate an "interrupt" signal by blocking the respective optical encoders 2332, 2334. The set of tabs 2340, 2342 may include a set of features such as protrusions configured in a predetermined sequence.

In some embodiments, the optical encoders 2332, 2334 may be configured to measure rotation of the portion 2310 of the image rotation assembly via optical measurements of an optical pattern caused by tab 2340 passing through the optical encoder 2332, and tab 2342 passing through the optical encoder 2334. The optical patterns created by the tabs 2340, 2342 may correspond to absolute position data (e.g., unique marks or patterns indicating absolute angular position) and dynamic position data (e.g., repeated or the same marks or patterns indicating incremental movement). The optical encoders 2332, 2334 may be configured to generate rotation data. In some embodiments, the optical encoders 2332, 2334 may include an optical sensor that may include a photodiode, charged coupled device (CCD), or complementary metal-oxide semiconductor (CMOS) optical sensor. Rotation data generated by the optical encoders 2332 and 2334 may be sent to the processor (e.g., processor 112) and used to process image data generated by the imaging assembly to rotate the image data to account for rotation of the imaging assembly.

Figure 24:
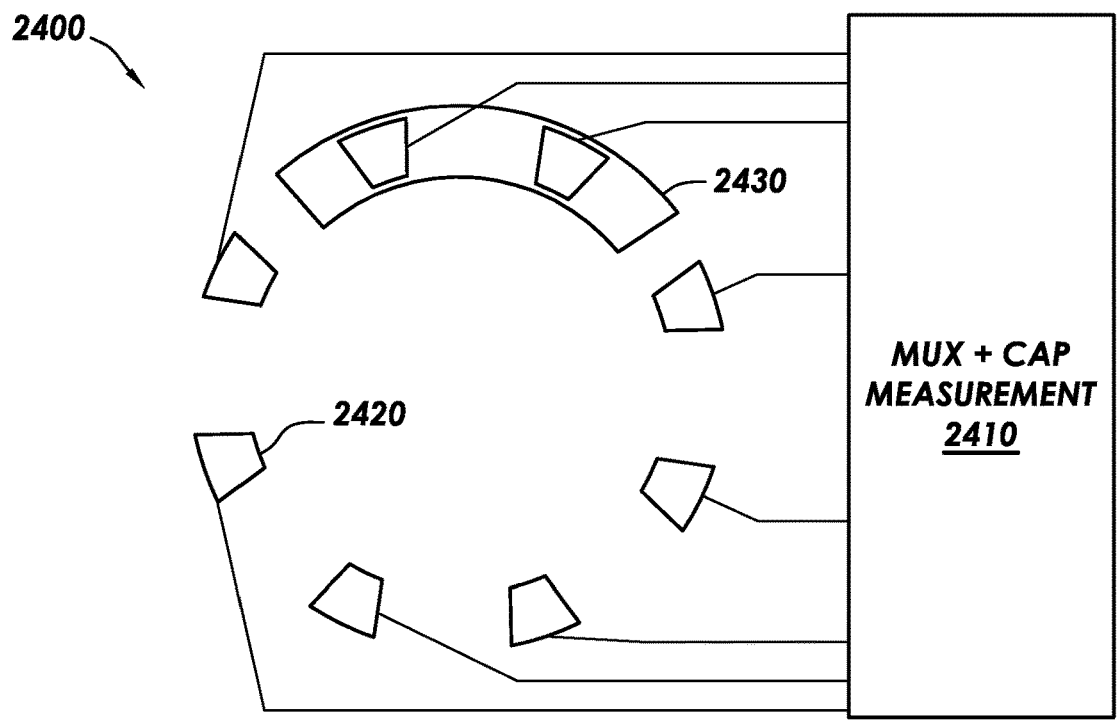
FIG. 24 is a schematic diagram of a sensor of an image rotation assembly in accordance with at least some embodiments.

FIG. 24 is a schematic diagram of a rotation sensor of an image rotation assembly. In particular, FIG. 24 shows a visualization system 2400 including a capacitance measurement circuit 2410, a plurality of conductive pads or a conductive pattern 2420 disposed on a base (not shown), and a rotatable conductive portion 2430 coupled to an image rotation mechanism (not shown). In some embodiments, the conductive pattern 2420 may include a set of spaced apart conductive segments (e.g., copper pads). In particular, the conductive pattern 2420 may comprise a plurality of conductive pads, each conductive pad at a particular radial location (e.g., relative to a rotational axis of the image rotational assembly). Each conductive pad is electrically isolated from the other conductive pads, and each conductive pad is separately electrically coupled to the capacitance measurement circuit 2410. In the example shown, eight conductive pads are implemented; however, any suitable number may be used (e.g., 16, 32). The greater the number of conductive pads, the higher angular resolution of the system.

The conductive portion 2430 may be configured to rotate relative to the base so as to overlap at least one conductive pad at any given point within the circular rotation path of the conductive portion 2430. In some cases, and as shown, the conductive portion overlaps at least two conductive pads at any given point within the circular rotation path of the conductive portion 2430. The conductive portion 2430 is carried by a rotatable element of the image rotation assembly, such as a knob of the image rotational assembly.

The example capacitance measurement circuit 2410 is configured to measure the capacitance between each segment of the conductive pattern 2420 and the conductive portion 2430. Higher capacitance as between the conductive portion 2430 and any one of the conductive pads of the conductive pattern 2420 indicates the conductive portion is close to or over the conductive pad. Oppositely, lower capacitance as between the conductive portion 2430 and any one of the conductive pads of the conductive pattern 2420 indicates the conductive portion is not close to or is not over the conductive pad. Thus, in the example system the capacitance measurement circuit 2410 is configured to generate rotation data where a rotational position of the rotation mechanism corresponds to measured capacitance values of the conductive pattern 2420. For example, changes in capacitance of each conductive pad measured by the capacitance measurement circuit 2410 corresponds to rotation of the conductive portion 2430 over the conductive pattern 2420. In some embodiments, the conductive pattern 2420 and the conductive portion 2430 may be separated by air (or any other suitable dielectric material) by about 0.1 mm or more.

Figure 25B:
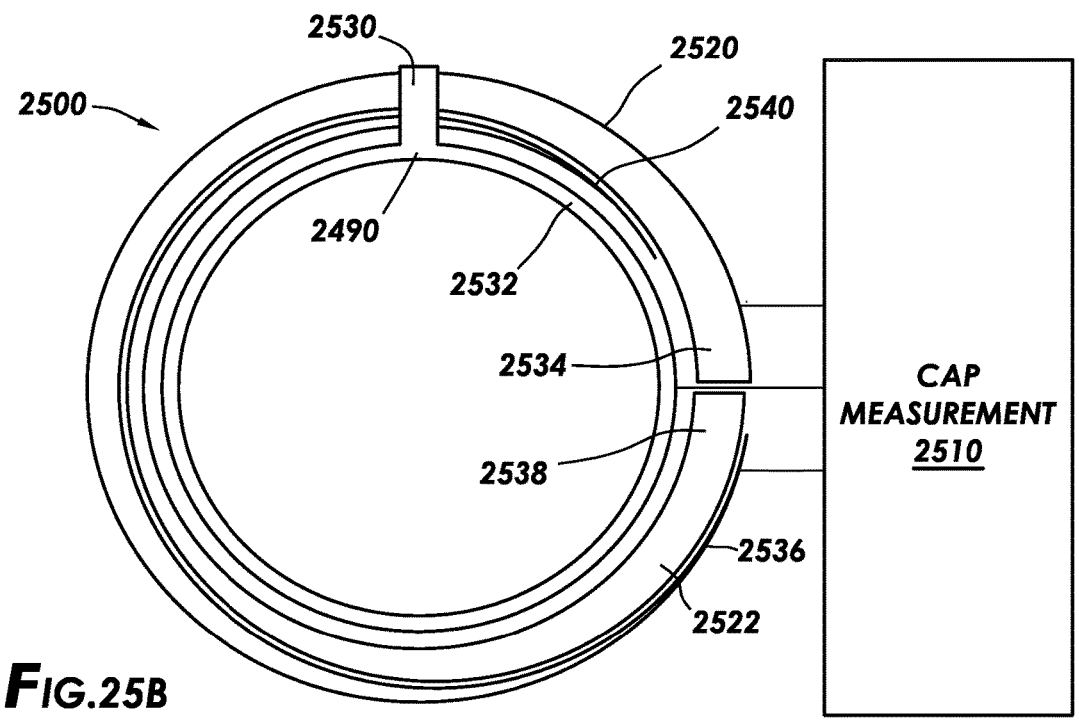
FIG. 25B is a schematic diagram of a sensor of an image rotation assembly in accordance with at least some embodiments.
Figure 25A:
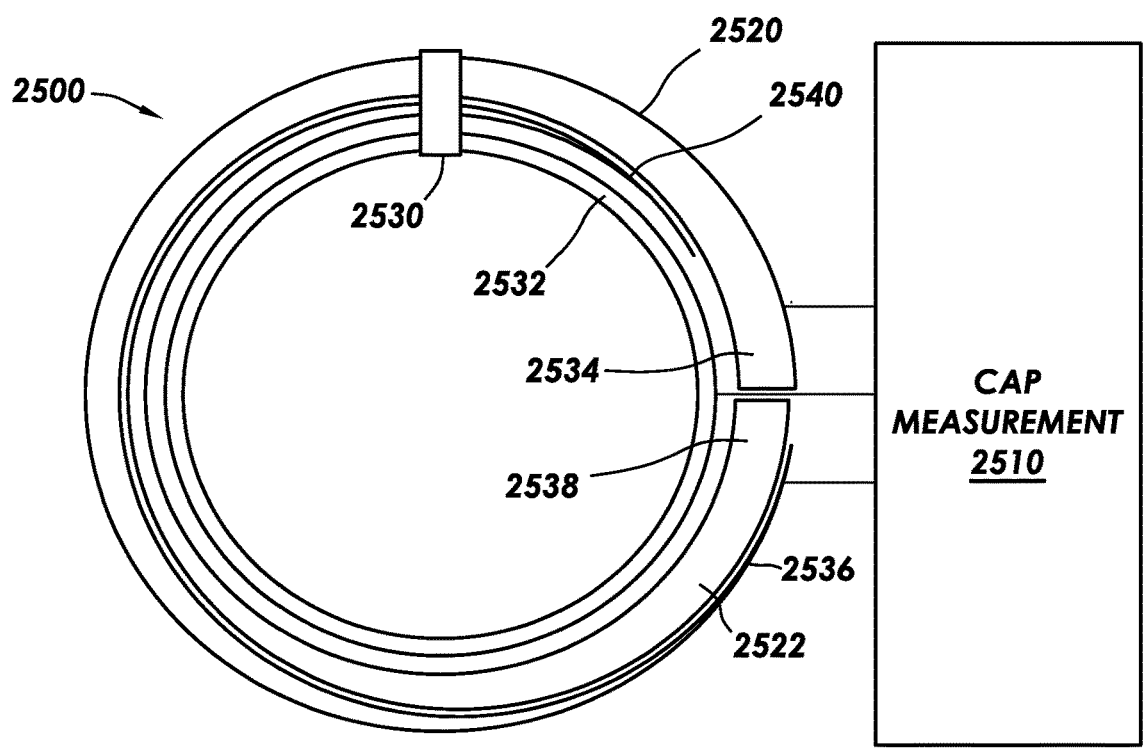
FIG. 25A is a schematic diagram of a sensor of an image rotation assembly in accordance with at least some embodiments.

FIG. 25A is a schematic diagram of a sensor of an image rotation assembly. In particular, FIG. 25A shows an image rotation assembly 2500 comprising a capacitance measurement circuit 2510, a first conductive pattern 2520, a second conductive pattern 2522, a third conductive pattern 2532, and a rotatable conductive portion 2530. The rotatable conductive portion 2530 may be configured to rotate relative to the base so as to overlap the conductive patterns 2520, 2522, 2530 at any given point within the circular rotation path of the rotatable conductive portion 2530. The rotatable conductive portion 2530 is carried by a rotatable element of the image rotation assembly, such as a knob of the image rotational assembly. The first, second, and third conductive patterns 2520, 2522, and 2532 are each be disposed on the base (not shown). The example first conductive pattern 2520 and the second conductive pattern 2422 each have a continuously changing width as a function of distance along the respective conductive patterns, though the width changes in opposite circular directions for the two patterns. For example, the first conductive pattern 2520 has a wide end 2534 that has a wide width (measured radially from an axis of rotation of the image rotation assembly), and the width decreases with circular distance around the pattern (counter-clockwise in the view of FIG. 25). The first conductive pattern 2520 has a narrow end 2536 having a second width narrower than the width at the wide end 2534. Similarly, the conductive pattern 2522 has a wide end 2538 that has a wide width (again measured in a radial direction), and the width decreases with circular distance around the pattern (clockwise in the view of FIG. 25). The second conductive pattern 2522 has a narrow end 2540 having a narrow width narrower than the width of the wide end 2538. Stated another way, the conductive patterns have a continuously changing width as a function of circular location around the respective conductive patterns, though the width changes in opposite circular directions for the two patterns.

In example systems, the conductive portion 2530 is configured to rotate relative to the base along a circular path over the conductive patterns 2520, 2522, 2532. At any given point along the circular path, the capacitance measurement circuit 2510 measures an electrical parameter between the conductive portion 2530 and the conductive patterns 2520, 2522, and 2532. For example, the capacitance measurement circuit 2510 may measure capacitance as between any of the following combinations: the conductive pattern 2520 and the conductive pattern 2532; the conductive pattern 2522 and the conductive pattern 2532; and the conductive pattern 2520 and the conductive pattern 2522. The example capacitance measurement circuit 2510 generates rotation data where a rotational position of the rotation mechanism corresponds to measured values. As described herein, the rotation data may include absolute position data and angular position data. Rotation data generated may be sent to the processor (e.g., processor 112) and used to process image data generated by the imaging assembly to rotate the image data to account for rotation of the imaging assembly.

In example systems, the conductive portion 2530 may have a width (measured tangent to the circular direction) of about 1 mm, a length (measured parallel to a radial from the axis of rotation of the image rotation assembly) sufficient to cover or reside over all three conductive patterns. In example systems, the first conductive pattern 2520 may have a length of about 100 mm if hypothetically unfolded or unwound into a straight line. The width of the example first conductive pattern 2520 is continuously varied along its length. Similarly, the second conductive pattern 2522 may have a length of about 100 mm if hypothetically unfolded or unwound into a straight line, and the width of the example second conductive pattern 2522 is continuously varied along its length. The continuously varied width creates a straight-line linear relationship between distance along the conductive pattern and an area of the conductive pattern residing beneath the conductive portion 2530. Stated differently, and considering a conductive pattern wound as in FIG. 25A, the continuously varied width creates a straight-line linear relationship between circular location of the conductive portion 2530 and area of the conductive pattern beneath the conductive portion 2530.

Figure 26A:
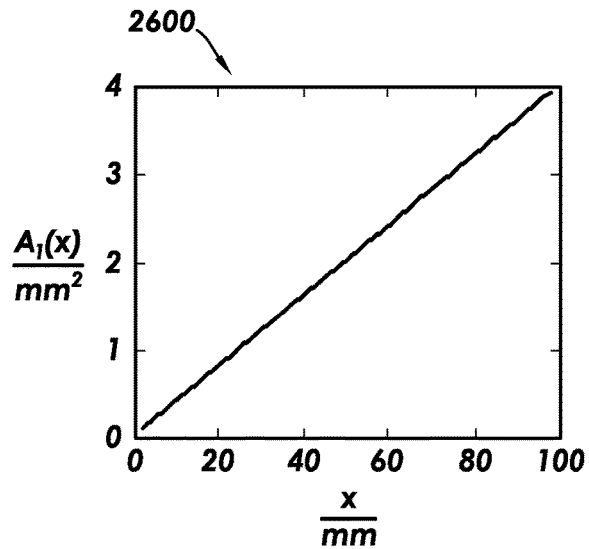
FIG. 26A is a plot of an area $A_1$ of a first conductive pattern as a function of a displacement along the first conductive pattern, in accordance with at least some embodiments.
Figure 26B:
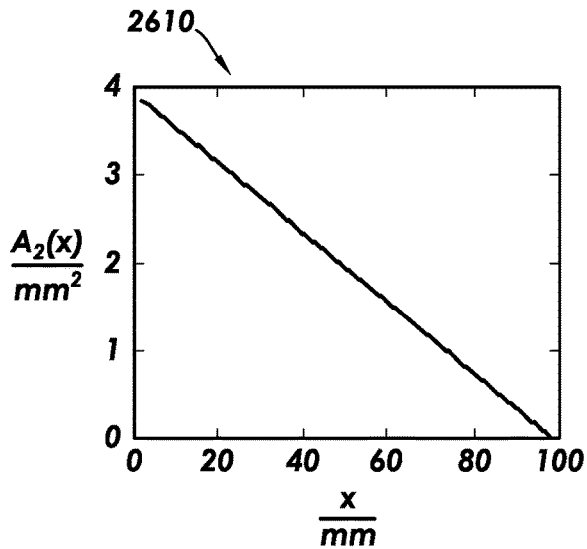
FIG. 26B is a plot of an area $A_2$ of the second conductive pattern as a function of displacement along the second conductive pattern, in accordance with at least some embodiments.

FIG. 26A is a plot 2600 of an area $A_1$ (in mm$^2$) of the first conductive pattern 2520 beneath a rotatable conductive portion (e.g., rotatable conductive portion 2530) as a function of a displacement (e.g., length) x along the first conductive pattern. Stated otherwise, FIG. 26A is a plot of area $A_1$ of the first conductive pattern 2520 beneath the rotatable conductive portion as a function of circular location relative to a predetermined origin (e.g., the narrow end). Similarly FIG. 26B is a plot 2610 of an area $A_2$ (in mm$^2$) of the second conductive pattern 2522 beneath a rotatable conductive portion as a function of displacement x along the second conductive pattern 2522. Stated otherwise, FIG. 26B is a plot of area $A_2$ of the second conductive pattern 2522 beneath the rotatable conductive portion as a function of circular location relative to the predetermined origin (e.g., the wide end). As shown, the areas $A_1$ and $A_2$ are linear functions having opposite slopes. For example, when a rotatable conductive portion (e.g., rotatable conductive portion 2530) is over the widest part of the first conductive pattern 2520 (and thus having the largest area $A_1$), the rotatable conductive portion 2530 may be simultaneously over the narrowest part of the second conductive pattern 2522.

Figure 26C:
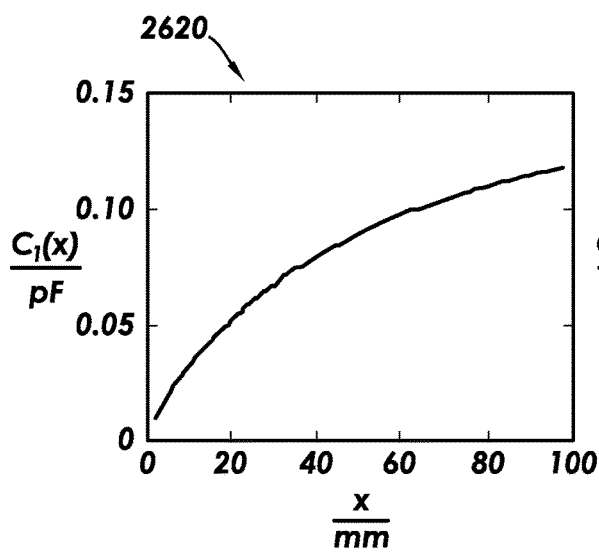
FIG. 26C is a plot of capacitance of the first conductive pattern as a function of displacement along the first conductive pattern, in accordance with at least some embodiments.
Figure 26D:
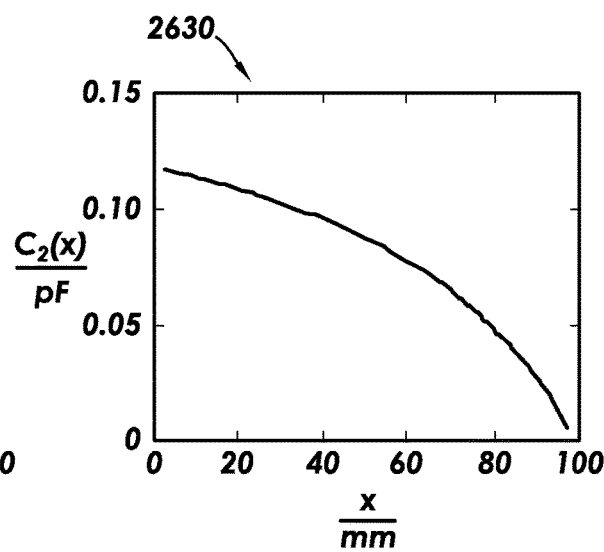
FIG. 26D is a plot of capacitance of the second conductive pattern as a function of displacement along the second conductive pattern, in accordance with at least some embodiments.

FIG. 26C is a plot 2620 of capacitance in pico-Farads (in pF) of the first conductive pattern 2520 as a function of displacement x. Stated otherwise, FIG. 26C is a plot of capacitance $C_1$ of the first conductive pattern 2520 beneath the rotatable conductive portion as a function of circular location relative to the predetermined origin (e.g., the narrow end). FIG. 26D is a plot 2630 of capacitance of the second conductive pattern 2522 as a function of displacement x. Stated otherwise, FIG. 26D is a plot of capacitance $A_2$ of the second conductive pattern 2522 beneath the rotatable conductive portion as a function of circular location relative to the predetermined origin (e.g., the wide end).

In some embodiments, a measured capacitance ($C_1(x)$, $C_2(x)$) of the first conductive pattern 2520 and the second conductive pattern 2522, respectively, may be given by equations (8) and (9):

$$C_1(x) = \frac{C \cdot C1(x)}{C + C1(x)} \quad (8)$$

$$C_2(x) = \frac{C \cdot C2(x)}{C + C2(x)} \quad (9)$$

where C, C1(x), and C2(x) correspond to the capacitance contributions from the rotatable conductive portion 2530, the first conductive pattern 2520, and second conductive pattern 2530, respectively. Equations for C, C1(x), and C2(x) are given by equations (10), (11), and (12):

$$C = \varepsilon_0 \cdot \varepsilon_r \cdot \frac{L_1 \cdot W_1}{d} \quad (10)$$

$$C1(x) = \varepsilon_0 \cdot \varepsilon_r \cdot \frac{A_1(x)}{d} \quad (11)$$

$$C2(x) = \varepsilon_0 \cdot \varepsilon_r \cdot \frac{A_2(x)}{d} \quad (12)$$

where $\varepsilon_0$ is the dielectric constant or permittivity of the air, $\varepsilon_r$ is the relative permittivity of the material between the capacitor plates, A1(x) is the area of the conductive pattern strip 1 at displacement x, A2(x) is the area of the strip 2 at displacement x, and d is the distance between the conductive patterns and the overlay pattern (e.g., conductive portion 2530).

Figure 26E:
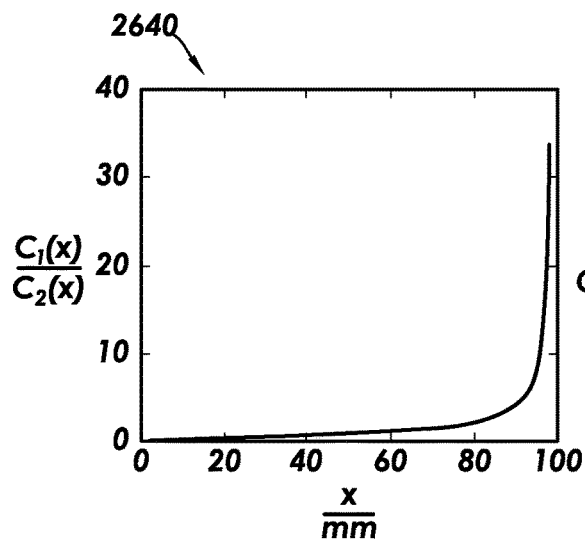
FIG. 26E is a plot of a ratio of the first and second conductive pattern capacitances as a function of displacement along the patterns, in accordance with at least some embodiments.

FIG. 26E is a plot 2640 of a ratio of the first and second conductive pattern capacitances ($C_1(x)/C_2(x)$) as a function of displacement x along the patterns. By taking a ratio of the first and second conductive pattern capacitances, variations due to distance d between the conductive patterns and the conductive portion are canceled in the ratio calculation since those distances are equal for each conductive pattern.

Figure 26F:
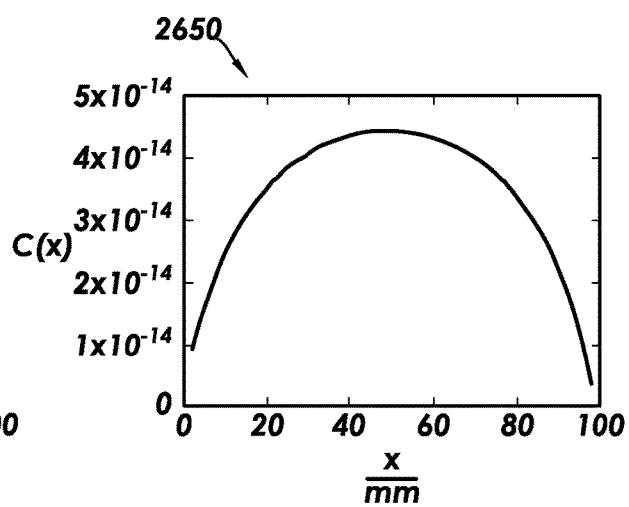
FIG. 26F is a plot of series capacitance corresponding to the first and second conductive patterns, in accordance with at least some embodiments.

In some embodiments, the first and second conductive patterns 2520 and 2522 function as series capacitors due to their proximity. FIG. 26F is a plot 2650 of series capacitance corresponding to the first and second conductive patterns 2520 and 2522 and may be given by Equation 13:

$$C(x) = \frac{C_1(x) \cdot C_2(x)}{C_1(x) + C_2(x)} \quad (13)$$

where C(x) is the series capacitance. Thus, the capacitance measurement circuit 2510 generates rotation data that can provide an absolute position of a rotation mechanism of the image rotation assembly (e.g., a knob), and therefore an absolute position of an imaging assembly of the visualization device.

The various embodiments of the capacitive sensing of rotational orientation of the image rotation assembly discussed to this point have assumed a capacitance-based determination of rotational position of the image rotation assembly. However, using the structure of FIG. 25A determination of rotational position may be equivalently determined in terms of magnitude of an AC voltage developed using the capacitances as a voltage divider. In particular, using the capacitances $C_1$ and $C_2$ as a voltage divider, and for a given interrogation frequency, a magnitude of the AC voltage developed across the voltage divider is indicative of the location of the conductive portion 2530 relative to the conductive patterns 2520 and 2522.

Figure 26G:
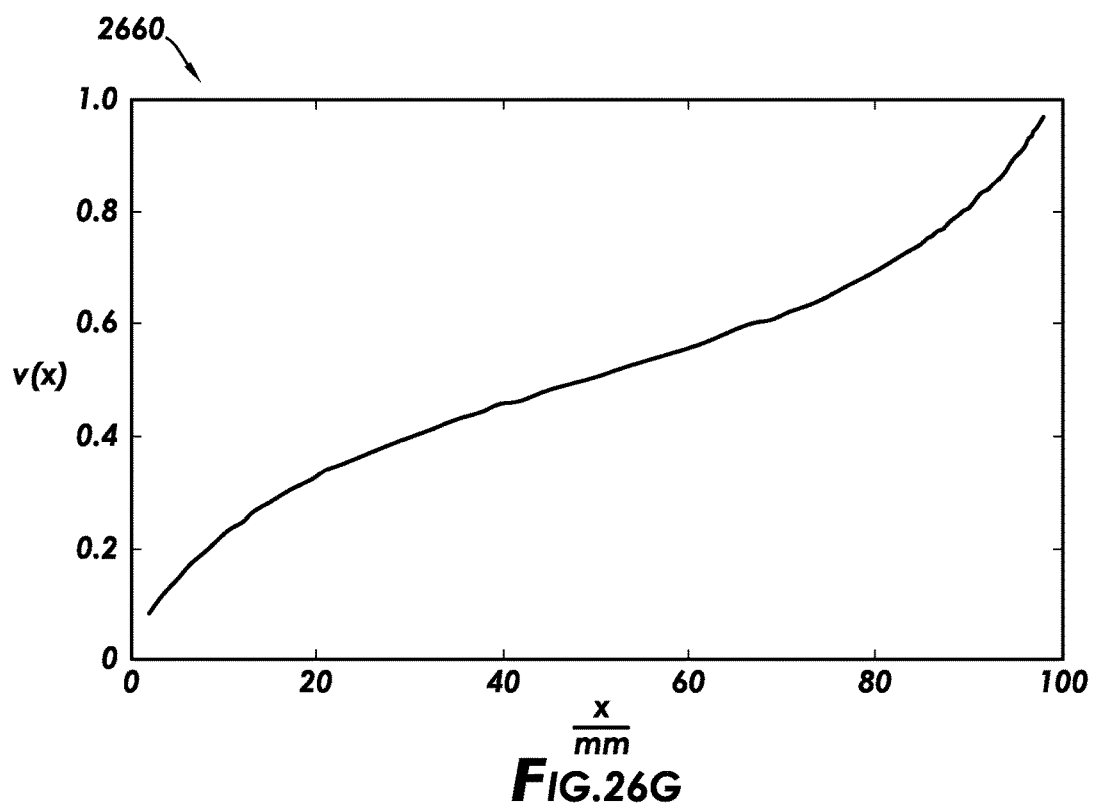
FIG. 26G is a plot of voltage v(x) developed across the first and second conductive patterns operated as a voltage divider, in accordance with at least some embodiments.

FIG. 26G is a plot 2660 of voltage v(x) developed across the first and second conductive patterns 2520 and 2522 operated as a voltage divider. The example voltage v(x)

represents a non-linear function in the sense of being a non-straight line function, but nevertheless there is a direct and distinct relation between the voltage and the distance x (being circular or rotational location). The voltage v(x) may be given by Equation 14:

$$v(x) = \frac{C_1(x)}{C_1(x) + C_2(x)} \quad (14)$$

where $C_1(x)$ and $C_2(x)$ are as defined above.

Figure 27A:
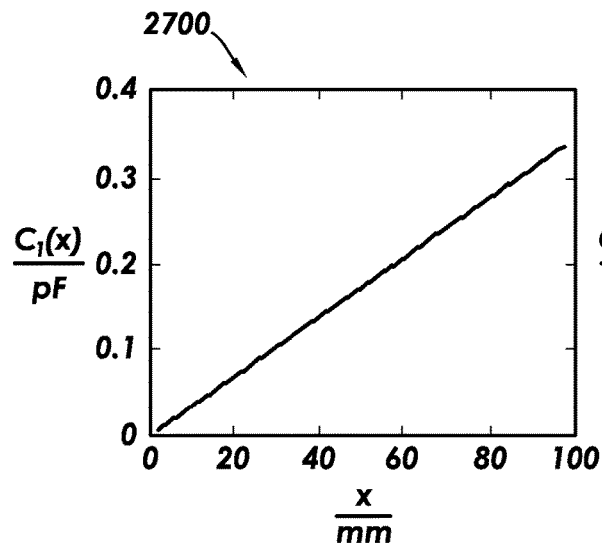
FIG. 27A is a plot of capacitance $C_1$ of a first conductive pattern as a function of a displacement along the first conductive pattern, in accordance with at least some embodiments.
Figure 27B:
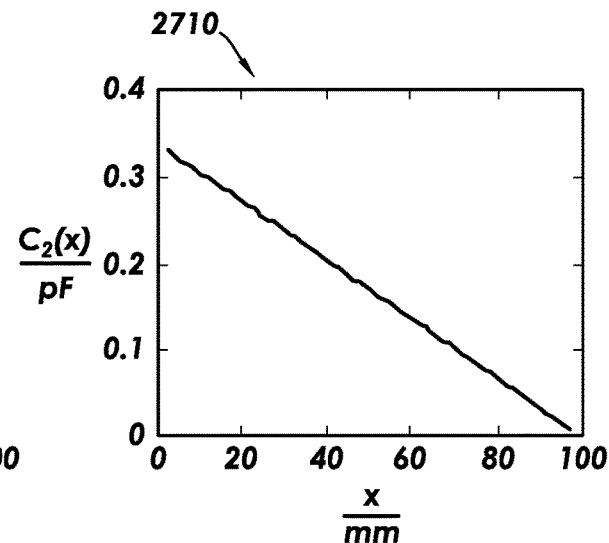
FIG. 27B is a plot of capacitance $C_2$ of the second conductive pattern as a function of displacement along the second conductive pattern, in accordance with at least some embodiments.

FIG. 27A is a plot 2700 of capacitance $C_1$ (in pF) of the first conductive pattern 2520 beneath a rotatable conductive portion (e.g., rotatable conductive portion 2530) as a function of a displacement x along the first conductive pattern. Stated otherwise, FIG. 27A is a plot of capacitance $C_1$ of the first conductive pattern 2520 beneath the rotatable conductive portion as a function of circular location relative to a predetermined origin (e.g., the narrow end). Similarly FIG. 27B is a plot 2710 of capacitance $C_2$ (in pF) of the second conductive pattern 2522 beneath a rotatable conductive portion as a function of displacement x along the second conductive pattern 2522. Stated otherwise, FIG. 27B is a plot of capacitance $C_2$ of the second conductive pattern 2522 beneath the rotatable conductive portion as a function of circular location relative to the predetermined origin (e.g., the wide end). As shown, the capacitance $C_1$ and $C_2$ are linear functions having opposite slopes. For example, when a rotatable conductive portion (e.g., rotatable conductive portion 2530) is over the widest part of the first conductive pattern 2520 (and thus having the largest capacitance $C_1$), the rotatable conductive portion 2530 may be simultaneously over the narrowest part of the second conductive pattern 2522.

Figure 27C:
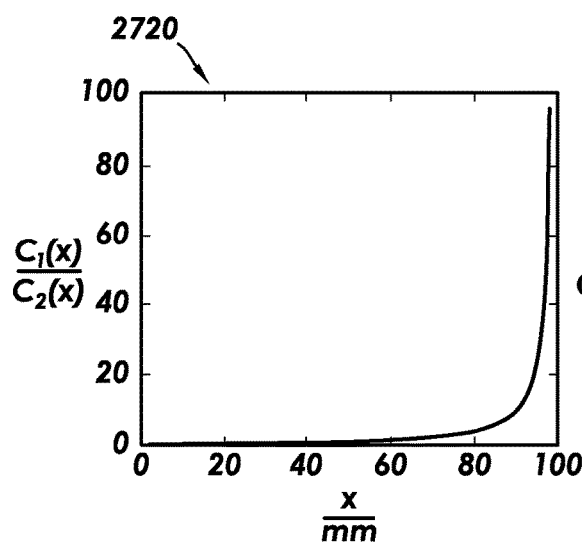
FIG. 27C is a plot of a ratio of the first and second conductive pattern capacitances as a function of displacement along the patterns, in accordance with at least some embodiments.
Figure 27D:
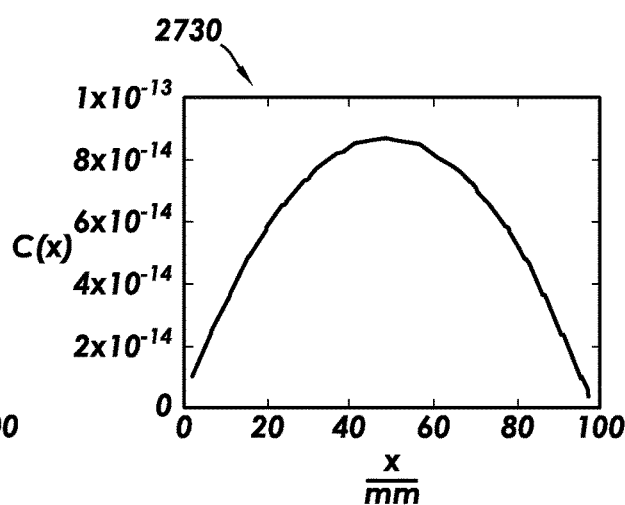
FIG. 27D is a plot of series capacitance corresponding to the first and second conductive patterns, in accordance with at least some embodiments.
Figure 27E:
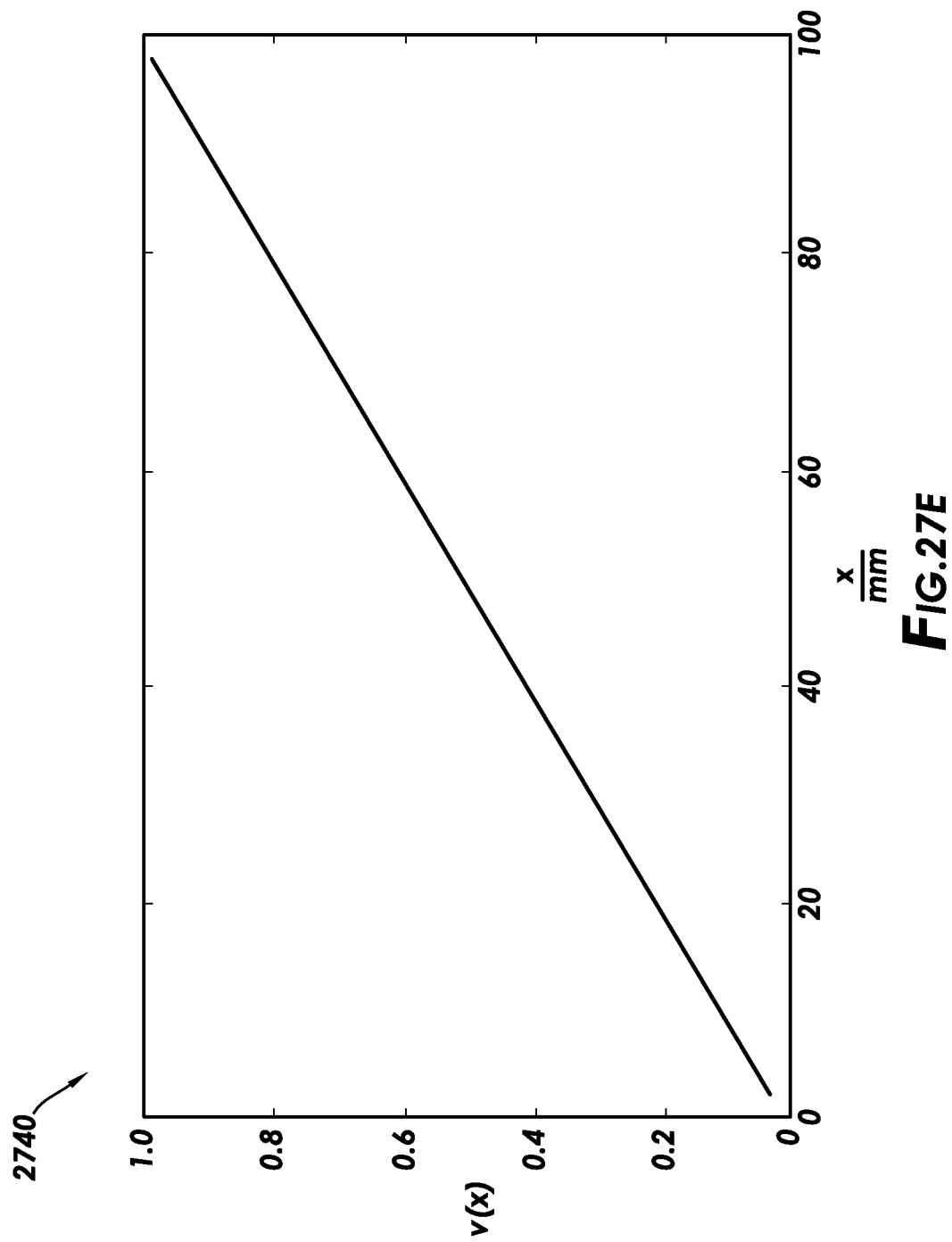
FIG. 27E is a plot of voltage developed across the first and second conductive patterns operated as a voltage divider, in accordance with at least some embodiments.

FIG. 27C is a plot 2720 of a ratio of the first and second conductive pattern capacitances ($C_1(x)/C_2(x)$) as a function of displacement x along the patterns. By taking a ratio of the first and second conductive pattern capacitances, variations due to distance d between the conductive patterns and the conductive portion are canceled in the ratio calculation. FIG. 27D is a plot 2730 of series capacitance corresponding to the first and second conductive patterns 2520 and 2522, and may be given by Equation 13 above. FIG. 27E is a plot 2740 of voltage v(x) developed across the first and second conductive patterns 2520 and 2522 operated as a voltage divider. In particular, in the example of FIG. 27E the relative widths of the underlying conductive patterns 2520 and 2540 are designed and constructed to provide a linear (e.g., here straight-line) relationship of the voltage developed across the capacitances $C_1$ and $C_2$ operated as a voltage divider. Stated otherwise, in the example of FIG. 27E the relative capacitances of the underlying conductive patterns 2520 and 2540 are designed and constructed to provide a linear relationship of the voltage developed across the capacitances $C_1$ and $C_2$ operated as a voltage divider.

Returning to FIG. 25A. In some cases, the capacitive measurement circuit 2510 measures the capacitance of each conductive pattern individually by way of the circular conductive pattern 2532 and the conductive portion 2530. Consider, as an example, that an AC signal is applied to the circular conductive pattern 2532. The signal passes across the capacitance formed between the conductive pattern 2532 and the conductive portion 2530, and then the signal passes across the capacitance formed between the conductive portion 2530 and the conductive pattern being measured, and then returns to the capacitive measurement circuit 2510. Based on an electrical property (e.g., voltage, current, phase angle) of the signal that returns to the capacitive measurement circuit 2510, and the fact the capacitance formed between the conductive pattern 2532 and the conductive portion 2530 is constant for any rotational position of the conductive portion 2530, the capacitance formed between the conductive portion 2530 and the conductive pattern being measured can be determined.

However, for series capacitance, the net capacitance is largely controlled by the smallest in the series connection. I the example system shown in FIG. 25A, at some rotational positions (e.g., the conductive portion being at the position of the lead line for reference number 2534), the capacitance formed between the conductive portion 2530 and the conductive pattern being measured is larger than the capacitance formed between the conductive pattern 2532 and the conductive portion 2530. In the example situation given, it may be difficult in some circumstances for the capacitive measurement circuit 2510 to accurately measure the capacitance formed between the conductive portion 2530 and the conductive pattern being measured when the constant capacitance associated with the conductive pattern 2532 and conductive portion 2530 is smaller.

FIG. 25B shows is a schematic diagram of a sensor of an image rotation assembly. In FIG. 25B, the rotating portion includes not only conductive portion 2530, but an additional electrically-integral circular conductive pattern 2490 coupled to the knob (not shown). The conductive pattern 2490 resides directly above the conductive pattern that runs around the interior of the conductive patterns 2520 and 2522 (not shown, but see conductive pattern 2532 of FIG. 25A). In this way, the capacitance associated with the rotating portion of the sensor (e.g., the knob) is larger at all measurement locations/rotations than the capacitance formed between the conductive portion 2530 and the conductive pattern being measured. The capacitive measurement circuit 2510 may more easily and accurately determine the desired capacitance.

While the conductive patterns and portions in the examples above (e.g., conductive patterns 2520, 2522, 2530) are described as having specific dimensions, it can be appreciated that other dimensions can be used, for example, to accommodate different sized image rotation assembly components (e.g., different sized knob diameters), to adjust linearity and/or sensitivity.

iv. Wire Management Assembly

Returning briefly to FIG. 1, in some embodiments a wire management assembly 128 may be used and configured to provide a wired connection between the imaging assembly 122 and one or more components of the device (e.g., base, display, processor, power circuit) while enabling rotation of the imaging assembly 122 relative to the device. Due to the rotation of the imaging assembly 122, the wired connections described herein may be configured for dynamic and controlled movement to ensure electrical and/or communicative connectivity between the imaging assembly 122 and the control device 110. The wire management assembly 128 may enable a loop of communicative conductors (e.g., electrical conductors, optical conductors) to service the rotation of the image rotation assembly 124 and control parameters such as tension, friction, and translation of the communicative conductors. For example, as a wired connection translates along its predetermined path, a predetermined amount of tension may be maintained to reduce kinking and wear while providing predictability of the movement of the wired connection. In some embodiments, the wire management assembly 128 may include a rotating pinion service loop mechanism.

Figure 35A:
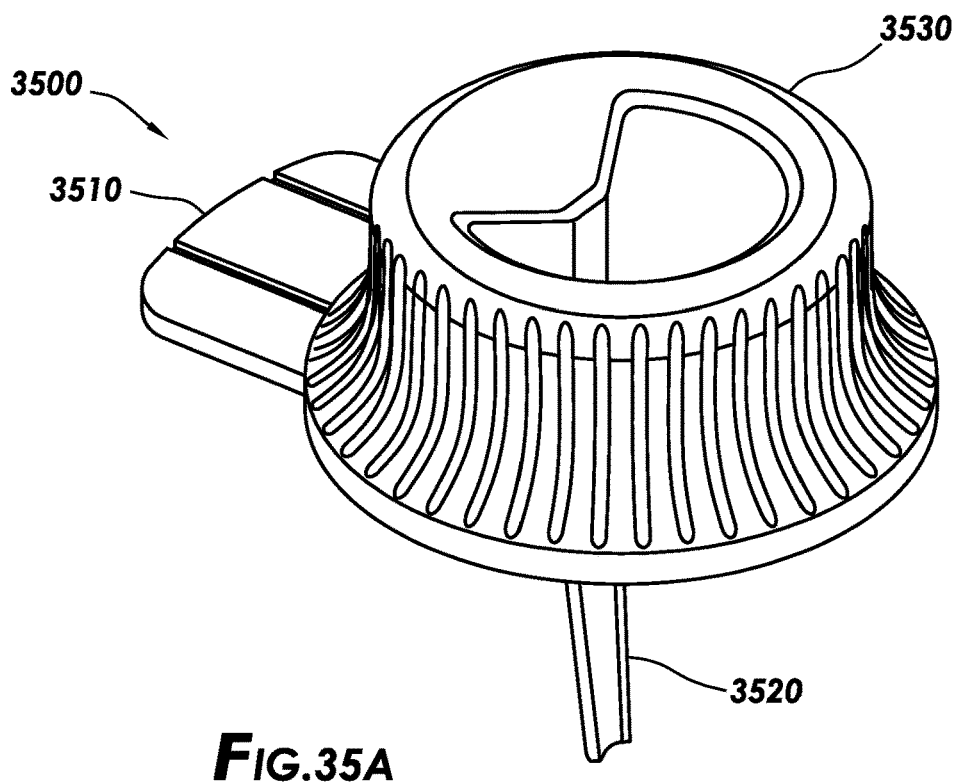
FIG. 35A is a perspective view of a visualization device in accordance with at least some embodiments.

FIG. 35A is a perspective view of a visualization device 3500 in accordance with at least some embodiments. In particular, FIG. 35A shows a base 3510, an imaging assembly 3520, and a rotation mechanism or knob 3530. The imaging assembly 3520 and knob 3530 are rotatably coupled to the base 3510. For example, the imaging assembly 3520 may be rigidly coupled to the knob 3530 such that as the knob 3530 is turned, the imaging assembly orbits or translates around the axis of rotation of the knob 3530. In example embodiments, the knob 3530 encloses a wire management system (not visible in FIG. 35A).

Figure 35B:
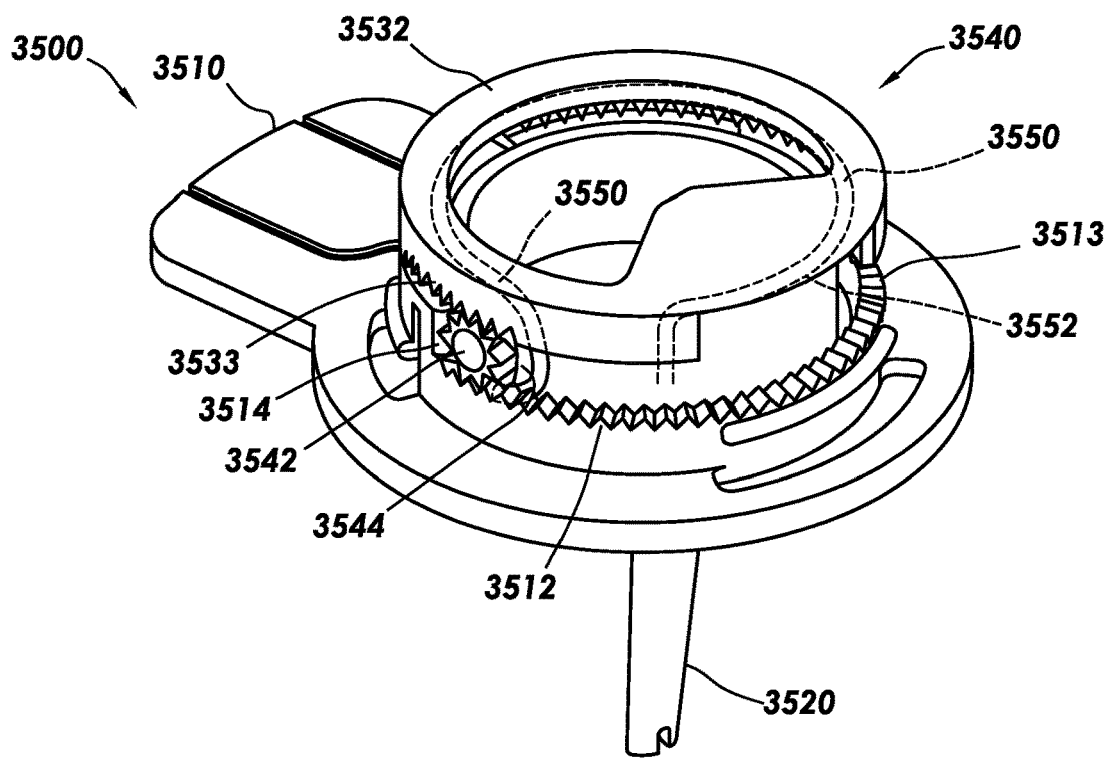
FIG. 35B is a partial perspective view of the visualization device, with the knob removed to reveal a wire management system, in accordance with at least some embodiments.

FIG. 35B is a partial perspective view of the visualization device, with the knob removed to reveal a wire management system 3540. In particular, the example wire management system 3540 may be disposed between the knob and the base 3510. In example embodiments the knob encloses the wire management system 3540 such that the wire management system 3540 is not visible to the clinician during use.

The example wire management system 3540 comprises a stationary circular rack 3512 rigidly coupled to the base 3510, and a rotatable circular rack 3532 rigidly coupled to the knob and the imaging assembly 3520. Thus, as the knob is turned relative to the base 3510, the rotatable circular rack 3532 turns relative to the stationary circular rack 3512. The stationary circular rack 3512 defines a plurality of upward pointing teeth 3513 that form the gear or rack. The rotatable circular rack 3532 defines a plurality of downward pointing teeth 3533 that form the gear or rack.

The example wire management assembly 3540 further comprises a pinion 3542 disposed between the stationary circular rack 3512 and the rotatable circular rack 3532. In particular, teeth of the pinion 3542 interact with the teeth 3513 of the of the stationary circular rack 3512 and interact with the teeth 3533 of the of the rotatable circular rack 3532. In use, the pinion 3542 is configured to translate between the stationary circular rack 3512 and the rotatable circular rack 3532 along a circular path defined by the racks 3512 and 3532. In the example system shown, the pinion 3542 is abutting a stop 3514 which prevents further rotation of the knob in the clockwise direction (in the view of FIG. 35B). From the position shown in FIG. 35B, as the knob is turned in the counter-clockwise direction (in the view of FIG. 35B), the pinion 3542 translates along the stationary circular rack 3512 in the counter-clockwise direction.

The example wire management system 3540 further comprises a service loop, gear flange, or wire channel 3544 coupled to the pinion 3542 and configured to translate along the circular path with the pinion 3542. In example cases, the wire channel 3544 takes the form of a circular disk having an annular channel defined on an outside diameter of the circular disk. The annular channel is designed and constructed to accommodate and translate a communication cable or cable bundle 3550 as the knob and imaging assembly 3520 are turned by the clinician. In some cases, the wire channel 3544 is rigidly coupled to the pinion 3542 such that the wire channel 3544 turns about a shared rotational axis as the pinion 3542 turns and translates around the circular path. In other cases, the wire channel 3544 is coupled (e.g., by way of a bearing) such that relative rotational motion between wire channel 3544 and pinion 3542 along a shared rotational axis is possible. In such circumstances, turning of the wire channel 3544 about the shared rotational axis is caused by movement of the cable bundle 3550.

Referring simultaneously to FIGS. 35A and 35B, in the example system the pinion 3542 translates along a 180 angular degree circular path as the knob 3530 and rotatable circular rack 3532 are turned. As mentioned above, FIG. 35B shows the pinion 3542 abutting the stop 3514, and thus FIG. 35B shows the example system in the clock-wise most orientation of the knob 3530 and rotatable circular rack 3532.

Figure 35C:
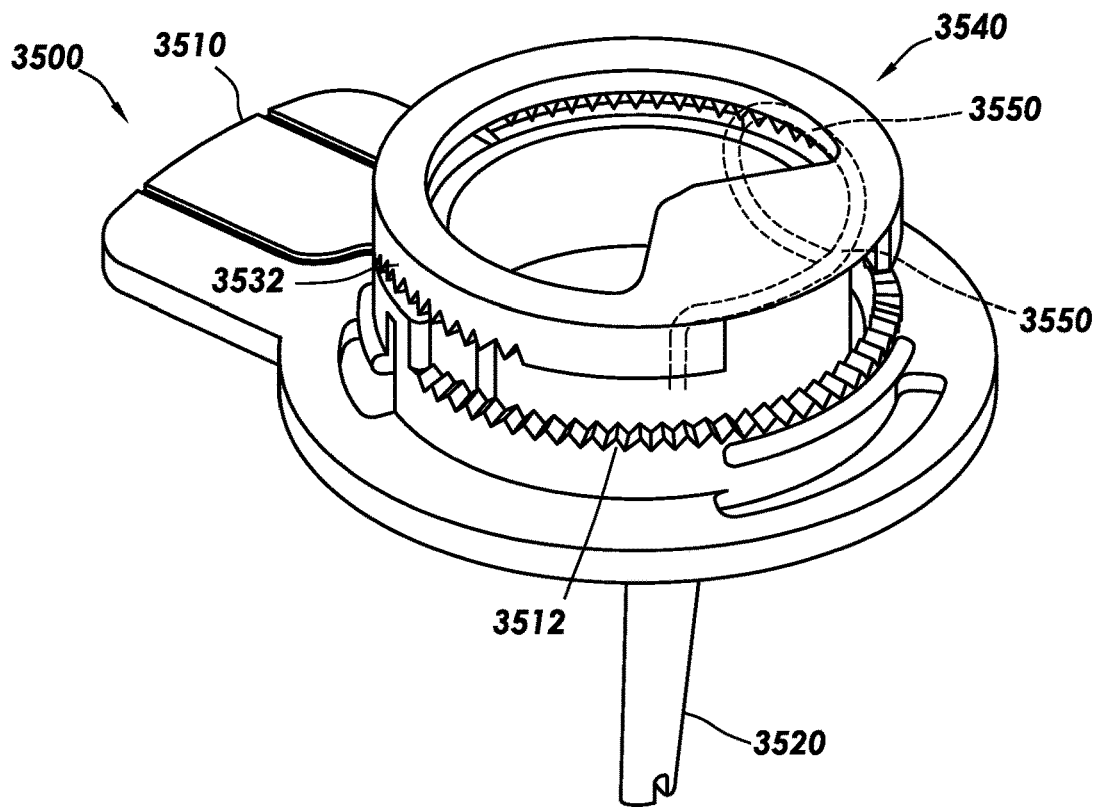
FIG. 35C is a partial perspective view of the visualization device, with the knob removed to reveal a wire management system, in accordance with at least some embodiments.

FIG. 35C is a partial perspective view of the visualization device 3500, again with the knob removed to reveal a wire management system 3540, and also wire management system 3540 rotated such that the pinion is translated 180 angular degrees relative to FIG. 35B. In particular, in FIG. 35C the pinion (not visible) is abutting a second stop (not visible) which prevents further rotation of the knob in the counter-clockwise direction (in the view of FIG. 35C). In the example system shown, and from the position shown in FIG. 35C, as the knob and rotatable circular rack 3532 are turned in the clockwise direction the pinion translates along the stationary circular rack 3512 in the clockwise direction.

Returning to FIGS. 35A and 35B, regardless of travel direction of the pinion 3542, tension of the cable bundle 3550 over the wire channel 3544 may be maintained at approximately zero throughout a translation path of the pinion 3542. For example, the cable bundle 3550 maintains a "U" shape around the wire channel 3544 as the rotation mechanism rotates.

The example wire management assembly 3540 is configured to translate a predetermined length of the cable bundle 3550 about the pinion 3542 and wire channel 3544. A first portion of the cable bundle 3550 is fixed to a first predetermined position in the base 3510 (e.g., such as pressed within and running along the unnumbered slots in the base as shown in FIG. 35B). A second portion of the cable bundle 3550 may be fixed to a second predetermined position 3552 in one or more rotation components. For example, the second portion of the cable bundle 3550 may be fixed to a proximal portion of the imaging assembly 3520 as shown. While the cable bundle 3550 translates with the movement of the pinion 3542, the overall length of the cable bundle 3550 remains the same and enables more consistent and predictable wear of the cable bundle 3550. In other words, the total length of the cable bundle 3550 remains constant, but a length of the cable bundle 3550 on either side of the pinion 3542 (e.g., above, below) changes based on a position of the knob and the rotatable circular rack 3532.

In example systems, a diameter of the wire channel 3544 may be based on a minimum bend radius of the cable bundle 3550. The cable bundle 3550 may have a diameter of about 1 mm to about 2.5 mm. The wire channel 3544 may have a diameter of about 5 mm to about 20 mm. The pinion 3542 may have a diameter of about 5 mm to about 15 mm. In some embodiments, the pinion 3542 may have a gear ratio that translates the pinion 3542 to a smaller degree relative to rotation of the knob 3530. For example, the pinion 3542 may be configured to translate along about 0.5 degrees of its circular path for every 1 degree of rotation of the knob 3530 and rotatable circular rack 3532. Such a configuration enables a predetermined length of the translated cable bundle 3550 to be reduced relative a travel path of the knob 3530 in order to form a compact wire management assembly 3540 and reduce wear over time. Furthermore, a cable bundle 3550 having a reduced length may reduce signal noise generated by, for example, manipulation of the cable bundle 3550.

Figure 35D:
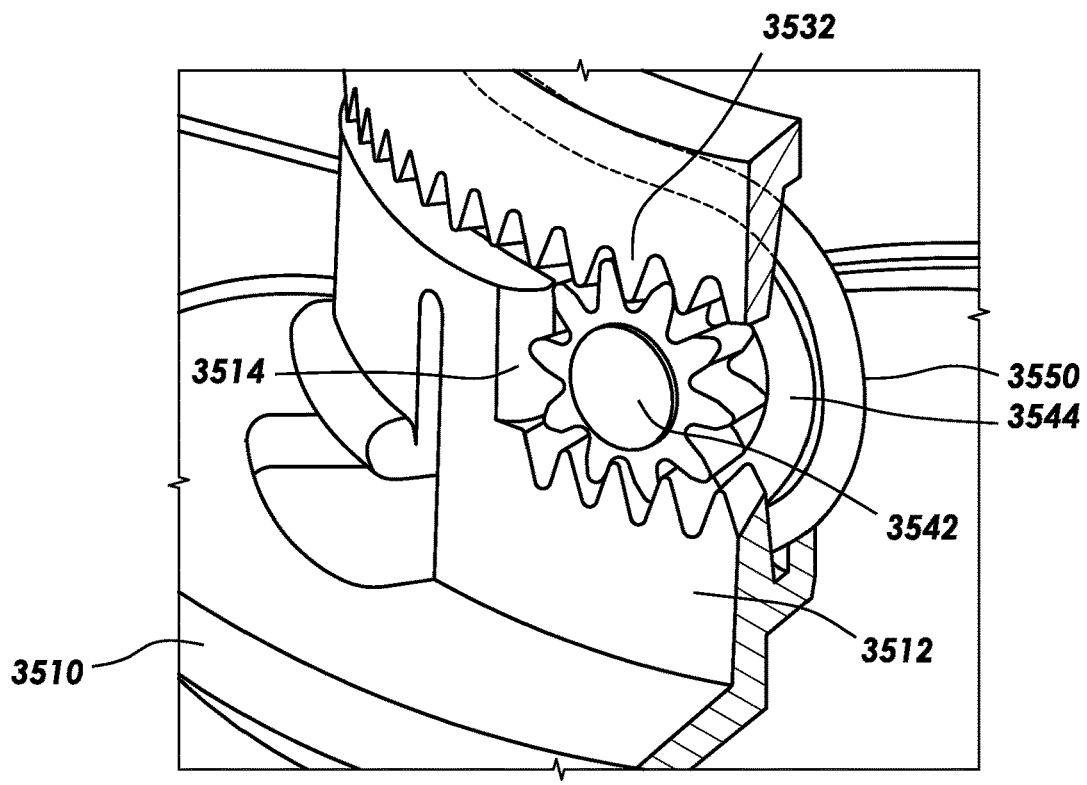
FIG. 35D is a partial perspective view of the visualization device, with the knob removed to reveal a wire management system, and in accordance with at least some embodiments.

FIG. 35D is a partial perspective view of the visualization device in greater detail, again with the knob removed to reveal the wire management system, and in accordance with at least some embodiments. In particular, better shown in FIG. 35D is a portion of the stationary circular rack 3512, a portion of the rotatable circular rack 3532, and the pinion 3542 disposed between the racks. Further visible is the wire channel 3544 having the cable bundle 3550 partially circumscribing the wire channel 3544. FIG. 35D shows the pinion 3542 abutting the stop 3514, thus limiting the rotational travel in the clockwise direction (in the view of FIG. 35D). In example cases, the pinion 3542 has an axis of rotation. Though the axis of rotation of the pinion 3542 changes location relative the base 3510 as the pinion 3542 translates along the circular path, in example systems the axis of rotation intersects, at all times, an axis of rotation of the rotatable circular rack 3532 and knob. In some cases the axis of rotation of the rotatable circular rack 3532 and knob 3530 is coaxial with a longitudinal axis of a speculum (not shown in FIG. 35D).

Figure 36A:
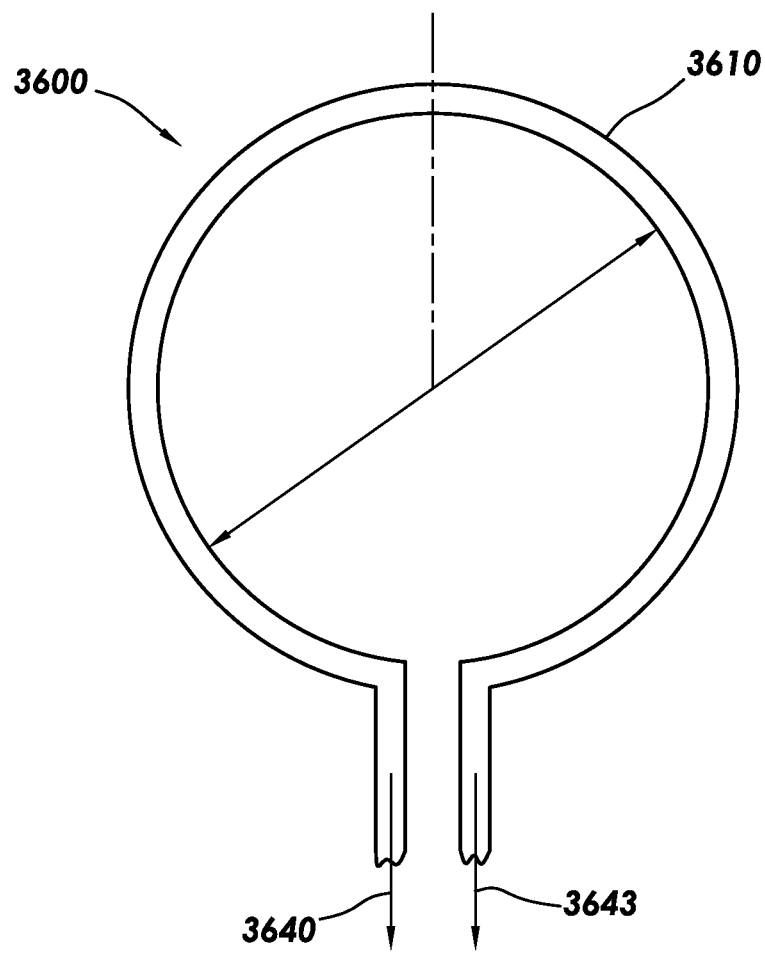
FIG. 36A is a schematic plan view of an alternative wire management assembly in accordance with at least some embodiments.
Figure 36B:
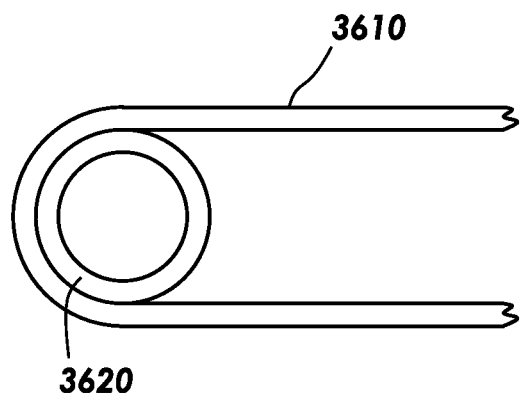
FIG. 36B is a schematic side view of a wire management assembly of a visualization system, in accordance with at least some embodiments.

FIG. 36A is a schematic plan view of an alternative wire management assembly 3600 that includes a wired connection such as a communication cable in the form of a flex circuit 3610. FIG. 36B is a schematic side view of a wire management assembly of a visualization system, in accordance with at least some embodiments. Referring simultaneously to FIGS. 36A and 36B, the flex circuit 3610 may be looped around a pinion 3620. A first end 3630 of the flex circuit 3610 may be fixed to a base (not shown for the sake of clarity) and a second end 3640 of the flex circuit 3610 may be fixed to an imaging assembly (not shown for the sake of clarity). A diameter of the pinion may be based on a minimum bend radius of the flex circuit 3610 which may depend on a number of layers of the flex circuit.

Figure 37:
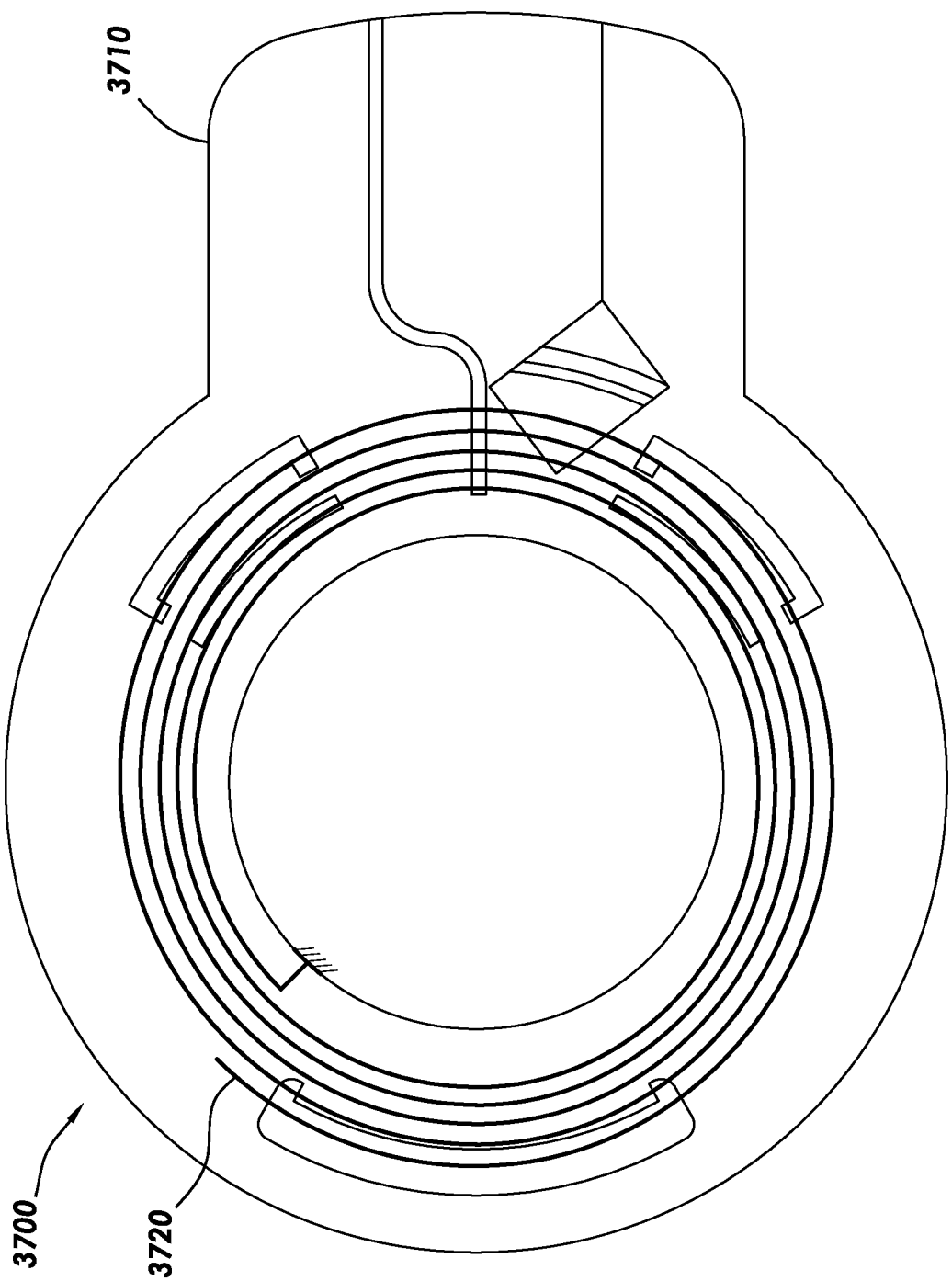
FIG. 37 is a plan view of a visualization system including a base and a wired connection in the form of a flex circuit coil in a spiral configuration, in accordance with at least some embodiments.

FIG. 37 is a plan view of a visualization system 3700 including a base 3710 and a communication cable in the form of a flex circuit coil 3720 in a spiral configuration oriented perpendicular to the base 3710. From a zero position, the flex circuit coil 3720 may be configured to tighten as the rotation mechanism is rotated towards fully rotated orientation (e.g., 360 degree rotation of a knob). Physical stops may act as barriers to rotation at the ends of the circular travel. Furthermore, the flex circuit coil 3720 may be configured to have a tensile load below a predetermined threshold (e.g., before the flex circuit coil 3720 is damaged) when the flex circuit coil 3720 is tightened.

C. Control Device

Referring again to FIG. 1, the example control device 110 may be coupled to a speculum 130 and/or a visualization device 120, and provide processing and/or communication capabilities for facilitating visualization of an ear canal and tympanic membrane during a procedure using one or more instruments (e.g., a tympanostomy tube delivery device). For example, a control device 110 operatively coupled to a speculum 130 may be configured to process and output image data on a display. The control device 110 may be removably coupled to other components of a visualization system and be reusable. The control device 110 of the visualization system 100 may include a display 111, a processor 112, a memory 113, a power circuit 114, and a communication device 115. Each will be addressed in turn.

i. Display

Image data generated by an imaging assembly 122 may be output on the display 111. In some embodiments, the display 111 may be implemented as a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

In some embodiments, the display 111 may include and/or be operatively coupled to an input device (e.g., touch screen) configured to receive input data from the clinician. For example, input to an input device (e.g., keyboard, buttons, touch screen) may be received and processed by the processor 112 and memory 113 of the visualization system 100. The input device may include at least one switch configured to generate a control signal. For example, an input device may include a touch surface for a clinician to provide input (e.g., finger contact to the touch surface) corresponding to a control signal. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In the example case of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

In some embodiments, the visualization system may optionally include one or more output devices in addition to the display 111, such as, for example, an audio device and haptic device. An audio device may audibly output any patient data, sensor data, system data, alarms, and/or notifications. For example, the audio device may output an audible alarm when a malfunction in the imaging assembly is detected. In some embodiments, an audio device may be implanted as a speaker, a piezoelectric audio device, a magnetostrictive speaker, and/or digital speaker. In some embodiments, a clinician may communicate with other users using the audio device and a communication channel. For example, an operator may form an audio communication channel (e.g., VoIP call).

Additionally or alternatively, the system may include a haptic device configured to provide additional sensory output (e.g., force feedback) to the operator. For example, a haptic device may generate a tactile response (e.g., vibration) to confirm operator input to an input device (e.g., touch surface). As another example, haptic feedback may notify that operator input is overridden by the processor.

ii. Processor

The processor 112 described here may process data and/or other signals to control one or more components of the system (e.g., imaging assembly 122). The processor 112 may be configured to receive, process, compile, compute, store, access, read, write, and/or transmit data and/or other signals. Additionally, or alternatively, the processor may be configured to control one or more components of a device (e.g., display 111).

In some embodiments, image processing of image data may include applying a non-linear two-dimensional filter configured to reduce a brightness at an edge of an image. This may reduce glare due to reflection from tissue (e.g., ear canal) and increase visibility of the target treatment area (e.g., tympanic membrane). In one example case, a gain of an image luminance plane may be reduced toward a perimeter of the image data, with higher gain centered within the image luminance plane, and lower gain with increasing distance from a center of the image luminance plane. In other cases, the image luminance plane may conceptually divided into a higher gain inner region, and lower gain outer region.

In some embodiments, the processor 112 may be configured to access or receive data and/or other signals from the imaging assembly and a storage medium (e.g., memory 113, flash drive, memory card). In some embodiments, the processor 112 may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor 112 may be, for example, a general purpose processor, Field Programmable Gate Array (FPGA), an Application Specific Integrated Circuit (ASIC), a processor board, and/or the like. The processor 112 may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

iii. Memory

The visualization system described herein may include a memory 113 configured to store data and/or information. In some embodiments, the memory 113 may include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory may store instructions to cause the processor 112 to execute modules, processes, and/or functions associated with the device, such as image processing, image display, data and/or signal transmission, data and/or signal reception, and/or communication. Some embodiments described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some embodiments, the memory 113 may be configured to store any received data and/or data generated by the device. In some embodiments, the device may be configured to store one or more of image data and patient data (e.g., diagnosis information, surgery or procedure data, and the like), combinations thereof, and the like. In some embodiments, the memory 113 may be configured to store image data including 2D, 3D, and any other data generated from imaging of the patient. In some embodiments, the memory 113 may be configured to store data temporarily or permanently.

iv. Power Circuit

The example power circuit 114 may be configured to receive wired or wireless power. For example, a power circuit 114 may be configured to receive wireless electrical power and convert the received power into usable energy for powering the device. In some embodiments, the power circuit 114 may include one or more energy storage elements (e.g., battery, capacitor) configured to store energy. The power circuit 114 may be further configured to control (e.g., regulate, limit) the power provided to one or more components (e.g., circuit blocks) of the device.

In some embodiments, the power circuit 114 may convert AC voltage at the terminals of a transducer into a DC voltage. In some embodiments, the power circuit 114 may include a rectifier configured to generate a DC voltage rail. The rectifier may include a passive rectifier, active rectifier, passive voltage doubler, and/or combinations thereof. In some embodiments, the power circuit 114 may include a DC-DC converter configured to generate one or more DC voltage rails from the rectifier DC voltage rail. In some embodiments, the power circuit 114 may include a voltage regulator (e.g., a low-dropout regulator (LDO) circuit, a voltage clamp circuit) configured to generate a regulated or constant DC voltage rail. In some embodiments, the power circuit 114 may include one or more reference generation circuits such as a current reference circuit, a bandgap reference circuit, a voltage reference circuit, and/or combinations thereof.

In some embodiments, the power circuit 114 may include an energy storage device having one or more of a capacitor, a super-capacitor, a rechargeable battery, and/or combinations thereof. In some embodiments, the power circuit 114 may not include or omit an energy storage device, and the visualization system 100 may be continuously powered by another device. In some embodiments, power may be provided to the device until it completes its functions and the device may remain inactive until it is powered again. A power circuit 114 without an energy storage device may enable reduction in the size of the power circuit 114 and the overall device.

v. Communication Device

In some embodiments, the control device 100 may include a communication device 115 configured to communicate with other devices. The communication device 115 may be configured to connect the control device 100 and thus the visualization system 100 to another system (e.g., Internet, remote server, database) by wired or wireless connection. In some embodiments, the visualization system 100 may be in communication with other devices via one or more wired and/or wireless networks. In some embodiments, the communication device 115 may include a radiofrequency (RF) receiver, transmitter, and/or optical (e.g., infrared) receiver and transmitter configured to communicate with one or more devices and/or networks. The communication device 115 may communicate by wires and/or wirelessly.

The communication device 115 may include RF circuitry configured to receive and send RF signals. The RF circuitry may convert electrical signals to/from electromagnetic signals and communicate with communications networks and other communications devices via the electromagnetic signals. The RF circuitry may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some embodiments, the devices herein may directly communicate with each other without transmitting data through a network (e.g., through NFC, Bluetooth, WiFi, RFID, and the like).

In some embodiments, the systems, devices, and methods described herein may be in communication with other wireless devices via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication.

II. METHODS

Also described are methods to visualize tissue using the systems and devices described. In particular, the systems, devices, and methods described herein may be used to visualize an instrument and an ear canal as a clinician performs an otological procedure (e.g., a tympanostomy tube delivery, a myringotomy, wax removal, foreign body removal, etc.). The methods described here may include, for example, attaching a speculum 130 to a scope (e.g., visualization device 120 and control device 110), inserting the speculum 130 into an ear canal, and illuminating and/or visualizing the ear canal and/or tympanic membrane. An instrument may be inserted into the ear canal through the speculum, e.g., through an instrument lumen as described above. The clinician may perform a procedure using the instrument and rotating the speculum while image data is displayed on the display 111. The image data may be rotated to be presented in a predetermined orientation regardless of rotation of the speculum 130 by the image rotation assembly 124.

Figure 29:
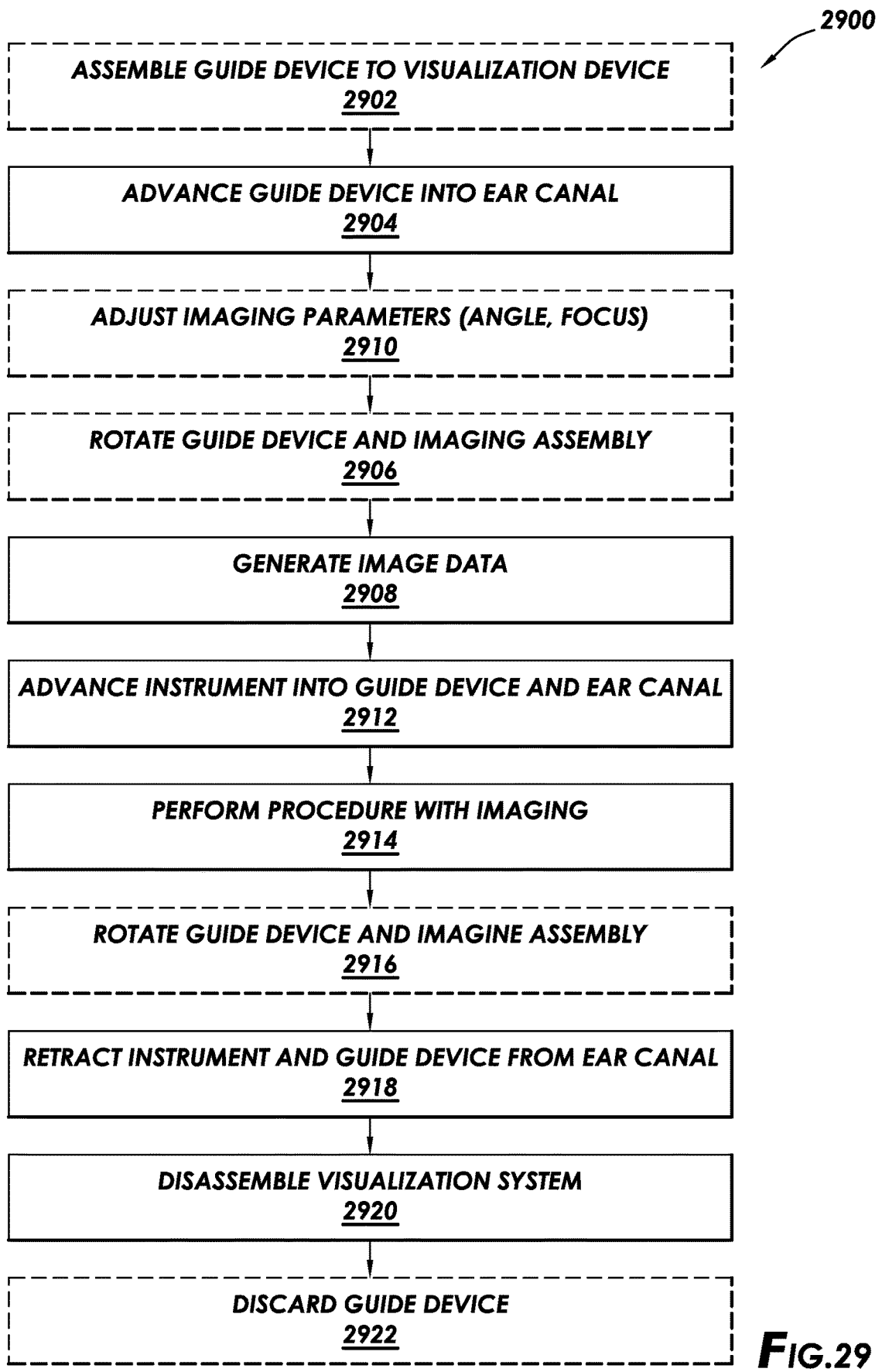
FIG. 29 is an example method of tissue visualization in accordance with at least some embodiments.

FIG. 29 is an example method 2900 of tissue visualization. The example method 2900 optionally includes assembly of a speculum to a visualization device (block 2902). For example, a speculum can be assembled together with a scope such that an imaging assembly of the scope extends into an imaging lumen of the speculum. In some embodiments, the speculum and visualization device can be provided pre-assembled. The speculum may be advanced into an ear canal (block 2904). Imaging parameters may optionally be adjusted (block 2910). For example, a clinician may provide input (e.g., to a touchscreen or other input device) to control focus, resolution, brightness, and the like. The speculum (and therefore an imaging assembly of the visualization device) optionally can be rotated relative to other portions of the visualization device, e.g., to change a field of view of the ear canal (block 2906). The device may generate image data for a display (block 2908). An instrument (e.g., tympanostomy tube delivery device, a suction device, and/or other types of devices for performing otologic procedures such as, for example, placement of a tympanostomy tube, removing fluids, cerumen, or foreign objects, etc., or delivering therapeutic substances) may be advanced into the ear canal through the visualization device and speculum (block 2912). A procedure may be performed using the instrument while the image data is displayed (block 2914). The speculum may optionally be rotated while using the instrument, e.g., to adjust a range of motion of the instrument (block 2916). The instrument and speculum may be retracted from the ear canal (block 2918). The speculum may be disassembled from the visualization device (block 2920). Optionally, if the speculum is a disposable component, the speculum may be discarded (block 2922). Alternatively, the speculum can be disinfected using known disinfection procedures for another use.

FIG. 30 is an example method 3000 of image processing for visualization of a target treatment area. The method 3000 includes rotating a speculum relative to a visualization system (block 3002). The visualization system may generate image data (block 3004). The image data may be generated by, for example, an imaging assembly as described herein. The visualization system may further generate rotation data corresponding to the speculum (block 3006), and/or generate orientation data corresponding to the clinician (block 3008). The rotation data and/or orientation data may be generated by, for example, an image rotation assembly, as described herein. The image data may be processed based on one or more of the rotation data and orientation data (block 3010). In this manner, the image data may have a consistent, predetermined orientation (e.g., from a perspective of the clinician) that may aid in visualization. The image data may be output (block 3012), such as on a display of the visualization system.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A visualization system comprising:
   a control device defining an upper surface and a lower surface;
   a display visible through the upper surface of the control device;
   a handle coupled to the lower surface and extending away from the lower surface;
   a knob coupled to the control device, the knob configured to rotate about a rotational axis;
   an imaging assembly mechanically coupled to the knob and communicatively coupled to the control device, the imaging assembly configured to rotate around the rotational axis based on rotation of the knob, the control device configured to display an image on the display, the image captured by the imaging assembly;
   a rotation sensor in operational relationship to the knob and communicatively coupled to the control device, the rotation sensor configured to sense rotation of the knob and the imaging assembly;
   wherein the control device is configured to rotate the image on the display responsive to rotation of the knob such that the image remains in a consistent orientation relative to the display despite rotation of the image assembly.

2. The visualization system of claim 1 further comprising:
   a post defining a proximal end and a distal end, the proximal end of the post coupled to the lower surface of the control device, and the post extending away from the lower surface;
   a base coupled to the distal end of the post, the base defining an upper surface, a lower surface, and an aperture;
   the knob disposed on the upper surface of the base; and
   the imaging assembly extending through the aperture and below the lower surface of the base.

3. The visualization system of claim 1 wherein the imaging assembly further comprises:
   an elongate shaft defining a proximal end and a distal end, the proximal end rigidly coupled to the knob;
   an optical sensor disposed within the elongate shaft, the optical sensor defining an optical axis, and the optical sensor communicatively coupled to the control device; and
   an illumination source disposed within the elongate shaft;
   wherein the optical axis forms a non-zero angle with the rotational axis of the knob.

4. The visualization system of claim 1 further comprising a communication cable coupled between the imaging assembly and the control device, the communication cable remains coupled between the control device and the imaging assembly as a rotational orientation of the knob changes.

5. The visualization system of claim 1 further comprising:
   a speculum defining a longitudinal axis and a distal tip, the speculum coupled to the knob such that the longitudinal axis is coaxial with the rotational axis of the knob, and the speculum rotates as the knob rotates;
   an imaging lumen disposed on an inside surface of the speculum, the imaging lumen defining a closed bottom, the imaging assembly disposed within the imaging lumen; and
   a working channel defined through the speculum, the working change distinct from the imaging lumen.

6. The visualization system of claim 5 wherein a distal end of the imaging lumen defines a setback distance from the distal tip such that a field of view of the imaging assembly overlaps a portion of an inside diameter of the speculum at the distal tip.

7. The visualization system of claim 5 wherein the speculum defines a shape of an inverted conic frustum.

8. A visualization system comprising:
a control device defining an upper surface and a lower surface;
a display visible through the upper surface of the control device;
a handle coupled to the lower surface and extending away from the lower surface;
a knob coupled to the control device, the knob configured to rotate about a rotational axis;
an imaging assembly mechanically coupled to the knob and communicatively coupled to the control device, the imaging assembly configured to rotate around the rotational axis based on rotation of the knob, the control device configured to display an image on the display, the image captured by the imaging assembly;
a rotation sensor in operational relationship to the knob and communicatively coupled to the control device, the rotation sensor configured to sense rotation of the knob and the imaging assembly;
wherein the control device is configured to rotate the image on the display responsive to rotation of the knob such that the image remains in a consistent orientation despite rotation of the image assembly, and wherein the rotation sensor further comprises:
a first conductive pattern;
a second conductive pattern distinct from and electrically isolated from the first conductive pattern;
a conductive member coupled to the knob;
a measurement circuit electrically coupled to the first conductive pattern, the second conductive pattern, and the conductive member;
the measurement circuit configured to sense rotation of the knob based on a capacitive measurement between the conductive member, the first conductive pattern, and the second conductive pattern.

9. The visualization system of claim 8:
wherein the first conductive pattern further comprises a wide end having a first width and a narrow end having a second width smaller than the first width, the first conductive pattern extending in a circular pattern;
wherein the second conductive pattern further comprises a wide end having a third width and a narrow end having a fourth width smaller than the third width, the second conductive pattern extending in a circular pattern alongside the first conductive pattern; and
wherein a width of the first conductive pattern gets smaller with circular distance in a first direction around the circular pattern, and a width of the second conductive pattern gets larger in the first direction around the circular pattern.

10. A visualization system comprising:
a control device defining an upper surface and a lower surface;
a display visible through the upper surface of the control device;
a handle coupled to the lower surface and extending away from the lower surface;
a knob coupled to the control device, the knob configured to rotate about a rotational axis;
an imaging assembly mechanically coupled to the knob and communicatively coupled to the control device, the imaging assembly configured to rotate around the rotational axis based on rotation of the knob, the control device configured to display an image on the display, wherein the image is captured by the imaging assembly;
a rotation sensor in operational relationship to the knob and communicatively coupled to the control device, the rotation sensor configured to sense rotation of the knob and the imaging assembly, wherein the control device is configured to rotate the image on the display responsive to rotation of the knob such that the image remains in a consistent orientation despite rotation of the image assembly;
a post defining a proximal end and a distal end, the proximal end of the post coupled to the lower surface of the control device, and the post extending away from the lower surface;
a base coupled to the distal end of the post, the base defining an upper surface, a lower surface, and an aperture;
the knob disposed on the upper surface of the base;
the imaging assembly extending through the aperture and below the lower surface of the base;
a first notch medially disposed on a first side of the post, the first notch defines a closed bottom, an open top, and a channel; and
a second notch medially disposed on a second side of the post opposite the first side, the second notch defines a closed bottom, an open top, and a channel.

11. The visualization system of claim 10 further comprising the channel of the first notch is parallel with the channel of the second notch.

12. A visualization system comprising:
a control device defining an upper surface and a lower surface;
a display visible through the upper surface of the control device;
a handle coupled to the lower surface and extending away from the lower surface;
a knob coupled to the control device, the knob configured to rotate about a rotational axis;
an imaging assembly mechanically coupled to the knob and communicatively
coupled to the control device, the imaging assembly configured to rotate around the rotational axis based on rotation of the knob, the control device configured to display an image on the display, wherein the image is captured by the imaging assembly;
an elongate shaft defining a proximal end and a distal end, the proximal end rigidly coupled to the knob;
an optical sensor disposed within the elongate shaft, the optical sensor defining an optical axis, and the optical sensor communicatively coupled to the control device;
an illumination source disposed within the elongate shaft;
wherein the optical axis forms a non-zero angle with the rotational axis of the knob;
a distal optical lens disposed on the distal end of the elongate shaft, the imaging assembly having a field of view through the distal optical lens along the optical axis; and
an illumination window disposed on the distal end of the elongate shaft, the illumination window having a illumination ray path at least partially coextensive with the field of view.

13. A visualization system comprising:
a control device defining an upper surface and a lower surface;
a display visible through the upper surface of the control device;
a handle coupled to the lower surface and extending away from the lower surface;

a knob coupled to the control device, the knob configured to rotate about a rotational axis;

an imaging assembly mechanically coupled to the knob and communicatively coupled to the control device, the imaging assembly configured to rotate around the rotational axis based on rotation of the knob and the imaging assembly comprising:

an elongate shaft defining a proximal end and a distal end, the proximal end rigidly coupled to the knob;

an optical sensor disposed within the elongate shaft, the optical sensor defining an optical axis, and the optical sensor communicatively coupled to the control device; and an illumination source disposed within the elongate shaft;

wherein the optical axis forms a non-zero angle with the rotational axis of the knob, and the optical axis of the optical sensor intersects the rotational axis of the knob; and the control device configured to display an image on the display, the image captured by the imaging assembly.

14. A visualization system comprising:

a control device defining an upper surface and a lower surface;

a display visible through the upper surface of the control device;

a handle coupled to the lower surface and extending away from the lower surface;

a knob coupled to the control device, the knob configured to rotate about a rotational axis;

an imaging assembly mechanically coupled to the knob and communicatively coupled to the control device, the imaging assembly configured to rotate around the rotational axis based on rotation of the knob, the control device configured to display an image on the display, wherein the image is captured by the imaging assembly;

a communication cable coupled between the imaging assembly and the control device, the communication cable remains coupled between the control device and the imaging assembly as a rotational orientation of the knob changes;

a base rigidly coupled to the control device, the base defining an aperture;

a stationary circular rack rigidly coupled to and at least partially circumscribing the aperture;

a rotatable circular rack rigidly coupled to the knob and at least partially circumscribing the rotational axis of the knob;

a pinion disposed between the stationary circular rack and the rotatable circular rack, the pinion configured to translate along the stationary circular rack responsive to relative rotational movement of the rotatable circular rack;

a circular disk having an annular channel defined on an outside diameter of the circular disk, the circular disk coupled to the pinion and configured to translate with the pinion; and the communication cable at least partially circumscribes the circular disk within the annular channel.

\* \* \* \* \*